United States Patent
Takahashi et al.

(10) Patent No.: US 7,902,226 B2
(45) Date of Patent: Mar. 8, 2011

(54) DEHALOGENO-COMPOUNDS

(75) Inventors: Hisashi Takahashi, Edogawa-ku (JP);
Rie Miyauchi, Edogawa-ku (JP); Masao Itoh, Edogawa-ku (JP); Makoto Takemura, Edogawa-ku (JP); Isao Hayakawa, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 887 days.

(21) Appl. No.: 11/644,901

(22) Filed: Dec. 26, 2006

(65) Prior Publication Data

US 2007/0123560 A1 May 31, 2007

Related U.S. Application Data

(63) Continuation of application No. 10/432,043, filed as application No. PCT/JP01/10086 on Nov. 19, 2001, now abandoned.

(30) Foreign Application Priority Data

Nov. 20, 2000 (JP) .............................. P.2000-352269
Aug. 20, 2001 (JP) .............................. P.2001-248822

(51) Int. Cl.
*C07D 215/38* (2006.01)
*A61K 31/04* (2006.01)

(52) U.S. Cl. ......... 514/312; 514/303; 514/305; 514/299; 546/119; 546/121; 546/123; 546/153; 546/156

(58) Field of Classification Search .................. 514/312, 514/303, 305, 299; 546/119, 121, 123, 153, 546/156
See application file for complete search history.

(56) References Cited

U.S. PATENT DOCUMENTS

| | | | |
|---|---|---|---|
| 5,098,912 A | 3/1992 | Hayakawa et al. | |
| 5,476,950 A | 12/1995 | Hayakawa et al. | |
| 5,849,757 A | 12/1998 | Takemura et al. | |
| 5,910,498 A | 6/1999 | Yazaki et al. | |
| 5,998,436 A | 12/1999 | Yazaki et al. | |
| 6,121,285 A * | 9/2000 | Takemura et al. | 514/312 |
| 6,184,388 B1 * | 2/2001 | Takemura et al. | 548/566 |
| 6,391,889 B2 | 5/2002 | Takemura et al. | |
| 6,448,266 B1 | 9/2002 | Takemura et al. | |
| 6,462,040 B1 | 10/2002 | Takemura et al. | |
| 6,949,662 B2 | 9/2005 | Takemura et al. | |
| 2002/0077345 A1 | 6/2002 | Takemura et al. | |

FOREIGN PATENT DOCUMENTS

| | | |
|---|---|---|
| EP | 0 807 630 A | 11/1997 |
| EP | 0 911 328 A1 | 4/1999 |
| EP | 0 919 553 A | 6/1999 |
| EP | 0 924 213 A | 6/1999 |
| EP | 0 977 328 A | 2/2000 |
| EP | 0 995 744 A | 4/2000 |
| EP | 1 020 459 A | 7/2000 |
| JP | 10-81682 A | 3/1998 |
| JP | 3760172 B2 | 1/2006 |
| WO | WO 97/19072 A1 | 5/1997 |
| WO | WO 98/54169 A1 | 3/1998 |
| WO | WO 98/52939 A1 | 11/1998 |
| WO | 9854169 * | 12/1998 |
| WO | WO 99/14214 A1 | 3/1999 |
| WO | 00/31062 A1 | 6/2000 |

OTHER PUBLICATIONS

Israeli Office Action dated Dec. 10, 2007.
Rejection on a JP application, pp. 1-11, mailed Nov. 4, 2004.
Koichi Yabe, et al., "Safety evaluation of antibacterial drugs (single intravenous dose toxicity study in mice)", New Product Research Laboratories I, Daiichi Pharmaceutical Co., Ltd., Tokyo, Japan, prepared on Aug. 28, 2000 for internal distribution only.
Koichi Yabe, et al., "Safety evaluation of antibacterial drugs (micronucleus test of quinolones in mice)", New Product Research Laboratories I, Daiichi Pharmaceutical Co., Ltd., Tokyo, Japan, prepared on Oct. 25, 2000 for internal distribution only.
Satoru Ito, et al., "Micronucleus test of D01-5816d in rats (confirmation study)", Drug Safety Research Laboratory, Daiichi Pharmaceutical Co., Ltd., Tokyo, Japan, prepared on Feb. 2001 for internal distribution only.
Hayashizaki (Igarashi), "Rapid report of early safety evaluation (field: antibacterial drugs)", prepared on Mar. 6, 2003 for internal distribution only.
Nakayama (Igarashi), "Rapid report of early safety evaluation (field: antibacterial drugs)", prepared on Sep. 11, 2003 for internal distribution only. Katsuko Fujikawa, et al., "In Vitro Antibacterial Activity of DX-619, a Novel Des-Fluoro(6) Quinolone", Antimicrobial Agents and Chemotherapy, Jul. 2005, p. 3040-3045, vol. 49, No. 7.
Katsuko Fujikawa, et al., "DX-619: Antibacterial activity against clinical isolates", New Product Research Laboratories I, Daiichi Pharmaceutical Co., Ltd., Tokyo, Japan, prepared on Feb. 12, 2004 for internal distribution only.
Investigator's Brochure DX-619, Daiichi Pharmaceutical Co. & Ltd., Feb. 5, 2007, p. 64-70.
Exhibit A: Data Summary, prepared on Mar. 2007 for purposes of accompanying IDS.
Exhibit B: Data Summary, prepared on Mar. 2007 for purposes of accompanying IDS.

* cited by examiner

*Primary Examiner* — D. Margaret Seaman
(74) *Attorney, Agent, or Firm* — Sughrue Mion, PLLC

(57) ABSTRACT

3-(1-Aminocycloalkyl)pyrrolidinyl-substituted-6-dehalodeno(hydrogen-substituted)quinolon carboxylic acid derivatives having specific substituents as represented by the following formula (I), its salts, and hydrates thereof exhibit a broad and potent antibacterial activity on gram-negative and gram-positive bacteria, in particular, resistant bacteria typified by gram-positive cocci, including MRSA, PRSP and VRE. Thus these compounds are usable as drugs.

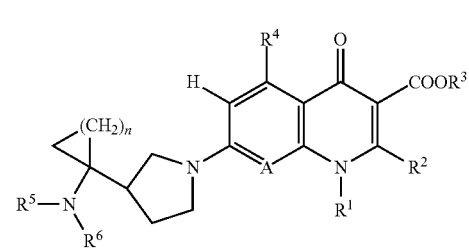

77 Claims, No Drawings

DEHALOGENO-COMPOUNDS

This is a continuation of application Ser. No. 10/432,043 filed May 19, 2003 now abandoned, which is a §371 National Stage Application of International Application No. PCT/JP01/10086 filed Nov. 19, 2001.

TECHNICAL FIELD

This invention relates to a synthetic quinolone antibacterial agent which is useful as medicaments, veterinary drugs, drugs for fishery use, or antibacterial preservatives.

BACKGROUND ART

Since the discovery of norfloxacin, synthetic quinolone antibacterial agents have been improved in antibacterial activity and pharmacokinetics, and many compounds are now used in the clinical filed as chemotherapeutic agents which are effective for in almost systemic infectious diseases.

In recent years, generation of bacteria having low sensitivity to synthetic quinolone antibacterial agents have been increasing in clinical situations. For example, like the case of Staphylococcus aureus (MRSA) and Streptococcus pneumococcus (PRSP) which are insusceptible to β-lactam antibiotics and Enterococcus (VRE) which is insusceptible to aminoglycoside antibacterial agents, a case has been increasing in which a gram-positive bacteria originally resistant to drugs other than synthetic quinolone antibacterial agents also became low sensitive to synthetic quinolone antibacterial agents. In consequence, synthetic quinolone antibacterial agents having higher efficacy are thus being demanded in clinical situations.

With regard to the side effects of synthetic quinolone antibacterial agents, in addition to the central nervous system stimulation effect, which has been a problem since priorly, the induction of convulsion resulting from combined use with nonsteroidal anti-inflammatory agents, phototoxicity, etc. have also become known, and the development of synthetic quinolone antibacterial agents having higher safety is thus also being demanded.

It is known that the structure of the substituents at the 7-position and 1-position (or positions corresponding to these positions; the same shall apply hereinafter) have a large influence on the antibacterial activity, pharmacokinetics, and safety of synthetic quinolone antibacterial agents.

Quinolone derivatives, having a pyrrolidinyl group having an aminomethyl group at the 3-position, as the substituent at the 7-position of the quinolone mother skeleton, are known to exhibit strong antibacterial activity against gram-negative and gram-positive bacteria. For example, there are 7-[3-(1-aminomethyl)pyrrolidin-1-yl]quinolone carboxylic acid derivatives [Journal of Medicinal Chemistry, vol. 29, p. 445 (1986)].

Furthermore, known examples of quinolone carboxylic acid derivatives having a substituent on the carbon atom of the aminomethyl group of the 3-(1-aminomethyl)pyrrolidin-1-yl group include 7-[3-(1-aminoethyl)pyrrolidin-1-yl]quinolone carboxylic acid derivatives [Journal of Medicinal Chemistry, vol. 36, p. 871 (1993)]; 7-[3-(1-amino-1-methylethyl)pyrrolidin-1-yl]quinolone carboxylic acid derivatives [Journal of Medicinal Chemistry, vol. 37, p. 733 (1994)]; and 7-[3-(1-aminoalkyl)pyrrolidin-1-yl]quinolone carboxylic acid derivatives [Chemical and Pharmaceutical Bulletin, vol. 42, p. 1442 (1994)], etc.

However, though the abovementioned quinolone derivatives, having a 3-(aminomethyl)pyrrolidin-1-yl group, a 3-(1-aminoethyl)pyrrolidin-1-yl group, or a group having a structure similar to these as a substituent, are compounds which exhibit strong antibacterial activity, it has been found that due to the low selective toxicity [see for example, Journal of Antimicrobial Chemotherapy, vol. 33, p. 685 (1994)], these compounds act not only on bacteria but also on the cells of eukaryotic organisms, and they are difficult to use as medical drugs or as veterinary drugs. Therefore, quinolone compounds having these substituents have not been put to actual clinical use up until now.

Meanwhile, quinolone carboxylic acid derivatives, which have a 3-(1-aminocycloalkyl)pyrrolidin-1-yl group as a substituent and are relevant to the present invention, have been described in the form of a broad concept in PCT/JP96/00208, which provides a description of compounds with the structure shown in formula A or formula B. That is, with a quinolone compound of formula A, the substituent ($X^1$) at the 6-position is defined as being a halogen atom or a hydrogen atom. However, only quinolone carboxylic acids wherein the fluorine atom or other halogen atom is the substituent at the 6-position are disclosed specifically in the abovementioned patent application. Therefore, PCT/JP96/00208 does not provide a specific description concerning quinolone carboxylic acids wherein hydrogen is substituted at the 6-position. Furthermore, this publication does not provide any specific disclosure as embodiments of 3-(1-aminocycloalkyl)pyrrolidinyl-substituted-6-hydrogen-substituted-quinolone carboxylic acids, wherein the present invention is concerned.

[Formula A]

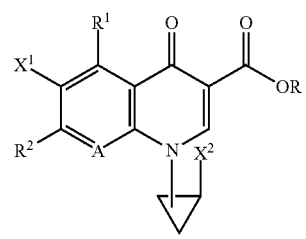

[In the above formula A, $X^1$ represents a halogen atom or a hydrogen atom and $X^2$ represents a halogen atom. (The definitions of the substituents in the compound shown in formula A are those given in PCT/JP96/00208 and are irrelevant to the definitions of substituents of the present invention even when the same symbols are used.)]

In the above formula A, $R^2$ is represented by formula B:

[Formula B]

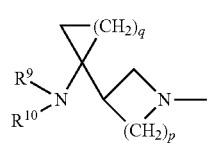

[In the above formula B, p represents an integer from 1 to 3, q represents an integer from 1 to 3, $R^9$ represents a hydrogen atom or an alkyl group having 1 to 6 carbon atoms, $R^{10}$ represents a hydrogen atom, an alkyl group having 1 to 6 carbon atoms, an alkyl group having 1 to 6 carbon atoms that has a hydroxyl group, or an alkyl group having 1 to 6 carbon atoms that has a halogen atom. (The definitions of the substituents in the compound shown in formula B are those given in PCT/JP96/00208 and are irrelevant to the definitions of substituents of the present invention even when the same symbols are used.)]

Besides the above, an example of a literature that indicates a quinolone carboxylic acid derivative, which has a 3-(1-aminocycloalkyl) pyrrolidin-1-yl group and is relevant to the present invention, is Chemical and Pharmaceutical Bulletin, vol. 42, p. 1442 (1994). However, this literature does not contain any description whatsoever concerning 3-(1-aminocycloalkyl)pyrrolidinyl-substituted-6-hydrogen-substituted-quinolone carboxylic acids, which are compounds of the present invention.

Furthermore, for example, PCT/WO99/14214 indicates a 6-hydrogen-substituted-quinolone carboxylic acid derivative, in which a nitrogen-containing heterocyclic substituent, for example, the 3-(1-aminoethyl)pyrrolidin-1-yl group, is introduced via a carbon-nitrogen bond into the 7-position of the quinolone skeleton and which is relevant to this invention. This application describes compounds represented by the formulas C and D. However, this application does not contain any description whatsoever concerning a 3-(1-aminocycloalkyl) pyrrolidin-1-yl group, which is relevant to the present invention, as a substituent at the 7-position of the quinolone skeleton shown in formula C. Furthermore, this application does not contain any description whatsoever concerning 3-(1-aminocycloalkyl)pyrrolidinyl-substituted-6-hydrogen-substituted-quinolone carboxylic acids, which are relevant to the present invention and have the abovementioned group as a substituent.

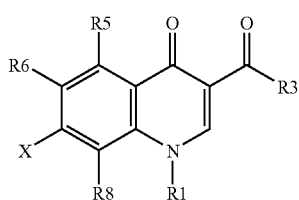

[Formula C]

[In the above formula C, R1 represents a cyclic alkyl group having 3 to 6 carbon atoms, an alkyl group having 1 or 2 carbon atoms, a straight-chain alkenyl group having 2 to 3 carbon atoms, or a branched-chain alkyl group or alkenyl group having 3 to 4 carbon atoms, this alkyl group or cyclic alkyl group may be unsubstituted or the alkyl group or cyclic alkyl group may be substituted by 1 to 3 fluorine atoms or by a phenyl group which is unsubstituted or is substituted by 1 to 3 fluorine atoms or is substituted at the 4-position by a single hydroxyl group, R6 represents a hydrogen atom, a hydroxyl group, an aminocarbonyl group, a bromine atom, a cyano group, an alkyl group having 1 or 2 carbon atoms, or an alkenyl group or alkynyl group having 2 to 4 carbon atoms, and this alkyl group may be unsubstituted or the alkyl group may be substituted by a methyl group or an ethyl group that is unsubstituted or is substituted by 1 to 3 fluorine atoms or one hydroxyl group or amino group. (The definitions of the substituents in the compound shown in formula C are those given in PCT/WO99/14214 and are irrelevant to the definitions of substituents of the present invention even when the same symbols are used.)]

In the above formula, X is represented by formula D:

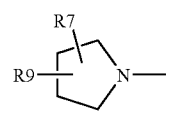

[Formula D]

[In the above formula D, R7 represents an amino group, which is bonded to a carbon that is not adjacent the nitrogen atom of the pyrrolidine ring and may be unsubstituted or substituted by one or two alkyl groups with 1 to 3 carbon atoms, or an aminoalkyl group, which is bonded to a carbon on the pyrrolidine ring and may be unsubstituted or substituted by an alkyl group having 1 to 3 carbon atoms, R9 represents a group selected from among the group comprised of a hydrogen atom, an alkyl group having 1 to 4 carbon atoms, an alkenyl group and alkynyl group having 2 to 6 carbon atoms, and fused and spiroalkyl group having 3 to 6 carbon atoms, the alkyl group portions of these groups may be unsubstituted or substituted by 1 to 3 fluorine atoms, and the abovementioned substituents R7 and R9 may be integrated to form a fused or spiro type ring structure with the pyrrolidine ring, with this fused or spirocyclic part being formed from 2 to 5 carbon atoms and 0 or 1 nitrogen atom. (The definitions of the substituents in the compound shown in formula D are those given in PCT/WO99/14214 and are irrelevant to the definitions of substituents of the present invention even when the same symbols are used.)]

Other examples of literature that indicate 6-hydrogen-substituted-quinolone carboxylic acid derivatives, which are relevant to the present invention, include Journal of Medicinal Chemistry, vol. 39, p. 4952 (1996). However, even this literature does not contain any description whatsoever concerning 3-(1-aminocycloalkyl)pyrrolidinyl-substituted-6-hydrogen-substituted-quinolone carboxylic acids, which are the compounds of the present invention.

DISCLOSURE OF THE INVENTION

The present inventors have conducted intensive studies to obtain quinolone compounds, which are excellent in antibacterial activity, high in efficacy, and yet excellent in safety. As a result, it has been found that 3-(1-aminocycloalkyl)pyrrolidinyl-substituted-6-dehalogeno(hydrogen-substituted)quinolone carboxylic acid derivatives represented by formula (I) described below, its salts and hydrates thereof exhibit potent antibacterial activity upon a broad range of gram-negative bacteria and gram-positive bacteria and, in particular, exhibit potent antibacterial activity against drug-resistant bacteria, as represented by gram-positive cocci, including MRSA, PRSP, and VRE.

Furthermore, it has been found that, in addition to exhibiting such excellent antibacterial activity, the compounds of this invention are excellent both in terms of safety and pharmacokinetics and thus enable use in clinical situations, which could not be achieved with compounds prior to this invention which have substituents of the same structure at the 7-position of the quinolone mother skeleton. The present invention has been achieved based on these findings.

A comparison of the 6-hydrogen-substituted-quinolone carboxylic acid derivatives represented by formula (I), its salts and hydrates thereof according to the present invention with quinolone compounds wherein the hydrogen at the 6-position of a compound of this invention is substituted by a fluorine atom shows that both types of compounds exhibit excellent antibacterial activity upon a broad range of both gram-negative bacteria and gram-positive bacteria, including drug-resistant bacteria. However, it has been found unexpectedly that the 6-hydrogen-substituted-quinolone derivatives, which are the compounds of this invention, are compounds that, in comparison to the 6-fluorine-substituted-quinolone derivatives, are compounds of excellent safety that are reduced in acute toxicity and significantly reduced in micronucleus induction, and also exhibit good pharmacokinetics, such as improved urinary recovery, etc.

That is, the present inventors have found that even a quinolone compound, which has a 3-(1-aminocycloalkyl)pyrrolidin-1-yl group having a cyclic alkyl group as a substituent on the methyl group of the 3-(aminomethyl)pyrrolidin-1-yl group and which as has been mentioned above is known to be low in selective toxicity, will unexpectedly be a compound with excellent selective toxicity and be a compound of excellent pharmacokinetics as long as it is a quinolone compound with the structure of the present invention.

That is, the present invention concerns compounds represented by the following general formula (I), its salts, and hydrates thereof:

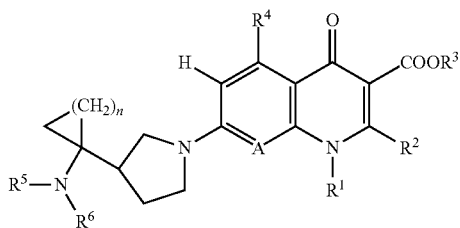

I

[wherein $R^1$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms, which may have a substituent, an aryl group, which may have a substituent, a heteroaryl group, which may have a substituent, an alkoxy group having 1 to 6 carbon atoms, or an alkylamino group having 1 to 6 carbon atoms;

$R^2$ represents an alkylthio group having 1 to 6 carbon atoms or a hydrogen atom, wherein $R^2$ and the abovementioned $R^1$ may be integrated to form a ring structure by incorporating a part of the mother skeleton, the thus formed ring may contain a sulfur atom as a ring-constituent atom, and the ring may be substituted by an alkyl group having 1 to 6 carbon atoms, which may have a substituent;

$R^3$ represents a phenylalkyl group composed of an alkylene group having 1 to 6 carbon atoms and a phenyl group, an alkyl group having 1 to 6 carbon atoms, an alkoxymethyl group having 2 to 7 carbon atoms, a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxole-4-ylmethyl group, or a 3-acetoxy-2-oxobutyl group;

$R^4$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a hydroxyl group, a thiol group, or a halogenomethyl group, and among the above, the amino group may have one or more substituents selected from among the group consisting of an alkyl group having 1 to 6 carbon atoms, an acyl group having 2 to 5 carbon atoms, and a formyl group;

A represents a nitrogen atom or a partial structure represented by formula (II):

II (wherein $X^1$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a halogen atom, a cyano group, a halogenomethyl group, or a halogenomethoxy group, among the above, the amino group may have one ore more substituents selected from the group consisting of an alkyl group having 1 to 6 carbon atoms, an acyl group having 2 to 5 carbon atoms, and a formyl group, wherein $X^1$ and the aforementioned $R^1$ may be integrated to form a ring structure by incorporating a part of the mother skeleton, the thus formed ring may contain an oxygen atom, a nitrogen atom, or a sulfur atom as a ring constituent atom, and this ring may be substituted by an alkyl group having 1 to 6 carbon atoms, which may have a substituent);

each of $R^5$ and $R^6$ independently represents an alkyl group having 1 to 6 carbon atoms, a hydrogen atom, or a substituted carboxyl group derived from an amino acid, dipeptide, or tripeptide, wherein the alkyl group may have one ore more substituents selected from the group consisting of an alkylthio group having 1 to 6 carbon atoms, an alkoxy group having 1 to 6 carbon atoms, a hydroxyl group, and a halogen atom; and n represents an integer 1 or 2].

The present invention also relates to each of the following:
a compound of the above formula (I), its salts or hydrates thereof, wherein the compound of formula (I) is a stereochemically pure compound;
a compound of the formula (I), its salts or hydrates thereof, wherein n in the formula (I) is 1;
a compound of the formula (I), its salts or hydrates thereof, wherein $R^3$ in the formula (I) is a hydrogen atom;
a compound of the formula (I), its salts or hydrates thereof, wherein $R^2$ in the formula (I) is a hydrogen atom;
a compound of the formula (I), its salts or hydrates thereof, wherein $R^4$ in the formula (I) is a hydrogen atom;
a compound of the formula (I), its salts or hydrates thereof, wherein A in the formula (I) is a partial structure represented by the formula (II);
a compound of the formula (I), its salts or hydrates thereof, wherein $X^1$ in the formula (II) is a methoxy group, a methyl group, a difluoromethoxy group, a fluorine atom, or a chlorine atom;
a compound of the formula (I), its salts or hydrates thereof, wherein $X^1$ in the formula (II) is a methoxy group or a methyl group;
a compound of the formula (I), its salts or hydrates thereof, wherein each of $R^5$ and $R^6$ in the formula (I) is a hydrogen atom;
a compound of the formula (I), its salts or hydrates thereof, wherein one of either $R^5$ or $R^6$ in the formula (I) is a hydrogen atom and the other is a methyl group;
a compound of the formula (I), its salts or hydrates thereof, wherein one of either $R^5$ or $R^6$ in formula (I) is a hydrogen atom and the other is a substituted carboxyl group derived from an amino acid, a dipeptide, or a tripeptide;

a compound of the formula (I), its salts or hydrates thereof, wherein each of the $R^5$ and $R^6$ in formula (I) is a combination of a hydrogen atom and a methyl group;

a compound of the formula (I), its salts or hydrates thereof, wherein $R^6$ in formula (I) is a substituted carboxyl group derived from an amino acid, a dipeptide, or a tripeptide;

a compound of the formula (I), its salts or hydrates thereof, wherein the cyclic alkyl group having 3 to 6 carbon atoms, which may have a substituent, in $R^1$ is a halogenocyclopropyl group;

a compound of the formula (I), its salts or hydrates thereof, wherein the halogenocyclopropyl group is a 1,2-cis-2-halogenocyclopropyl group;

a compound of the formula (I), its salts or hydrates thereof, wherein the halogenocyclopropyl group is a stereochemically pure substituent;

a compound of the formula (I), its salts or hydrates thereof, wherein the halogenocyclopropyl group is a (1R,2S)-2-halogenocyclopropyl group;

a compound of the formula (I), its salts or hydrates thereof, wherein the halogen atom of the halogenocyclopropyl group is a fluorine atom;

7-[3-(R)-(1-aminocyclopropyl)pyrrolidin-1-yl]-1-[2-(S)-fluoro-1-(R)-cyclopropyl]-1,4-dihydro-4-oxo-1,8-naphthyridine-3-carboxylic acid, its salts or hydrates thereof;

7-[3-(R)-(1-aminocyclopropyl)pyrrolidin-1-yl]-1-[2-(S)-fluoro-1-(R)-cyclopropyl]-1,4-dihydro-4-oxoquinoline-3-carboxylic acid, its salts or hydrates thereof;

7-[3-(R)-(1-aminocyclopropyl)pyrrolidin-1-yl]-1-[2-(S)-fluoro-1-(R)-cyclopropyl]-8-chloro-1,4-dihydro-4-oxoquinoline-3-carboxylic acid, its salts or hydrates thereof;

7-[3-(R)-(1-aminocyclopropyl)pyrrolidin-1-yl]-1-[2-(S)-fluoro-1-(R)-cyclopropyl]-8-fluoro-1,4-dihydro-4-oxoquinoline-3-carboxylic acid, its salts or hydrates thereof;

7-[3-(R)-(1-aminocyclopropyl)pyrrolidin-1-yl]-1-[2-(S)-fluoro-1-(R)-cyclopropyl]-8-difluoromethoxy-1,4-dihydro-4-oxoquinoline-3-carboxylic acid, its salts or hydrates thereof;

7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid, its salts or hydrates thereof;

7-[3-(R)-[1-(methylamino)cyclopropyl]pyrrolidin-1-yl]-1-[2-(S)-fluoro-1-(R)-cyclopropyl]-1,4-dihydro-8-methoxy-4-oxoquinoline-3-carboxylic acid, its salts or hydrates thereof;

7-[3-(R)-(1-aminocyclopropyl)pyrrolidin-1-yl]-1-[2-(S)-fluoro-1-(R)-cyclopropyl]-1,4-dihydro-8-methyl-4-oxoquinoline-3-carboxylic acid, its salts or hydrates thereof;

7-[3-(R)-[1-(methylamino)cyclopropyl]pyrrolidin-1-yl]-1-[2-(S)-fluoro-1-(R)-cyclopropyl]-1,4-dihydro-8-methyl-4-oxoquinoline-3-carboxylic acid, its salts or hydrates thereof;

7-[3-(R)-[1-(ethylamino) cyclopropyl]pyrrolidin-1-yl]-1-[2-(S)-fluoro-1-(R)-cyclopropyl]-1,4-dihydro-8-methyl-4-oxoquinoline-3-carboxylic acid, its salts or hydrates thereof;

5-amino-7-[3-(R)-(1-aminocyclopropyl)pyrrolidin-1-yl]-1-[2-(S)-fluoro-1-(R)-cyclopropyl]-1,4-dihydro-8-fluoro-4-oxoquinoline-3-carboxylic acid, its salts or hydrates thereof;

5-amino-7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid, its salts or hydrates thereof;

5-amino-7-[3-(R)-(1-aminocyclopropyl)pyrrolidin-1-yl]-1-[2-(S)-fluoro-1-(R)-cyclopropyl]-1,4-dihydro-8-methyl-4-oxoquinoline-3-carboxylic acid, its salts or hydrates thereof;

5-amino-7-[3-(R)-[1-(methylamino)cyclopropyl]pyrrolidin-1-yl]-1-[2-(S)-fluoro-1-(R)-cyclopropyl]-1,4-dihydro-8-methoxy-4-oxoquinoline-3-carboxylic acid, its salts or hydrates thereof;

10-[3-(R)-(1-aminocyclopropyl)pyrrolidin-1-yl]-2,3-dihydro-3-(S)-methyl-7-oxo-7H-pyrido[1,2,3-de][1,4]benzoxazine-6-carboxylic acid, its salts or hydrates thereof;

1-(cyclopropyl)-8-methyl-7-[3-(R)-[1-(methylamino)cyclopropyl]pyrrolidin-1-yl]-1,4-dihydro-4-oxoquinoline-3-carboxylic acid, its salts or hydrates thereof;

a medicament, which comprises a compound of formula (I), its salts or hydrates thereof as an active ingredient;

an antibacterial agent, which comprises a compound of formula (I), its salts or hydrates thereof as an active ingredient;

a therapeutic agent for an infectious disease, which comprises a compound of the formula (I), its salts or hydrates thereof as an active ingredient;

a method for treating a disease, which comprises administrating a compound of the formula (I), its salts or hydrates thereof as an active ingredient;

a method for treating an infectious disease, which comprises administrating a compound of the formula (I), its salts or hydrates thereof as an active ingredient;

a method for producing a medicament, which comprises formulating a compound of the formula (I), its salts or hydrates thereof as an active ingredient;

a method for producing an antibacterial agent, which comprises formulating a compound of the formula (I), its salts or hydrates thereof as an active ingredient;

a method for producing an infectious disease treating agent, which comprises formulating a compound of the formula (I), its salts or hydrates thereof as an active ingredient;

use of a compound of the formula (I), its salts or hydrates thereof for the production of a medicament;

use of a compound of the formula (I), its salts or hydrates thereof for the production of an antibacterial agent;

use of a compound of the formula (I), its salts or hydrates thereof for the production of an infectious disease treating agent;

and so on.

MODE FOR CARRYING OUT THE INVENTION

The various substituents of the compound of this invention represented by formula (I):

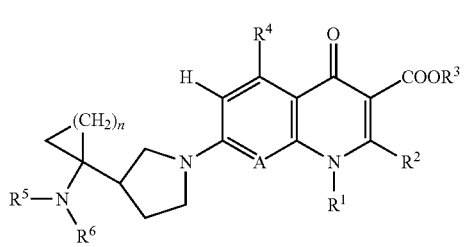

($R^1$, $R^2$, $R^3$, $R^4$, $R^5$, $R^6$, n and A are defined as has been described above) shall now be described. (For the 6-position of the quinolone mother skeleton or an equivalent position in the structural formulae indicated in the present specification, in order to stress that a hydrogen atom is bonded, the hydrogen atom that is bonded to a carbon, which is normally not indicated as customary in structural formulae in organic chemistry, is indicated in some cases (in the form of "—H"). However, the structural formulae of this specification are indicated in line with the rules of indication of structural formulae that are normally practiced in the field of organic chemistry, and a hydrogen atom that is bonded to a carbon atom will not always be indicated but will normally be omitted.)

The substituent $R^1$ is an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms, which may have a substituent, an aryl group, which may have a substituent, a heteroaryl group, which may have a substituent, an alkoxy group having 1 to 6 carbon atoms, or an alkylamino group having 1 to 6 carbon atoms.

Here, an alkyl group having 1 to 6 carbon atoms may be a straight-chain or branched-chain alkyl group, preferably an alkyl group having 1 to 4 carbon atoms, more preferably an ethyl group. As an alkenyl group having 2 to 6 carbon atoms, a vinyl group or a 1-isopropenyl group is preferable. As a halogenoalkyl group having 1 to 6 carbon atoms, a 2-fluoroethyl group is preferable. As a cyclic alkyl group, a cyclopropyl group is especially preferable. The cyclic alkyl group may have a substituent, and a halogen atom is preferable as the substituent. A halogenocyclopropyl group is preferable as the cyclic alkyl group, which may have a substituent, and a fluorine atom is especially preferable as the halogen atom in this group. As a halogenocyclopropyl group, a monohalogenocyclopropyl group is preferable and a cis-substituted group is even more preferable.

Examples of an aryl group, which may have a substituent, include a phenyl group, etc., which may have 1 to 3 substituents selected from the group consisting of an alkyl group having 1 to 6 carbon atoms, an alkoxy group having 1 to 6 carbon atoms, a halogen atom such as fluorine atom, chlorine atom and bromine atom, a hydroxyl group, an amino group, a nitro group, etc. (in the case where the aryl group has a plurality of substituents, the substituents may be of a single type or may be of a plurality of types). To be more specific, a phenyl group, a 2-fluorophenyl group, a 4-fluorophenyl group, a 2,4-difluorophenyl group, a 2-fluoro-4-hydroxyphenyl group, a 3-amino-4,6-difluorophenyl group, and a 4,6-difluoro-3-methylaminophenyl group are preferable. By aryl group, a group that is derived from an aromatic hydrocarbon compound is referred to. Besides the phenyl group, the aryl group may also be a naphthyl group or a tricyclic aryl group having more rings.

A heteroaryl group is a group that is derived from a pentacyclic or hexacyclic aromatic heterocyclic compound that contains one or more hetero atoms selected from among the nitrogen atom, oxygen atom, and sulfur atom. A pentacyclic or hexacyclic nitrogen-containing heterocyclic substituent that contains 1 or 2 nitrogen atoms is especially preferable. For example, a pyridyl group, pyrimidyl group, etc are cired. An alkyl group, a halogen atom, etc. are preferable as substituents on these rings. A 6-amino-3,5-difluoro-2-pyridyl group is especially preferable.

As an alkoxy group having 1 to 6 carbon atoms, an alkoxy group that is derived from an abovementioned alkyl group is preferable and among these, the methoxy group is preferable. For an alkylamino group having 1 to 6 carbon atoms, the alkyl portion may be an abovementioned alkyl group. A methylamino group is preferable as the alkylamino group.

As the substituent $R^1$, a cyclic alkyl group or a halogenocycloalkyl group is preferable. Among these, a cyclopropyl group or a 2-halogenocyclopropyl group is preferable. As the halogen atom in the 2-halogenocyclopropyl group, a fluorine atom is preferable.

The substituent $R^2$ represents an alkylthio group having 1 to 6 carbon atoms or a hydrogen atom, and $R^1$ and $R^2$ may be integrated to form a ring structure comprised of a polymethylene chain by incorporating a part of the mother skeleton (that is, so as to contain the nitrogen atom to which $R^1$ is bonded and the carbon atom to which $R^2$ is bonded). The thus formed ring may contain a sulfur atom as a ring constituent atom, and this ring may also have an alkyl group or halogenoalkyl group having 1 to 6 carbon atoms as a substituent. The formed ring may be tetracyclic to hexacyclic in size and this ring may be also saturated or unsaturated. A methyl group or a fluoromethyl group is preferable as the substituent on the formed ring. Examples of the fused ring structure formed in this manner include the following:

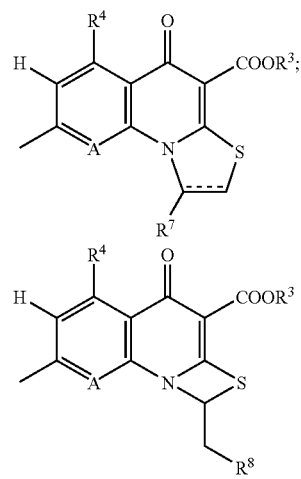

(In the above formula, $R^7$ represents an alkyl group having 1 to 6 carbon atoms, such as a methyl group, a halogenoalkyl group having 1 to 6 carbon atoms, such as a fluoromethyl group, or a hydrogen atom, and $R^8$ represents a halogen atom, such as a fluorine atom, or a hydrogen atom.)

A hydrogen atom is preferable as the substituent $R^2$ of the compound of formula (I).

The substituent $R^3$ is a phenylalkyl group (aralkyl group) composed of an alkylene group having 1 to 6 carbon atoms and a phenyl group, or an alkyl group having 1 to 6 carbon atoms, an alkoxymethyl group having 2 to 7 carbon atoms, a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxole-4-ylmethyl group, or a 3-acetoxy-2-oxobutyl group.

In the case where a compound of this invention is to be used for antibacterial purposes, it is preferable to use a carboxylic acid compound wherein $R^3$ is a hydrogen atom. Meanwhile, a quinolone derivative wherein the carboxylic acid moiety has been made an ester is useful as a synthesis intermediate or as a prodrug. These aspects shall be described in more detail below.

$R^4$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a hydroxyl group, a thiol group, or an halogenomethyl group, and among the above, the amino group may have one ore more substituents selected from the group consisting of an alkyl group having 1 to 6 carbon atoms, an acyl group having 2 to 5 carbon atoms, and a formyl group. In the case where there are a plurality of substituent groups, the substituents may all be of the same type or may be of a plurality of different types.

As an alkyl group, which may either be a straight-chain or branched-chain group having 1 to 6 carbon atoms, a methyl group, an ethyl group, a normal propyl group, or an isopropyl group is preferable. As an alkenyl group, which may either be a straight-chain or branched-chain group having 2 to 6 carbon atoms, a vinyl group is preferable. As an alkynyl group, which may be a straight-chain or branched-chain group having 2 to 6 carbon atoms, an ethynyl group is preferable. As the halogen of a halogenomethyl group, a fluorine atom is especially preferable and the number thereof may be 1 to 3. As an alkoxy group, which may have 1 to 6 carbon atoms, a methoxy group is preferable.

The substituent $R^4$ is preferably a hydrogen atom, an alkyl group, or an amino group, and among these, a hydrogen atom, a methyl group, or unsubstituted amino group ($-NH_2$) is especially preferable.

In the case where $R^4$ is an amino group, a hydroxyl group, or a thiol group, it may be protected by a protective group that is normally used in the relevant fields.

Examples of such protective groups include (substituted) alkoxycarbonyl groups, such as tert-butoxycarbonyl group, 2,2,2-trichloroethoxycarbonyl group, etc.; (substituted) aralkyloxycarbonyl groups, such as benzyloxycarbonyl group, paramethoxybenzyloxycarbonyl group, paranitrobenzyloxycarbonyl group, etc.; (substituted) acyl groups, such as acetyl group, methoxyacetyl group, trifluoroacetyl group, chloroacetyl group, pivaloyl group, formyl group, benzoyl group, etc.; (substituted) alkyl groups or (substituted) aralkyl groups, such as tert-butyl group, benzyl group, paranitrobenzyl group, paramethoxybenzyl group, triphenylmethyl group, etc.; (substituted) ethers, such as methoxymethyl group, tert-butoxymethyl group, tetrahydropyranyl group, 2,2,2-trichloroethoxymethyl group, etc.; and (alkyl and/or aralkyl) substituted silyl groups, such as trimethylsilyl group, isopropyldimethylsilyl group, tert-butyldimethylsilyl group, tribenzylsilyl group, tert-butyldiphenylsilyl group, etc. (here, "(substituted)" signifies that a group may have a substituent). A compound having an amino group, hydroxyl group, or thiol group that is protected by such a substituent is especially preferable as a production intermediate.

A represents a nitrogen atom or a partial structure expressed by formula (II):

II

In the case where A is a partial structure of the formula (II), $X^1$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a halogen atom, a cyano group, a halogenomethyl group, or a halogenomethoxy group, and among the above, the amino group may have one ore more substituents selected from the group consisting of an alkyl group having 1 to 6 carbon atoms, an acyl group having 2 to 5 carbon atoms, and a formyl group.

As a halogen atom, a fluorine atom, a chlorine atom, and a bromine atom are preferable and the fluorine atom and chlorine atom are especially preferable. As an alkyl group, which may be a straight-chain or branched-chain group having 1 to 6 carbon atoms, a methyl group, an ethyl group, a normal propyl group, or an isopropyl group is preferable. As an alkenyl group, which may either be a straight-chain or branched-chain group having 2 to 6 carbon atoms, a vinyl group is preferable. As an alkynyl group, which may be a straight-chain or branched-chain group having 2 to 6 carbon atoms, an ethynyl group is preferable. As the halogen of a halogenomethyl group, a fluorine atom is especially preferable and the number thereof may be 1 to 3. As an alkoxy group, which may have 1 to 6 carbon atoms, a methoxy group is preferable. As the halogen of a halogenomethoxy group, a fluorine atom is especially preferable and the number thereof may be 1 to 3.

Among these substituents, an alkyl group or an alkoxy group is preferable. A methyl group, an ethyl group, a methoxy group, or a difluoromethoxy group is especially preferable.

Further, this $X^1$ and the abovementioned $R^1$ may be integrated to form a ring structure comprised of a polymethylene ring by incorporating a part of the mother skeleton (so as to contain the carbon atom to which $X^1$ is bonded and the nitrogen atom to which $R^1$ is bonded). The thus formed ring may contain an oxygen atom, a nitrogen atom, or a sulfur atom as a ring constituent atom, and this ring may also have as a substituent an alkyl group having 1 to 6 carbon atoms, which may have a substituent in turn.

The formed ring may be pentacyclic to heptacyclic in size and the ring constituent atoms are not limited to a carbon atom and may include an oxygen atom, a nitrogen atom, or a sulfur atom. Further, this ring may be saturated or unsaturated. The thus formed ring may have an alkyl group having 1 to 6 carbon atoms as a substituent. This alkyl group may be considered to be the same as the above-described alkyl group and is preferably a methyl group. This alkyl group may be substituted by a halogen atom, an alkoxy group, etc.

As a partial structure that forms the ring structure formed by $X^1$ and $R^1$, a structure of the following formula:

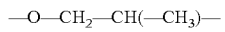

is preferable (the right end of the above is bonded to a nitrogen atom), and especially, the quinolone skeleton of the following structure is preferable:

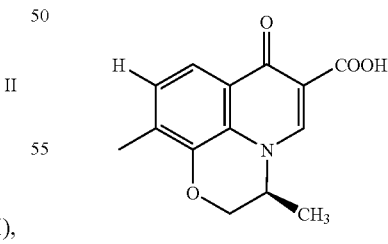

If A is a partial structure of formula (II), preferable combinations of $R^4$ and $X^1$ are those in which $R^4$ is an alkyl group having 1 to 6 carbon atoms, an amino group, a hydrogen atom, or a hydroxyl group and $X^1$ is an alkyl group having 1 to 6 carbon atoms, an alkoxy group 1 to 6 carbon atoms, a halogenomethoxy group, or a hydrogen atom.

More preferable combinations are those in which $R^4$ is an amino group, a hydrogen atom, a hydroxyl group, or a methyl group and $X^1$ is a methyl group, a methoxy group, a difluoromethoxy group, or a hydrogen atom.

Especially preferable combinations are those in which $R^4$ is a hydrogen atom, a hydroxyl group, or a methyl group and $X^1$ is a methyl group or a methoxy group.

Each of substituent $R^5$ and $R^6$ independently represents an alkyl group having 1 to 6 carbon atoms, a hydrogen atom, or a substituted carboxyl group derived from an amino acid, a dipeptide, or a tripeptide.

This alkyl group may have one ore more substituents selected from the group consisting of an alkylthio group having 1 to 6 carbon atoms, an alkoxy group having 1 to 6 carbon atoms, a hydroxyl group, and a halogen atom.

As an alkyl group, which may either be a straight-chain or branched-chain group having 1 to 6 carbon atoms, a methyl group, an ethyl group, a normal propyl group, or an isopropyl group is preferable.

In the case where the alkyl group has a hydroxyl group as a substituent, the alkyl group may be a straight-chain or branched-chain group having 1 to 6 carbon atoms, and the hydroxyl group is more preferably substituted on the terminal carbon atom of the alkyl group. As an alkyl group having a hydroxyl group, those with up to 3 carbon atoms is preferable and a hydroxymethyl group, a 2-hydroxyethyl group, a 2-hydroxypropyl group, a 3-hydroxypropyl group, etc. are preferable.

In the case where the alkyl group has a halogen atom as a substituent, the alkyl group may be a straight-chain or branched-chain group having 1 to 6 carbon atoms, and the halogen atom is preferably a fluorine atom. The number of fluorine atoms may correspond to a mono-substituted condition to a perfluoro-substituted condition. Examples thereof include a monofluoromethyl group, a difluoromethyl group, a trifluoromethyl group, a 2,2,2-trifluoroethyl group, etc.

In the case where the alkyl group has an alkylthio group as a substituent, the alkyl group may be a straight-chain or branched-chain group having 1 to 6 carbon atoms, and the alkylthio group may also be a straight-chain or branched-chain group having 1 to 6 carbon atoms. As an alkyl group having an alkylthio group, an alkylthiomethyl group, an alkylthioethyl group, or an alkylthiopropyl group is preferable and it is more preferable for the alkylthio group to be a group having 1 to 3 carbon atoms as well. More preferable examples thereof include a methylthiomethyl group, an ethylthioethyl group, and a methylthioethyl group.

In the case where the alkyl group has an alkoxy group as a substituent, the alkyl group may be a straight-chain or branched-chain group having 1 to 6 carbon atoms, and the alkoxy group may also be straight-chain or branched-chain group having 1 to 6 carbon atoms. As an alkyl group having an alkoxy group, an alkoxymethyl group, an alkoxyethyl group, or an alkoxypropyl group is preferable and it is more preferable for the alkoxy group to be a group having up to 3 carbon atoms as well. More preferable examples thereof include a methoxymethyl group, an ethoxymethyl group, and a methoxyethyl group.

Preferable combinations of $R^5$ and $R^6$ are those in which one is a hydrogen atom and the other is a hydrogen atom, an alkyl group, or a substituted carboxyl group derived from an amino acid, a dipeptide, or a tripeptide. Among these, a combination in which one of either $R^5$ or $R^6$ is a hydrogen atom and the other is a hydrogen atom or an alkyl group is more preferable. As an alkyl group, a methyl group or an ethyl group is preferable and a methyl group is especially preferable. Thus, a combination in which both $R^5$ and $R^6$ are hydrogen atoms or a combination in which one of either $R^5$ or $R^6$ is a hydrogen atom and the other is a methyl group is especially preferable. A compound of this combination can especially express favorable physiological activity as an antibacterial agent.

A quinolone derivative, wherein one of either substituent $R^5$ or $R^6$ is a hydrogen atom and the other is a substituted carboxyl group derived from an amino acid, a dipeptide, or a tripeptide is especially useful as a prodrug. Specific examples regarding this shall be described below.

A description shall now be given concerning the halogenocyclopropyl group of $R^1$.

The substituent halogen atom is preferably a fluorine atom or a chlorine atom and a fluorine atom is especially preferable.

It is especially preferable for the stereochemical environment at this moiety that the halogen atom and the quinolone carboxylic acid moiety have cis-configuration on the cyclopropane ring. Also, though the cis-configuration substituent in this case may take the form of a 2-(S)-halogeno-1-(R)-cyclopropyl group or a 2-(R)-halogeno-1-(S)-cyclopropyl group, the former is preferable.

Though so-called enantiomorphic isomers are present due to the cis-2-halogenocyclopropyl moiety alone of $R^1$, all of such isomers have been found to be strong in antibacterial activity and high in safety.

A compound of this invention, exhibits excellent characteristics when there is a substituent of the structure represented by the following formula E at the 7-position of a quinolone mother skeleton, in particular, a 1-[2-(S)-fluoro-1-(R)-cyclopropyl]-1,4-dihydro-4-oxoquinoline-3-carboxylic acid skeleton having a 2-(S)-halogeno-1-(R)-cyclopropyl group.

[Formula E]

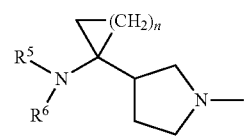

For this substituent, two optical isomers that are in an enantiomorphic relationship exist as a result of the asymmetric carbon atom at the 3-position of the pyrrolidine ring. To be more specific, these are as follows:

[Formula F]

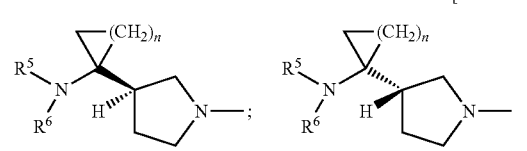

Meanwhile, the correlation of the structural activities of two types of optically active compounds that are due to the steric configuration of the substituent at the 7-position (or its equivalent position) of a 7-[3-(1-aminomethyl)pyrrolidin-1-yl]quinolone carboxylic acid derivative and the correlation of the structural activities of four types of optically active substances that are due to the steric configuration of the substituent at the 7-position of a 7-[3-(1-aminoethyl)pyrrolidin-1-yl]quinolone carboxylic acid derivative are described in Journal of Medicinal Chemistry, vol. 36, p. 1442 (1994). In this literature, it is indicated that among these optical isomers, the isomers of the structures shown in the following formula are highest in antibacterial activity.

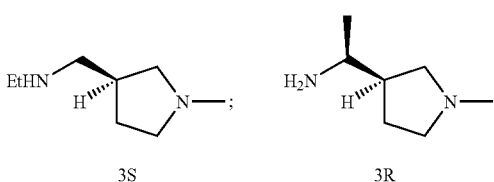

From the steric configurations at the 3-position of these pyrrolidine rings, the present inventors considered that of the two optical isomers shown in above formula F, the following isomer was more preferable:

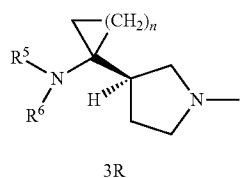

Thus, a more preferable compound of the compounds of this invention has the structure represented by the following formula:

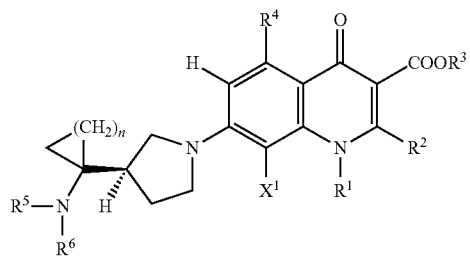

That is, 3-(1-aminocycloalkyl)pyrrolidinyl substituted-6-hydrogen-substituted-quinolone carboxylic acids, represented by formula (I), its salts, and hydrates thereof (especially compounds having the structure where the 3-position of the above pyrrolidine ring is R-configuration, its salts, and hydrates thereof) exhibit potent antibacterial activity against a wide range of gram-negative bacteria and gram-positive bacteria, and in particular, a characteristic of these compounds of this invention is that they exhibit potent antibacterial activity against resistant bacteria as represented by gram-positive cocci, including MRSA, PRSP, and VRE. In addition, the characteristics of the compounds of this invention are that they exhibit excellent safety and good pharmacokinetics that enable the compounds to be used in clinical situations, which could not be achieved with compounds prior to this invention even if they had substituents of the same structures.

Such excellent properties of the compounds of this invention are exhibited by compounds in which the n in the above-described substituent is an integer of 1 or 2, and the excellent effects are seen especially with compounds for which n is an integer 1. That is, compounds wherein the cyclic part is a tricyclic ring are preferable compounds.

In the case where a compound of formula (I) of this invention has a structure in which diastereomers are present, a compound comprised of a single diastereomer is preferably administered when the compound of this invention is administered to human or animals. The term, "comprised of a single diastereomer" as used herein means not only a case in which it is completely free from the other diastereomer but also a case in which it is in a chemically pure degree. That is, it may be interpreted that the other diastereomer may be contained as long as there are no influences on the physical constants and physiological activities of the compound.

Also, the term "stereochemically pure" as used herein means that, in the case where a compound or the like exists in a plurality of isomer forms due to the presence of asymmetric carbon atoms, the compound is comprised of only one of them. The term "pure" in this case can also be considered in the same manner as described above.

Though the quinolone carboxylic acid derivative of this invention may be used either in its free form or as an acid addition salt or a salt of its carboxyl group. Examples of the acid addition salt include inorganic acid salts, such as hydrochlorides, sulfates, nitrates, hydrobromides, hydroiodides, phosphates, etc.; and organic acid salts, such as methanesulfonates, benzenesulfonates, toluenesulfonates (and other sulfonates), acetates, citrates, maleates, fumarates, lactates (and other carboxylates), etc.

Examples of salts of the carboxyl group include alkali metal salts, such as lithium salts, sodium salts, potassium salts, etc.; alkaline earth metal salts, such as magnesium salts, calcium salts, etc.; ammonium salts, triethylamine salts, N-methylglucamine salts, tris-(hydroxymethyl)aminomethane salts; etc., and these could either be inorganic salts or organic salts.

Also, these free form, acid addition salts and salts of carboxyl group of the quinolone carboxylic acid derivative may be present as hydrates.

Though in the case where a compound of this invention is used for antibacterial purposes, a carboxylic acid compound wherein the substituent $R^3$ is a hydrogen atom is preferably used, a quinolone derivative whose carboxylic acid moiety is an ester is useful as a synthesis intermediate or a prodrug. For example, alkyl esters, benzyl esters, alkoxyalkyl esters, phenylalkyl esters, and phenyl esters are useful as synthesis intermediates.

Also, the ester to be used as a prodrug is an ester which is easily hydrolyzed in the living body and form free form of carboxylic acid, and its examples include oxoalkyl esters, such as acetoxymethyl ester, pivaloyloxymethyl ester, ethoxycarbonyl ester, choline ester, dimethylaminoethyl ester, 5-indanyl ester, phthalidinyl ester, 5-alkyl-2-oxo-1,3-dioxole-4-ylmethyl esters, and 3-acetoxy-2-oxobutyl ester.

Further, a quinolone derivative, wherein one of either of the substituents $R^5$ and $R^6$ is a hydrogen atom and the other is a substituted carboxyl group derived from an amino acid, a dipeptide, or a tripeptide, is useful as a prodrug.

An amino acid, a dipeptide, or a tripeptide to be used for obtaining such a prodrug is one wherein the peptide bond, which is formed by the carboxyl group derived from the amino acid, dipeptide, or tripeptide and the amino group that exists on the substituent at the 7-position of the quinolone carboxylic acid derivative, can be easily hydrolyzed in the living body and form free form of amine, and its examples include those derived from glycine, alanine, aspartic acid, and other amino acids, glycine-glycine, glycine-alanine, alanine-alanine, and other dipeptides, and glycine-glycine-alanine, glycine-alanine-alanine, and other tripeptides.

The compound of this invention represented by the formula (I) can be produced by various methods, and in a preferred example, such a compound can be produced for example by reacting a compound represented by formula (III):

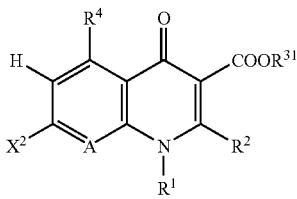

[wherein $X^2$ represents a substituent which functions as a leaving group, such as a substituted or unsubstituted phenylsulfonyl group, a substituted or unsubstituted alkyl sulfonyl group having 1 to 3 carbon atoms, a fluorine atom, a chlorine atom or a bromine atom;

$R^{31}$ is the $R^3$ defined in the formula (I) or a boron-containing group represented by formula (IV):

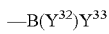

(wherein $Y^{32}$ and $Y^{33}$ may be the same or different from each other with each being a fluorine atom or an alkylcarbonyloxy group having 2 to 4 carbon atoms); and $R^1$, $R^2$, $R^4$, $R^5$, $R^6$, and A are as defined in the formula (I)] with a compound of the following formula (V) or an addition salt thereof:

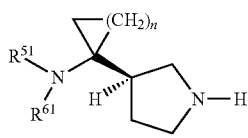

[wherein each of $R^{51}$ and $R^{61}$ independently represents a hydrogen atom, an alkyl group having 1 to 6 carbon atoms or a protective group for an amino group, or one of either $R^{51}$ or $R^{61}$ represents a hydrogen atom and the other represents a substituted carboxyl group derived from an amino acid, a dipeptide, or a tripeptide with an amino group that is unsubstituted or is protected by a protective group for an amino group, and this alkyl group may have a substituent selected from the group consisting of an alkylthio group having 1 to 6 carbon atoms, an alkoxy group having 1 to 6 carbon atoms, a hydroxyl group, and a halogen atom, and n is the same as defined in the formula (I)]

(in the case where an addition salt is used, the reaction is carried out under the presence of reagents that cause the addition salt to become a free form).

Examples of the acid addition salts include inorganic acid salts, such as hydrochlorides, sulfates, nitrates, hydrobromides, hydroiodides, phosphates, etc.; and organic acid salts, such as methanesulfonates, benzenesulfonates, toluenesulfonates (and other sulfonates), acetates, citrates, maleates, fumarates, lactates (and other carboxylates); etc.

The reaction may be carried out using a solvent or without using a solvent. A solvent to be used in the reaction may be any solvent which have no an adverse effect on the reaction, and its examples include dimethyl sulfoxide, pyridine, acetonitrile, ethanol, chloroform, dimethylformamide, dimethylacetamide, N-methylpyrrolidone, tetrahydrofuran, water, 3-methoxybutanol, or a mixture of thereof.

The reaction is preferably carried out under the presence of an acid receptor, such as an inorganic base or an organic base, for example, an inorganic basic compound, such as a carbonate or bicarbonate of an alkaline metal or an alkaline earth metal, or an organic basic compound, such as triethylamine, pyridine, 1,8-diazobicycloundecene, N-methyl piperidene, N,N-diisopropylethylamine, etc.

The reaction temperature should normally be in the temperature range of room temperature to 200° C. and preferably in the range of 25 to 150° C. The reaction time should be in the range of 30 minutes to 48 hours, and the reaction is normally completed in approximately 30 minutes to 8 hours.

The protective group of an amino group may be any protective group that is generally used in the relevant field, and its examples include alkoxycarbonyl groups, which may have a substituent, such as tert-butoxycarbonyl group, 2,2,2-trichloroethoxycarbonyl group, etc.; aralkyloxycarbonyl groups, which may have a substituent, such as benzyloxycarbonyl group, para-methoxybenzyloxycarbonyl group, para-nitrobenzyloxycarbonyl group, etc.; acyl groups, which may have a substituent, such as acetyl group, methoxyacetyl group, trifluoroacetyl group, chloroacetyl group, pivaloyl group, formyl group, benzoyl group, etc.; alkyl groups, which may have a substituent, and aralkyl groups, which may have a substituent, such as tert-butyl group, benzyl group, para-nitrobenzyl group, para-methoxybenzyl group, triphenylmethyl group, etc.; ethers, which may have a substituent, such as methoxymethyl group, tert-butoxymethyl group, tetrahydropyranyl group, 2,2,2-trichloroethoxymethyl group, etc.; and substituted silyl groups, such as trimethylsilyl group, isopropyldimethylsilyl group, tert-butyldimethylsilyl group, tribenzylsilyl group, tert-butyldiphenylsilyl group, etc.

In the case where each of $R^3$ and $R^{31}$ is an alkyl group having from 1 to 6 carbon atoms, an alkoxymethyl group having from 2 to 7 carbon atoms or a phenylalkyl group (aralkyl group) composed of an alkylene group having 1 to 6 carbon atoms and a phenyl group, it can be converted into a corresponding carboxylic acid by treatment under acidic or basic conditions which are generally used for the hydrolysis of carboxylic acid esters.

In the case where $R^{31}$ has a structure of the formula (IV), it can be converted into a corresponding carboxylic acid by subjecting it to hydrolysis under acidic or basic conditions after allowing the compound (V) to react with the compound (III).

In the case where deprotection is necessary, the compound of interest represented by the formula (I) can be obtained by removing the protective group under appropriate conditions suitable for the protective group.

A compound of the formula (V) may be produced by various methods, and though a method shown in PCT/JP96/00208 may be given as an example, the method of production is not limited to thereto.

A compound of the formula (V) can be produced by removing Q from a compound represented by the following formula (VI):

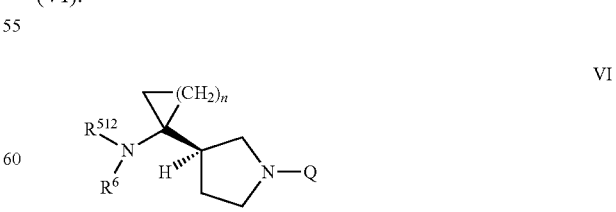

[In the above formula (VI), $R^{512}$ is the same as the $R^5$ defined in the formula (I) or represents a protective group of an amino group, $R^6$ and n are the same as defined in the formula (I), Q is a protective group of an amino group, wherein the protective group of an amino group may be selected from the group consisting of a (substituted) alkoxycarbonyl group, a (substituted) aralkyloxycarbonyl group, a (substituted) acyl group, a (substituted) alkyl group, a (substituted) aralkyl group and a substituted silyl group.]

An above-described compound may be present in the form of a salt thereof, a hydrate thereof, or a hydrate of the salt. Examples of the acid addition salt include inorganic acid salts and organic acid salts. Specific examples thereof include inorganic acid salts, such as hydrochlorides, sulfates, hydrobromides, hydroiodides, phosphates, etc.; and organic acid salts, such as methanesulfonates, benzenesulfonates, toluenesulfonates (sulfonic acid salts); acetates, citrates, maleates, fumarates, lactates (carboxylic acid salts); etc.

When both $R^{512}$ and Q are protective groups of an amino group, they may be the same or different from each other. However, it is more favorable for the production of compound (I) that each is cut off under different reaction conditions.

Examples of $R^{512}$ and Q, which are protective groups of amino groups, include the following. That is, example thereof include a (substituted) alkoxycarbonyl group, a (substituted) aralkyloxycarbonyl group, a (substituted) acyl group, a (substituted) alkyl group, a (substituted) aralkyl group, and a (substituted) silyl group.

Specific examples thereof include (substituted) alkoxycarbonyl groups, such as tert-butoxycarbonyl group, 2,2,2-trichloroethoxycarbonyl group, etc.; (substituted) aralkyloxycarbonyl groups, such as benzyloxycarbonyl group, para-methoxybenzyloxycarbonyl group, para-nitrobenzyloxycarbonyl group, etc.; (substituted) acyl groups, such as acetyl group, methoxyacetyl group, trifluoroacetyl group, chloroacetyl group, pivaloyl group, formyl group, benzoyl group, etc.; (substituted) alkyl groups or (substituted) aralkyl groups, such as tert-butyl group, benzyl group, para-nitrobenzyl group, para-methoxybenzyl group, triphenylmethyl group, etc.; (substituted) ethers, such as methoxymethyl group, tert-butoxymethyl group, tetrahydropyranyl group, 2,2,2-trichloroethoxymethyl group, etc.; and substituted silyl groups, such as trimethylsilyl group, isopropyldimethylsilyl group, tert-butyldimethylsilyl group, tribenzylsilyl group, tert-butyldiphenylsilyl group, etc.

In producing the compound (I) using an abovementioned compound having Q as a protective group, it is necessary to carry out the reaction by removing the protective group Q. In this case, its reaction with the compound (III) or (V) may be carried out by a so-called one-pot reaction or the reaction may be carried out after once isolating the compound (V) by removing the protective group.

As with a compound of the formula (V), a compound of the formula (VI) can be produced by various methods, and though a method described in PCT/JP96/00208 may be given as an example, the production method is not limited thereto.

Cis-2-fluorocyclopropylamine comprised of a single isomer, which is desirable for the synthesis of a compound of the formula (I) comprised of a single isomer, may synthesized for example by the method described in JP-A-2-231475 (the term "JP-A" as used herein means an unexamined published Japanese patent application"). Synthesis of the compound of formula (I) comprised of a single isomer using an optically active cis-2-fluorocyclopropylamine derivative obtained in the manner described above as a raw material, may be carried out for example in accordance with the method described for example in JP-A-2-231475.

Specific examples of compounds of this invention include the following:

7-[3-(R)-(1-aminocyclopropyl)pyrrolidin-1-yl]-1-[2-(S)-fluoro-1-(R)-cyclopropyl]-1,4-dihydro-4-oxo-1,8-naphthyridine-3-carboxylic acid [shown in the following formula];

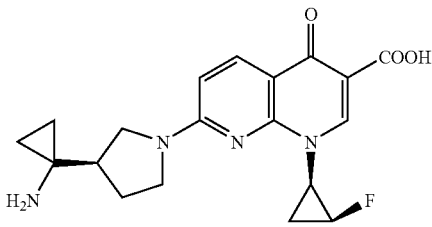

7-[3-(R)-(1-aminocyclopropyl)pyrrolidin-1-yl]-1-[2-(S)-fluoro-1-(R)-cyclopropyl]-1,4-dihydro-4-oxoquinoline-3-carboxylic acid [shown in the following formula];

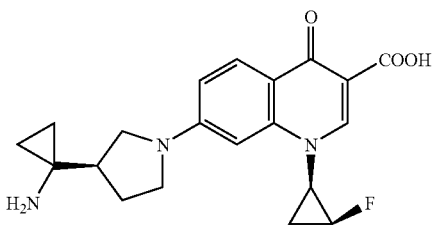

7-[3-(R)-(1-aminocyclopropyl)pyrrolidin-1-yl]-1-[2-(S)-fluoro-1-(R)-cyclopropyl]-8-chloro-1,4-dihydro-4-oxo-quinoline-3-carboxylic acid [shown in the following formula];

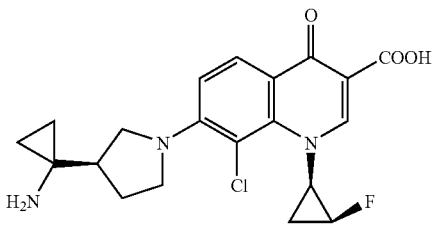

7-[3-(R)-(1-aminocyclopropyl)pyrrolidin-1-yl]-1-[2-(S)-fluoro-1-(R)-cyclopropyl]-8-fluoro-1,4-dihydro-4-oxo-quinoline-3-carboxylic acid [shown in the following formula];

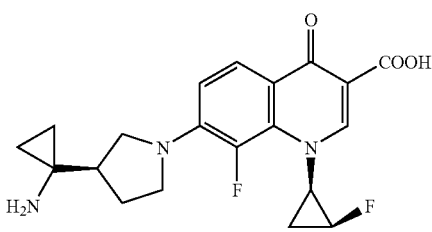

7-[3-(R)-(1-aminocyclopropyl)pyrrolidin-1-yl]-1-[2-(S)-fluoro-1-(R)-cyclopropyl]-8-difluoromethoxy-1,4-dihydro-4-oxoquinoline-3-carboxylic acid [shown in the following formula];

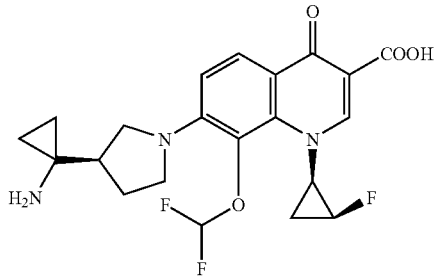

7-[3-(R)-(1-aminocyclopropyl)pyrrolidin-1-yl]-1-[2-(S)-fluoro-1-(R)-cyclopropyl]-1,4-dihydro-8-methoxy-4-oxo-quinoline-3-carboxylic acid [shown in the following formula];

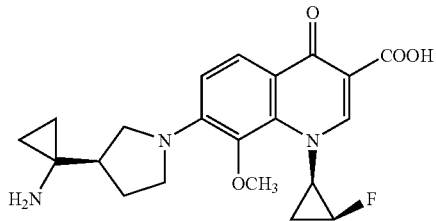

7-[3-(R)-(1-aminocyclopropyl)-pyrrolidin-1-yl]-1-[2-(S)-fluoro-1-(R)-cyclopropyl]-1,4-dihydro-8-methyl-4-oxo-quinoline-3-carboxylic acid [shown in the following formula];

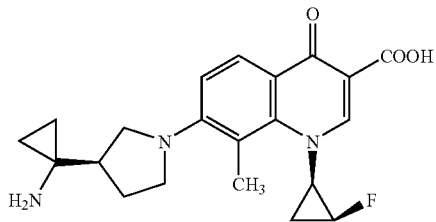

5-amino-7-[3-(R)-(1-aminocyclopropyl)pyrrolidin-1-yl]-1-[2-(S)-fluoro-1-(R)-cyclopropyl]-1,4-dihydro-8-fluoro-4-oxoquinoline-3-carboxylic acid [shown in the following formula];

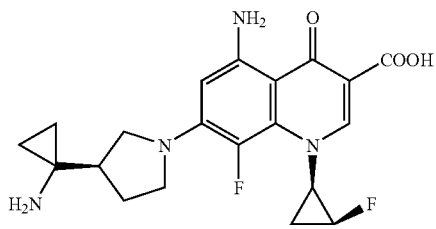

5-amino-7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid [shown in the following formula];

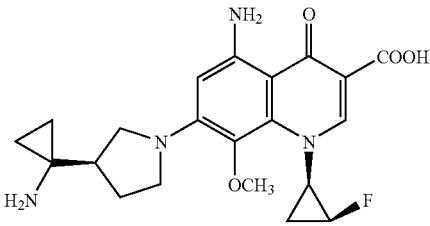

5-amino-7-[3-(R)-(1-aminocyclopropyl)pyrrolidin-1-yl]-1-[2-(S)-fluoro-1-(R)-cyclopropyl]-1,4-dihydro-8-methyl-4-oxoquinoline-3-carboxylic acid [shown in the following formula];

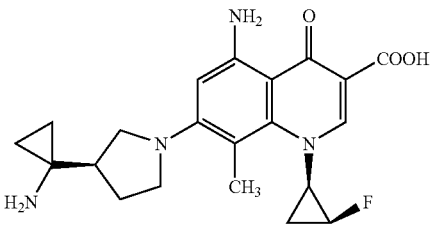

10-[3-(R)-(1-aminocyclopropyl)pyrrolidin-1-yl]-2,3-dihydro-3-(S)-methyl-7-oxo-7H-pyrido[1,2,3-de][1,4]benzoxazine-6-carboxylic acid [shown in the following formula];

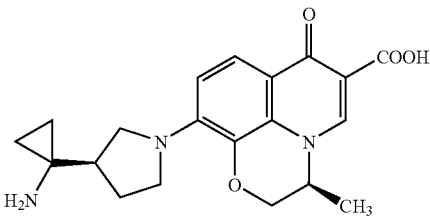

7-[3-(R)-(1-aminocyclobutyl)pyrrolidin-1-yl]-1-[2-(S)-fluoro-1-(R)-cyclopropyl]-8-difluoromethoxy-1,4-dihydro-4-oxoquinoline-3-carboxylic acid [shown in the following formula];

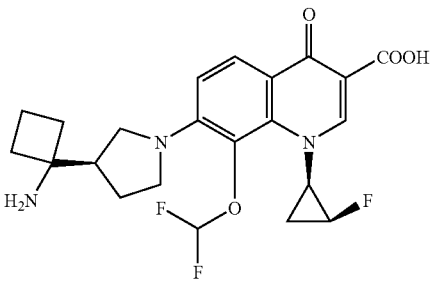

7-[3-(R)-(1-aminocyclobutyl)pyrrolidin-1-yl]-1-[2-(S)-fluoro-1-(R)-cyclopropyl]-1,4-dihydro-8-methoxy-4-oxo-quinoline-3-carboxylic acid [shown in the following formula];

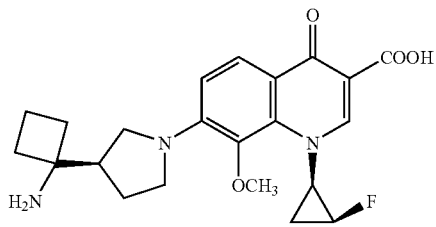

7-[3-(R)-(1-aminocyclobutyl)pyrrolidin-1-yl]-1-[2-(S)-fluoro-1-(R)-cyclopropyl]-1,4-dihydro-8-methyl-4-oxo-quinoline-3-carboxylic acid [shown in the following formula];

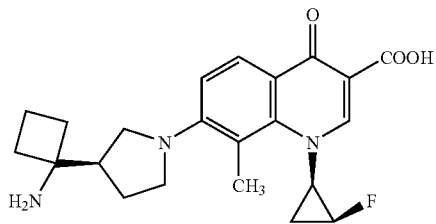

7-[3-(R)-[1-(methylamino)cyclopropyl]pyrrolidin-1-yl]-1-[2-(S)-fluoro-1-(R)-cyclopropyl]-1,4-dihydro-8-methoxy-4-oxoquinoline-3-carboxylic acid [shown in the following formula];

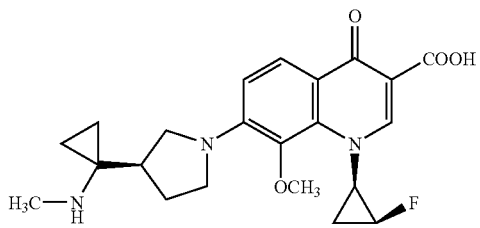

7-[3-(R)-[1-(methylamino)cyclopropyl]pyrrolidin-1-yl]-1-[2-(S)-fluoro-1-(R)-cyclopropyl]-1,4-dihydro-8-methyl-4-oxoquinoline-3-carboxylic acid [shown in the following formula];

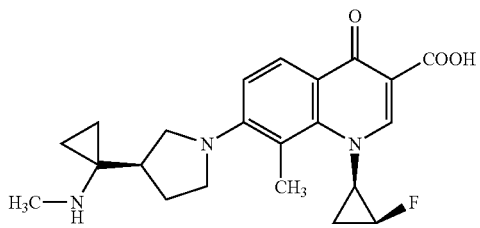

7-[3-(R)-[1-(ethylamino)cyclopropyl]pyrrolidin-1-yl]-1-[2-(S)-fluoro-1-(R)-cyclopropyl]-1,4-dihydro-8-methyl-4-oxoquinoline-3-carboxylic acid [shown in the following formula];

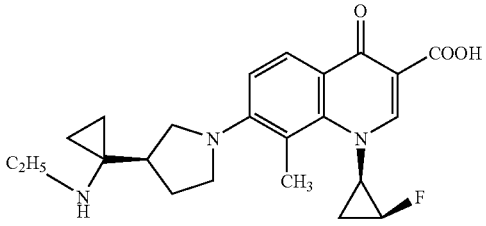

5-amino-7-[3-(R)-[1-(methylamino)cyclopropyl]pyrrolidin-1-yl]-1-[2-(S)-fluoro-1-(R)-cyclopropyl]-1,4-dihydro-8-methyl-4-oxoquinoline-3-carboxylic acid [shown in the following formula];

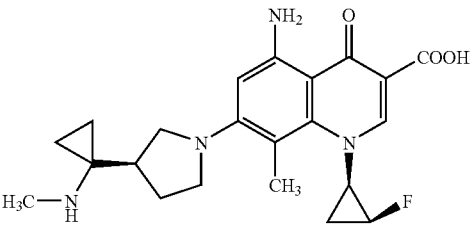

10-[3-(R)-[1-(methylamino)cyclopropyl]pyrrolidin-1-yl]-2,3-dihydro-3-(S)-methyl-7-oxo-7H-pyrido[1,2,3-de][1,4]benzoxazine-6-carboxylic acid [shown in the following formula];

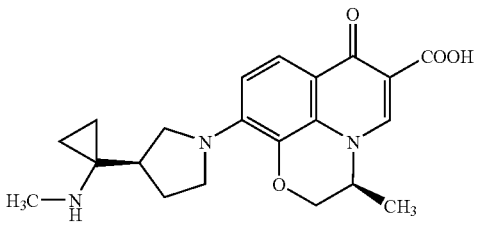

1-(cyclopropyl)-8-methyl-7-[3-(R)-[1-(methylamino)cyclopropyl]pyrrolidin-1-yl]-1,4-dihydro-4-oxoquinoline-3-carboxylic acid [shown in the following formula];

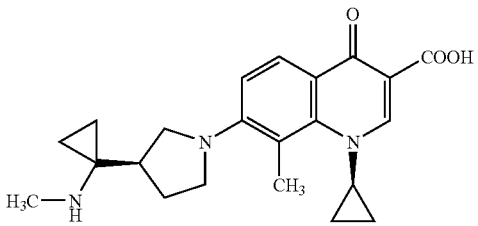

Since the compound of this invention has potent antibacterial actions, it can be used as medicaments for use in human bodies, animals, and fishes or as preservatives of agricultural chemicals and food.

In the case where the compound of this invention is used as a medicament for human bodies, its dose is within the range of from 50 mg to 1 g, preferably from 100 mg to 500 mg, per day per adult.

In the case of use as a medical drug for an animal, its dose varies depending on the purpose of its administration (treatment or prevention), kind and size of each animal to be treated, kind and degree of each infected pathogenic bacterium, but is within the range of generally from 1 mg to 200 mg, preferably from 5 mg to 100 mg, per 1 kg body weight of each animal as a daily dose.

The daily dose is administered once a day or by dividing it into two to four doses per day. As occasion demands, the daily dose may exceed the abovementioned amounts.

Since the compounds of this invention are active against a broad range of microorganisms which cause various infectious diseases, it can treat, prevent or alleviate diseases caused by such pathogens.

Examples of bacteria and bacterioid microorganisms on which the compounds of this invention are effective include the genus *Staphylococcus, Streptococcus pyogenes, hemolytic streptococcus, enterococcus, pneumococcus*, the genus *Peptostreptococcus, Neisseria gonorrhoeae, Escherichia coli*, the genera *Citrobacter*, the genus *Shigella, Klebsiella pneumoniae*, the genera *Enterobacter*, the genus *Serratia*, the genus *Proteus, Pseudomonas aeruginosa, Haemophilus influenzae*, the genus *Acinetobacter*, the genus *Campylobacter, Chlamydia trachomatis*, and the like.

Examples of the diseases caused by the above pathogens include folliculitis, furuncle, carbuncle, erysipelas, phlegmon, lymphangitis (lymphadenitis), panaritium, subcutaneous abscess, hidrosadenitis, aggregated acne, infectious atheroma, anal abscess, mastitis, superficial secondary infections of traumatic wounds, burn wounds, operative wounds, etc., pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, inflammation of the uterine appendages, intrauterine infection, bartholinitis, blepharitis, hordeolum, dacryocystitis, tarsadenitis, corneal ulcer, otitis medea, sinusitis, periodontitis, pericoronitis, jaw inflammation, peritonitis, endocarditis, sepsis, meningitis, skin infection, etc.

Further, examples of acid-fast bacteria on which the compounds of this invention are effective include tubercle bacilli [*Mycobacterium* (abbreviated as "M." hereinafter) tuberculosis, *M. bovis, M. africanum*], atypical acid-fast bacteria [*M. kansasii, M. marinum, M. scrofulaceum, M. avium, M. intracellulare, M. xenopi, M. fortuitum, M. chelonae*], etc.

The acid-fast bacteria infections that are caused by these pathogens are largely classified according to the causing bacteria into the three types of tuberculosis, atypical acid-fast bacteria infection, and leprosy. In addition to the lungs, tubercle bacilli infections may be seen in the thoracic cavity, trachea/bronchus, lymph nodes, in a generally disseminated manner, in the bones and joints, meninges/brain, digestive organs (intestines, liver), skin, mammary glands, eyes, middle ear/throat, urinary tract, male genitals, female genitals, etc. The lungs are the main affected parts of atypical acid-fast bacteria infections (non-tubercle acid-fast bacteria infections), and other examples of atypical acid-fast bacteria infections include local lymphadenitis, soft skin tissue infections, articular infections, general dissemination type infections, etc.

The compounds of this invention are also effective against various microorganisms that cause infections in animals. Examples of such microorganisms include *Escherichia, Salmonella, Pasturella, Haemophilus, Bordetella, Staphylococcus, Mycoplasma*, etc.

Specific examples of fowl diseases include escherichiosis, pullorum disease, fowl paratyphoid fever, fowl cholera, infectious coryza, staphylococcal infection, Mycoplasma infection, etc., specific examples of pig diseases include escherichiosis, salmonellosis, pasturellosis, Haemophilis infection, atrophic rhinitis, exudative epidermitis, Mycoplasma infection, etc., specific examples of cattle diseases include escherichiosis, salmonellosis, hemorrhagic septicemia, Mycoplasma infection, contagious bovine pleuropneumonia, mastitis, etc., specific examples of dog diseases include coliemia, *Salmonella* infection, hemorrhagic septicemia, pyometra, cystitis, etc., and specific examples of cat diseases include exudative pleurisy, cystitis, chronic rhinitis, Haemophilus infection, kitten diarrhea, Mycoplasma infection, etc.

An antibacterial preparation which comprises the compound of this invention can be prepared by selecting an appropriate pharmaceutical preparation in accordance to the method of administration and using any of the generally used methods of preparing various pharmaceutical preparations. With regard to the dosage forms of antibacterial preparations having the compound of this invention as its principle agent, tablets, powders, granules, capsules, solutions, syrups, elixirs, oily or aqueous suspensions, etc. can be given as examples of forms of oral pharmaceutical preparations.

In the case of injections, a stabilizing agent, an antiseptic agent, a solubilizing agent, etc. may be used in the preparation, or a solution which may contain these auxiliary agents may be contained in a container and thereafter made into a solid preparation by freeze-drying or the like means to be re-dissolved when used. Also, a single dose may be contained in a single container or multiple doses may be contained in the same container.

Examples of forms of external-use preparations include solutions, suspensions, emulsions, ointments, gels, creams, lotions, sprays, etc.

A solid preparation may contain pharmaceutically acceptable additives together with the active compound. For example, fillers, extenders, binders, disintegrators, solubilization enhancing agents, moistening agents, lubricating agents, etc. may be selected and mixed as necessary to form a preparation.

Examples of forms of liquid preparations include solutions, suspensions, emulsions, and these may contain suspending agents, emulsifying agents, etc. as additives.

Examples of methods of administering the compound of this invention to an animal include a method of direct oral administration or oral administration by mixing it with feed, a method of preparing a solution and then performing oral administration of the solution directly or upon addition of the solution to drinking water or feed, a method of injection administration, etc.

A pharmaceutical preparation for administering the compound of this invention to an animal can be prepared optionally as powders, fine granules, soluble powders, syrups, solutions, or injections by the techniques generally used in the relevant field.

Formulation examples of pharmaceutical preparations are shown below.

Formulation Example 1 (Capsule):

| | |
|---|---|
| Compound of Example 1 | 100.0 mg |
| Corn starch | 23.0 mg |
| CMC calcium | 22.5 mg |
| Hydroxymethyl cellulose | 3.0 mg |
| Magnesium stearate | 1.5 mg |
| Total | 150.0 mg |

Formulation Example 2 (Solution):

| | |
|---|---|
| Compound of Example 1 | 1 to 10 g |
| Acetic acid or sodium hydroxide | 0.5 to 2 g |
| Ethyl para-hydroxybenzoate | 0.1 g |
| Purified water | 88.9 to 98.4 g |
| Total | 100 g |

Formulation Example 3 (Powder to be mixed in feed):

| | |
|---|---|
| Compound of Example 1 | 1 to 10 g |
| Corn starch | 98.5 to 89.5 g |
| Light silicic anhydride | 0.5 g |
| Total | 100 g |

BEST MODE OF CARRYING OUT THE INVENTION

The following describes the invention-based on examples and reference examples, though this invention is not limited to thereto.

Reference Example 1

Ethyl 2-(2,4-difluoro-3-methylbenzoyl)-3-dimethylaminoacrylate 2,4-Difluoro-3-methylbenzoate (4.97 g, 28.9 mmol) was dissolved in toluene (50 ml), and after adding N,N-dimethylformamide (0.1 ml) and thionyl chloride (3.16 ml, 43.4 mmol) thereto, it was stirred for 14 hours in an oil bath of 80° C. The reaction solution was then cooled and thereafter concentrated under a reduced pressure. After adding toluene to the residue and repeating concentration under a reduced pressure, the residue obtained was dissolved in tetrahydrofuran (10 ml). This solution was added dropwise while cooling with ice to a solution in which ethyl 3-dimethylaminoacrylate (4.97 g, 34.7 mmol) and triethylamine (5.04 ml, 36.1 mmol) were dissolved in tetrahydrofuran (20 ml). After completion of dripping, the reaction solution was heated under reflux for 10 hours. After completion of the reaction, the reaction solution was filtered, the triethylamine hydrochloride salt was removed (by diethyl ether washing), and the filtrate was concentrated under a reduced pressure. The residue obtained was applied to a short silica gel chromatography and 6.70 g (78%) of the title compound was obtained in the form of a yellow powder from an n-hexane:ethyl acetate=1:1 eluate.

$^1$H-NMR (400 MHz, CDCl$_3$) δ: 0.95 (3H, t, J=7.08 Hz), 2.18 (3H, t, J=1.95 Hz), 2.92-3.24 (6H, m), 3.99 (2H, q, J=7.08 Hz), 6.86 (1H, dt, J=1.22, 8.55 Hz), 7.43 (1H, brs), 7.75 (1H, s). IR (KBr, disk): 3055, 2985, 2933, 2875, 2814, 1942, 1693, 1630, 1593, 1477, 1431, 1379, 1277, 1255, 1221 cm$^{-1}$.

Melting point: 82 to 84° C. Elemental analysis: As C$_{15}$H$_{17}$F$_2$NO$_3$; Calcd.: C, 60.60; H, 5.76; N, 4.71. Found: C, 60.31; H, 5.73; N, 4.73.

Reference Example 2

Ethyl 7-fluoro-1-[2-(S)-fluoro-1-(R)-cyclopropyl]-1,4-dihydro-8-methyl-4-oxoquinoline-3-carboxylate Ethyl 2-(2,4-fluoro-3-methylbenzoyl)-3-dimethylaminoacrylate (1.06 g, 3.57 mmol) was dissolved in tetrahydrofuran (15 ml), and after adding the para-toluenesulfonic acid salt of (1R,2S)-2-fluorocyclopropylamine (970 mg, 3.93 mmol), a solution, in which triethylamine (552 μl, 3.96 mmol) was dissolved in tetrahydrofuran (5 ml), was added dropwise under stirring at −15° C. After stirring the reaction solution for 2 hours at room temperature, potassium carbonate (740 mg, 5.36 mmol) and tetrabutylammonium chloride (49.6 mg, 0.179 mmol) were added, and this reaction suspension was heated under reflux while stirring for 5 days. After cooling the reaction solution, the tetrahydrofuran was evaporated under a reduced pressure. Dichloromethane (10 ml) was then added to the residue, and while cooling with ice and stirring, 2 mol/l hydrochloric acid was added dropwise gradually to adjust the pH to approximately 3. Then after stirring for 15 minutes at room temperature, extraction with dichloromethane (60 ml×3) was performed. After drying over anhydrous sodium sulfate, filtration was performed, the filtrate was concentrated under a reduced pressure, and the crude crystals obtained were stirred and purified in the slurry state in ethyl acetate. 713 mg (65%) of the title compound was thereby obtained in the form of colorless crystals.

$^1$H-NMR (400 MHz, CDCl$_3$) δ: 1.41 (3H, t, J=7.08 Hz), 1.56-1.62 (2H, m), 2.66 (3H, d, J=2.69 Hz), 3.85-3.89 (1H, m), 4.39 (2H, q, J=7.08 Hz), 4.78-4.79 and 4.94-4.95 (1H, dm, J=62.74 Hz), 7.13 (1H, t, J=8.91 Hz), 8.36 (1H, dd, J=6.71, 8.91 Hz), 8.56 (1H, d, J=2.93 Hz). IR (KBr, disk): 3438, 3097, 2983, 2939, 2902, 1907, 1720, 1630, 1593, 1566, 1460, 1429, 1387, 1367, 1311, 1250 cm$^{-1}$.

Melting point: 187 to 188° C. Elemental analysis: As C$_{16}$H$_{15}$F$_2$NO$_3$; Calcd.: C, 62.54; H, 4.92; N, 4.56. Found: C, 62.41; H, 4.87; N, 4.53.

Reference Example 3

7-fluoro-1-[2-(S)-fluoro-1-(R)-cyclopropyl]-1,4-dihydro-8-methyl-4-oxoquinoline-3-carboxylic acid Ethyl 7-fluoro-1-[2-(S)-fluoro-1-(R)-cyclopropyl]-1,4-dihydro-8-methyl-4-oxoquinoline-3-carboxylate (1.40 g, 4.56 mmol) was dissolved in acetic acid (4 ml), and after adding concentrated hydrochloric acid (4 ml) thereto, it was heated under reflux for 3 hours. After cooling, the reaction solution was poured into ice water (50 ml) and the precipitated crystals were filtered out. After washing the filtered-out crystals with an excess amount of water, washing in cold ethanol and washing in diethyl ether were performed in that order, and after drying under a reduced pressure, 1.18 g (93%) of the title compound was obtained in the form of a white powder.

$^1$H-NMR (400 MHz, CDCl$_3$) δ: 1.48-1.72 (2H, m), 2.75 (3H, t, J=2.56 Hz), 4.01 (1H, dd, J=2.81, 5.25 Hz), 4.83-4.84 and 4.98-5.00 (1H, dm, J=62.74 Hz), 7.31 (1H, dd, J=2.20, 8.79 Hz), 8.40-8.44 (1H, m), 8.84 (1H, d, J=2.69 Hz), 14.50

(1H, brs). IR (KBr, disk): 3097, 3014, 2956, 2642, 1957, 1728, 1618, 1566, 1508, 1469, 1435, 1389, 1321, 1254, 1200 cm$^{-1}$.

Melting point: 250 to 253° C. $[\alpha]_D^{24.3}$=−50.00° (c 0.145, 0.1 mol/l NaOH) Elemental analysis: As $C_{14}H_{11}F_2NO_3$; Calcd.: C, 60.22; H, 3.97; N, 5.02. Found: C, 59.92; H, 3.98; N, 4.92.

Example 1

7-[3-(R)-(1-aminocyclopropyl)pyrrolidin-1-yl]-1-[2-(S)-fluoro-1-(R)-cyclopropyl]-1,4-dihydro-8-methyl-4-oxoquinoline-3-carboxylic acid After adding 3-(R)-[1-tert-butoxycarbonylaminocyclopropyl]pyrrolidine (185 mg, 817 μmol) and triethylamine (0.50 ml) to dried dimethyl sulfoxide (2 ml), 7-fluoro-1-[2-(S)-fluoro-1-(R)-cyclopropyl]-1,4-dihydro-8-methyl-4-oxoquinoline-3-carboxylic acid (190 mg, 68 μmol) was added thereto and it was heated under reflux for 17 hours under a nitrogen atmosphere. After concentrating the reaction solution under a reduced pressure, the residue was dissolved in chloroform (50 ml). After washing the organic layer with a 10% aqueous citric acid solution (25 ml), the organic layer was dried over anhydrous sodium sulfate. After filtering, the filtrate was concentrated under a reduced pressure, and after adding dropwise concentrated hydrochloric acid (5 ml) to the residue while cooling with ice, stirring at room temperature was performed for 30 minutes. 1 mol/l Hydrochloric acid (5 ml) was then added to the reaction solution, and after washing the yellow acidic aqueous solution with chloroform (20 ml×3), the pH was adjusted to 12.0 with an aqueous sodium hydroxide solution and the insolubles were removed by filtration. After adjusting the pH of the basic aqueous solution to 7.4 using 1 mol/l hydrochloric acid, extraction with chloroform (100 ml×4) was performed. After drying over anhydrous sodium sulfate, the solvent was evaporated under a reduced pressure. The residue thus obtained was purified by preparative chromatography (development at the lower layer of a 7:3:1 mixture of chloroform:methanol:water), recrystallized in ethanol, and dried under a reduced pressure. 112 mg (43%) of the title compound was thereby obtained in the form of yellow crystals.

$^1$H-NMR (400 MHz, 0.1 mol/l NaOD) δ: 0.54 (4H, d, J=5.61 Hz), 1.19-1.21 (1H, m), 1.58-1.62 (1H, m), 1.66-1.69 (1H, m), 2.00-2.01 (1H, m), 2.16-2.17 (1H, m), 2.35 (3H, s), 3.16-3.23 (2H, m), 3.37-3.42 (1H, m), 3.54-3.55 (1H, m), 4.04-4.05 (1H, m), 4.94-4.95 and 5.10-5.11 (1H, dm, J=62.16 Hz), 7.01 (1H, d, J=8.78 Hz), 7.95 (1H, d, J=8.78 Hz), 8.43 (1H, s). IR (KBr, disk): 3375, 3062, 3006, 2925, 2864, 1728, 1610, 1508, 1475, 1431, 1394, 1348, 1315, 1257 cm$^{-1}$.

Melting point: 228 to 230° C. $[\alpha]_D^{24.7}$=−235.09° (c 0.285, 0.1 mol/l NaOH) Elemental analysis: As $C_{21}H_{24}FN_3O_3$; Calcd.: C, 65.44; H, 6.28; N, 10.90. Found: C, 65.10; H, 6.32; N, 10.76.

Reference Example 4

Ethyl 7-fluoro-1-[2-(S)-fluoro-1-(R)-cyclopropyl]-1,4-dihydro-8-methoxy-4-oxoquinoline-3-carboxylate A mixture of ethyl (2,4-difluoro-3-methoxy)benzoyl acetate (48.8 g, 189 mmol), synthesized by the method described in PCT/US98/19138, triethyl orthoformate (78.6 ml, 472 mmol) and acetic anhydride (250 ml) was stirred while heating for 6 hours in an oil bath of an external temperature of 120° C. After letting the reaction solution cool, concentration under a reduced pressure and solidification by drying were performed. The yellow extract obtained was then dissolved in toluene (800 ml), the para-toluenesulfonic acid salt of (1R,2S)-2-fluorocyclopropylamine (60.1 g, 246 mmol) was added, and while stirring at −15° C., a solution, in which triethylamine (40.8 ml, 293 mmol) was dissolved in toluene (200 ml), was added dropwise thereto. After stirring the reaction solution for 4 hours at room temperature, water (500 ml) was added, and the organic layer was separated. After washing the organic layer with saturated saline solution (500 ml×2), it was dried over anhydrous sodium sulfate. After filtering, the filtrate was concentrated under a reduced pressure and dried. The yellow oily substance obtained was then dissolved in 1,4-dioxane (600 ml), and while cooling with water, 60% oily sodium hydride (5.94 g, 242 mmol) was added gradually. After stirring the reaction mixture for 30 minutes at room temperature, concentration under a reduced pressure was performed until the volume of the reaction solution became approximately 300 ml. The concentrate thus obtained was slowly poured into 1 mol/l hydrochloric acid, which was stirred and cooled with water, and the precipitated crystals were filtered out. After washing these crystals with excess purified water, a small amount of ethanol, and excess diethyl ether, in that order, the crude crystals obtained where slurried in ethyl acetate and purified. 49.4 g (80.9%) of the title compound was thereby obtained in the form of colorless crystals.

$^1$H-NMR (400 MHz, CDCl$_3$) δ: 1.42 (3H, t, J=7.08 Hz), 1.55-1.64 (2H, m), 3.88-3.93 (1H, m), 4.04 (3H, d, J=1.96 Hz), 4.39 (2H, q, J=7.08 Hz), 4.78-4.79 and 4.94-4.95 (1H, dm, J=62.61 Hz), 7.22 (1H, t, J=8.79 Hz), 8.24 (1H, dd, J=5.86, 8.79 Hz), 8.60 (1H, s).

Melting point: 190 to 193° C. (decomposed)

Reference Example 5

7-fluoro-1-[2-(S)-fluoro-1-(R)-cyclopropyl]-1,4-dihydro-8-methoxy-4-oxoquinoline-3-carboxylic acid After dissolving ethyl 7-fluoro-1-[2-(S)-fluoro-1-(R)-cyclopropyl]-1,4-dihydro-8-methoxy-4-oxoquinoline-3-carboxylate (34.0 g, 105 mmol) in acetic acid (400 ml) and then adding concentrated hydrochloric acid (400 ml) thereto, it was heated under reflux for 3 hours. After cooling, the reaction solution was poured into ice water (1500 ml), and the precipitated crystals were filtered out. After washing the filtered-out crystals with an excess amount of water, it was washed with cold ethanol and diethyl ether in that order, and after drying under a reduced pressure, the crude crystals obtained were purified by recrystallization from a mixed solvent of acetonitrile-ethanol and then dried under a reduced pressure. 27.1 g (87.4%) of the title compound was there by obtained in the form of a white powder.

$^1$H-NMR (400 MHz, CDCl$_3$) δ: 1.45-1.75 (2H, m), 3.87-3.95 (1H, m), 4.03 (3H, d, J=1.95 Hz), 4.79-4.81 and 4.97-4.99 (1H, dm, J=62.68 Hz), 7.30 (1H, t, J=8.79 Hz), 8.27 (1H, dd, J=5.86, 8.79 Hz), 8.76 (1H, s).

Melting point: 261-263° C. (decomposed)

Example 2

7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid After adding 3-(R)-[1-tert-butoxycarbonylaminocyclopropyl]pyrrolidine (165 mg, 731 μmol) and triethylamine (0.50 ml) to dried dimethyl sulfoxide (2 ml), 7-fluoro-1-[2-(S)-fluoro-1-(R)-cyclopropyl]-1,4-dihydro-8-methoxy-4-oxoquinoline-3-carboxylic acid (180 mg, 609 µmol) was added thereto and it was heated under reflux for 13 hours under a nitrogen atmosphere. After concentrating the reaction solution under reduced pressure, the residue was dissolved in chloroform (100 ml). After washing the organic layer with a 10% aqueous citric acid solution (50 ml), the organic layer was dried over anhydrous sodium sulfate. After filtering, the filtrate was concentrated under a reduced pressure, and after adding dropwise concentrated hydrochloric acid (5 ml) to the residue while cooling with ice, stirring was performed at room temperature for 30 minutes. 1 mol/l Hydrochloric acid (5 ml) was then added to the reaction solution, and after washing the yellow acidic aqueous solution with chloroform (50 ml×4), the pH was adjusted to 12.0 with an aqueous sodium hydroxide solution and the insolubles were removed by filtration. After adjusting the pH of the basic aqueous solution to 7.4 with 1 mol/l hydrochloric acid, extraction with chloroform (100 ml×4) was performed. After drying over anhydrous sodium sulfate, the solvent was evapolated under a reduced pressure. The residue thus obtained was purified by preparative chromatography (development at the lower layer of a 7:3:1 mixture of chloroform methanol:water), recrystallized in isopropyl alcohol, and dried under a reduced pressure. 146 mg (60%) of the title compound was thereby obtained in the form of yellow crystals.

$^1$H-NMR (400 MHz, 0.1 mol/l NaOD) δ: 0.56 (4H, brs), 1.31-1.37 (1H, m), 1.50-1.56 (1H, m), 1.77-1.78 (1H, m), 2.02-2.04 (1H, m), 2.19-2.21 (1H, m), 3.31-3.32 (1H, m), 3.49-3.51 (3H, m), 3.50 (3H, s), 4.00-4.02 (1H, m), 4.93-4.94 and 5.09-5.10 (1H, dm, J=62.87 Hz), 7.01 (1H, s), 7.90 (1H, d, J=9.03 Hz), 8.39 (1H, d, J=3.17 Hz) IR (KBr, disk): 3373, 3315, 3091, 3003, 2976, 2935, 2856, 1903, 1714, 1618, 1518, 1439, 1371, 1313, 1261, 1219 cm$^{-1}$.

Melting point: 189 to 192° C. $[α]_D^{24.7}$=−50.83° (c 0.240, 0.1 mol/l NaOH) Elemental analysis: As $C_{21}H_{24}FN_3O_3$; Calcd.: C, 62.83; H, 6.03; N, 10.47. Found: C, 62.50; H, 6.04; N, 10.26.

Example 3

7-[3-(R)-(1-aminocyclopropyl)pyrrolidin-1-yl]-1-cyclopropyl-1,4-dihydro-8-methyl-4-oxoquinoline-3-carboxylic acid After adding 3-(R)-[1-(tert-butoxycarbonylamino)cyclopropyl]pyrrolidine (132 mg, 585 µmol) and triethylamine (245 µl, 1.76 mmol) to dried dimethyl sulfoxide (1 ml), 1-cyclopropyl-7-fluoro-1,4-dihydro-8-methyl-4-oxoquinoline-3-carboxylic acid $BF_2$ chelate (181 mg, 585 µmol) was added thereto and it was stirred at room temperature for 87 hours under a nitrogen atmosphere. After adding cold water (50 ml) to the reaction solution and filtering out the precipitated solids, the solids obtained were suspended in a mixed solvent (200 ml) of ethanol/water (9:1), and triethylamine (1 ml) was added thereto and then heated under reflux for 7 hours. After concentrating the reaction solution under a reduced pressure, the residue was dissolved in chloroform (100 ml), and after washing the organic layer with a 10% aqueous citric acid solution (50 ml), the organic layer was dried over anhydrous sodium sulfate. After filtering, the filtrate was concentrated under a reduced pressure, and after adding dropwise the concentrated hydrochloric acid (2 ml) to the residue while cooling with ice, it was stirred at room temperature for 30 minutes. 1 mol/l Hydrochloric acid (2 ml) was then added to the reaction solution, and after washing the yellow acidic aqueous solution with chloroform (50 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×4) was performed. After drying over anhydrous sodium sulfate, the solvent was evapolated under a reduced pressure. The residue thus obtained was purified by recrystallization in ethanol and then dried under a reduced pressure. 99.6 mg (46%) of the title compound was thereby obtained in the form of yellow crystals.

$^1$H-NMR (400 MHz, 0.1 mol/l NaOD) δ: 0.55-0.57 (4H, m), 0.74-0.76 (1H, m), 0.90-0.92 (1H, m), 1.11-1.13 (1H, m), 1.24-1.26 (1H, m), 1.75-1.77 (1H, m), 2.03-2.05 (1H, m), 2.21-2.24 (1H, m), 2.48 (3H, s), 3.29-3.38 (3H, m), 3.53-3.55 (1H, m), 4.10-4.12 (1H, m), 7.07 (1H, s), 7.96 (1H, s), 8.57 (1H, s).

Melting point: 230 to 233° C. Specific rotation: $[α]_D^{24.7}$=−169.35° (c 0.385, 0.1 mol/l NaOH) Elemental analysis: As $C_{21}H_{25}N_3O_3$; Calcd.: C 68.48%; H 6.86%; N 11.44%. Found: C 68.46%; H 6.71%; N 11.38%.

Reference Example 6

Ethyl 2-(2,6-dichloronicotinoyl)acetate

Monoethyl malonate (6.61 g, 50.0 mmol) was dissolved in anhydrous tetrahydrofuran (100 ml), and after adding magnesium ethoxide (3.15 g, 28.0 mmol) thereto while cooling with ice, it was stirred at room temperature for 3 hours. The reaction solution was then concentrated under a reduced pressure, thereby preparing a magnesium salt of monoethyl malonate. 2,6-dichloronicotinic acid (3.84 g, 20.0 mmol) was then dissolved in anhydrous tetrahydrofuran (80 ml), and after adding 1,1-carbonyldiimidazole (4.87 g. 30.0 mmol) while cooling with ice, it was stirred at room temperature for 1.5 hours. To this solution, a solution, wherein the previously prepared magnesium salt of monoethyl malonate was dissolved in anhydrous tetrahydrofuran (160 ml), was added dropwise over a period of 10 minutes while cooling with ice. After completion of dripping, the temperature was gradually brought back to room temperature and thereafter, stirring was performed for 4 hours. After adding ethyl acetate (200 ml) to the reaction solution, the organic layer was washed with a 10% aqueous citric acid solution (150 ml×2), saturated sodium bicarbonate water (150 ml), and saturated saline solution (150 ml), in that order, and then dried over anhydrous sodium sulfate. After filtering, the residue obtained by concentration under a reduced pressure of the filtrate was applied to a silica gel chromatography, and 4.24 g (81%) of the title compound was obtained in the form of a pale-pink, oily substance from an n-hexane:ethyl acetate=3:1 eluate.

$^1$H-NMR (400 MHz, CHCl$_3$) δ: 1.12-1.40 (3H, m), 4.08 (1H, s), 4.15-4.35 (2H, m), 5.72 (0.5H, s), 7.37 (1H, dd, J=14.5, 8.1 Hz), 9.49 (1H, dd, J=16.4, 8.1 Hz), 12.52 (0.5H, s).

Reference Example 7

Ethyl 2-(2,6-dichloronicotinoyl)-3-[2-(S)-fluoro-1-(R)-cyclopropylamino]acrylate Ethyl 2-(2,6-dichloronicotinoyl)acetate (7.03 g, 26.8 mmol) was dissolved in acetic anhydride (30 ml), and after adding triethyl orthoformate (60 ml) thereto, it was stirred in an oil bath of 140° C. for 2 hours. After letting the reaction solution cool, it was concentrated under a reduced pressure, and after adding toluene (50 ml) to the residue obtained, a concentration operation under a reduced pressure was performed. This operation was repeated 3 times, and the residue obtained was dried under a reduced pressure. 8.42 g of ethyl 2-(2,6-dichloronicotinoyl)-3-ethoxyacrylate was thereby obtained in the form of a yellow oily substance.

Next, this crude ethyl 2-(2,6-dichloronicotinoyl)-3-ethoxyacrylate (2.11 g, 6.62 mmol) and the para-toluenesulfonic acid salt of 2-(S)-fluoro-1-(R)-cyclopropylamine (2.45 g, 9.91 mmol) were suspended in dichloromethane (30 ml), and triethylamine (2.77 ml, 19.87 mmol) was added dropwise gradually thereto while stirring at −15° C. After completion of dripping, the reaction solution was stirred at room temperature for 15 hours. After adding ethyl acetate (100 ml) to the reaction solution, the organic layer was washed with a 10% aqueous citric acid solution (80 ml), saturated sodium bicarbonate water (80 ml), and saturated saline solution (80 ml), in that order, and then dried over anhydrous sodium sulfate. After filtering, the filtrate was concentrated under a reduced pressure, and 2.10 g (90%, 2 processes) of the title compound was thereby obtained as a yellowish-brown, oily substance (E/Z mixture). This resulting substance was used in the subsequent reaction without further purification.

$^1$H-NMR (400 MHz, CHCl$_3$) δ: 0.85-0.89 (0.7H, m), 1.00-1.04 (2.3H, m), 1.23-1.38 (2H, m), 3.01 (1H, m), 3.94-4.05 (2H, m), 4.65-4.84 (1H, m), 7.27-7.31 (1H, m), 7.50-7.57 (1H, m), 8.29-8.38 (1H, m), 11.02 (0.8H, brd, J=12.5 Hz).

Reference Example 8

Ethyl 7-chloro-1-[2-(S)-fluoro-1-(R)-cyclopropyl]-1,4-dihydro-4-oxo-1,8-naphthylidine-3-carboxylate After dissolving ethyl 2-(2,6-dichloronicotinoyl)-3-[2-(S)-fluoro-1-(R)-cyclopropylamino]acrylate (2.07 g, 5.97 mmol) in 1,4-dioxane (30 ml), 60% oily sodium hydride (287 mg, 7.18 mmol) was added gradually thereto while stirring at 5° C. The reaction suspension was then stirred for 1.5 hours at room temperature and then concentrated under a reduced pressure. After dissolving the residue in chloroform (100 ml), the organic layer was washed with a 10% aqueous citric acid solution (80 ml), saturated sodium bicarbonate water (80 ml), and saturated saline solution (80 ml), in that order, and then dried over anhydrous sodium sulfate. After filtering, the filtrate was concentrated under a reduced pressure, diethyl ether was added to the residue thus obtained, and the precipitated crystals were filtered out, washed with diethyl ether, and then dried under a reduced pressure at 60° C. for 16 hours. 1.25 g (67%) of the title compound was thereby obtained in the form of a white powder.

$^1$H-NMR (400 MHz, CHCl$_3$) δ: 1.41 (3H, t, J=7.1 Hz), 1.59-1.72 (2H, m), 3.58-3.63 (1H, m), 4.41 (2H, q, J=7.1 Hz), 4.93-5.12 (1H, m), 7.39-7.41 (1H, m), 8.65-8.68 (2H, m). MS (m/z): 310 (M$^+$)

Reference Example 9

7-chloro-1-[2-(S)-fluoro-1-(R)-cyclopropyl]-1,4-dihydro-4-oxo-1,8-naphthylidine-3-carboxylic acid A mixture of ethyl 7-chloro-1-[2-(S)-fluoro-1-(R)-cyclopropyl]-1,4-dihydro-4-oxo-1,8-naphthylidine-3-carboxylate (567 mg, 1.83 mmol), acetic acid (4 ml) and concentrated hydrochloric acid (2 ml) was heated under reflux for 2.5 hours. After cooling the reaction solution with ice, ice water (20 ml) was poured into the reaction solution, the precipitated crystals were filtered out, and after washing with excess water, a small amount of cold ethanol, and excess diethyl ether, the crystals were dried under a reduced pressure at 80° C. for 18 hours. 449 mg (87%) of the title compound was thereby obtained in the form of white needle crystals.

$^1$H-NMR (400 MHz, CHCl$_3$) δ: 1.70-1.80 (2H, m), 3.73-3.79 (1H, m), 4.98-5.17 (1H, m), 7.56 (1H, d, J=8.3 Hz), 8.73 (1H, d, J=8.5 Hz), 8.97 (1H, s), 14.11 (1H, brs).

Melting point: 215 to 220° C. Specific rotation: [α]$_D^{24.5}$=+26.90° (c 0.422, 0.1 mol/l NaOH) Elemental analysis: As C$_{12}$H$_8$ClFN$_2$O$_3$; Calcd.: C, 50.99%; H, 2.85%; N, 9.91%. Found: C, 50.90%; H, 2.71%; N, 9.91%. MS (m/z): 282 (M$^+$)

Example 4

7-[3-(R)-(1-aminocyclopropyl)pyrrolidin-1-yl]-1-[2-(S)-fluoro-1-(R)-cyclopropyl]-1,4-dihydro-4-oxo-1,8-naphthylidine-3-carboxylic acid After adding 3-(R)-[1-[N-(tert-butoxycarbonyl)amino]cyclopropyl]pyrrolidine (339 mg, 1.50 mmol) and triethylamine (1.39 ml) to dried acetonitrile (10 ml), 7-chloro-1-[2-(S)-fluoro-1-(R)-cyclopropyl]-1,4-dihydro-4-oxo-1,8-naphthylidine-3-carboxylic acid (283 mg, 1.00 mmol) was added thereto and the mixture was heated under reflux for 1.5 hours under a nitrogen atmosphere. After concentrating the reaction solution under a reduced pressure, the residue was dissolved in a mixed solvent of ethyl acetate (100 ml) and dichloromethane (50 ml), and after washing the organic layer with a 10% aqueous citric acid solution (50 ml) and saturated saline solution (50 ml) in that order, the organic layer was dried over anhydrous sodium sulfate. After filtering, the filtrate was concentrated under a reduced pressure, and after adding dropwise concentrated hydrochloric acid (15 ml) to the residue while cooling with ice, it was stirred at the same temperature for 30 minutes. 1 mol/l Hydrochloric acid (10 ml) was then added to the reaction solution, and after washing the yellow acidic aqueous solution with chloroform (50 ml×4), the pH was adjusted to 11.0 with an aqueous sodium hydroxide solution. After adjusting the pH of the basic aqueous solution to 7.4 with 1 mol/l hydrochloric acid, extraction with the lower layer (100 ml×2) of a 7:3:1 mixture of chloroform:methanol:water was performed. The organic layers were then combined, and after drying the organic layer over anhydrous sodium sulfate, the solvent was evapolated under a reduced pressure. The residue obtained was purified by recrystallization in ethanol and then dried under a reduced pressure. 263 mg (74%) of the title compound was thereby obtained in the form of white crystals.

$^1$H-NMR (400 MHz, 0.1 mol/l NaOD) δ: 0.49-0.55 (4H, m), 1.50-1.75 (3H, m), 1.95-2.15 (2H, m), 3.00-3.80 (5H, m), 4.90-5.15 (1H, m), 6.38 (1H, dm, J=9.1 Hz), 8.01 (1H, d, J=9.1 Hz), 8.31 (1H, s). IR (KBr, disk) ν: 3089, 3008, 2871, 1712, 1624, 1566, 1508, 1446, 1379, 1333, 1257, 1187, 1136, 1095, 1024, 985 cm$^{-1}$.

Melting point: 216 to 218° C. Specific rotation: [α]$_D^{24.5}$=+63.50° (c 0.310, 0.1 mol/l NaOH) Elemental analysis: As C$_{19}$H$_{21}$FN$_4$O$_3$; Calcd.: C, 61.28%; H, 5.68%; N, 15.04%. Found: C, 61.17%; H, 5.66%; N, 15.04%. MS (m/z): 373 ([M+H])$^+$ Reference Example 10

Ethyl 2,4-difluorobenzoyl acetate

Under a nitrogen atmosphere, monoethyl malonate (9.25 g, 70.0 mmol) was dissolved in anhydrous tetrahydrofuran (150 ml), and after adding magnesium ethoxide (4.17 g, 36.8 mmol) while cooling with ice, it was stirred at room temperature for 1 hour. The reaction solution was then concentrated under a reduced pressure, thereby preparing a magnesium salt of monoethyl malonate. 2,4-difluorobenzoic acid (7.91 g, 50.0 mmol) was then dissolved in anhydrous tetrahydrofuran (100 ml), and after adding 1,1-carbonyldiimidazole (8.52 g, 52.5 mmol) while cooling with ice, it was stirred at room temperature for 1 hour. To this solution, a solution, wherein the previously prepared magnesium salt of monoethyl malonate was dissolved in anhydrous tetrahydrofuran (60 ml), was added dropwise while cooling with ice. After completion of dripping, the temperature was gradually brought back to room temperature and thereafter, stirring was performed for 16 hours. After adding toluene (100 ml) to the reaction solution, the organic layer was washed with a 10% aqueous citric acid solution (200 ml), saturated sodium bicarbonate water (150 ml), and saturated saline solution (150 ml), in that order, and then dried over anhydrous sodium sulfate. After filtering, the residue obtained by concentration under a reduced pressure of the filtrate was applied to a silica gel chromatography, and 11.0 g (95%) of the title compound was obtained in the form of a pale-yellow, oily substance from an n-hexane:ethyl acetate=9:1 eluate.

$^1$H-NMR (400 MHz, CHCl$_3$) δ: 1.24-1.36 (3H, m), 3.95 (2H×2/3, d, J=3.66 Hz), 4.20-4.30 (2H, m), 5.80 (1H×1/3, s), 6.86-7.02 (2H, m), 7.88-8.04 (1H, m), 12.72 (1H×1/3, s).

Reference Example 11

Ethyl 7-fluoro-1-[2-(S)-fluoro-1-(R)-cyclopropyl]-1,4-dihydro-4-oxoquinoline-3-carboxylate A mixture of ethyl 2,4-difluorobenzoyl acetate (5.50 g, 24.1 mmol), triethyl orthoformate (8.00 ml, 48.2 mmol) and acetic anhydride (6.8 ml) was stirred in an oil bath of 120° C. for 16 hours. After letting the reaction solution cool, it was concentrated under a reduced pressure, and after adding toluene (30 ml) to the residue obtained, it was concentrated under a reduced pressure again, and then dried under a reduced pressure. A yellow oily substance was thereby obtained. This substance was dissolved in toluene (100 ml), and after adding the para-toluenesulfonic acid salt of 2-(S)-fluoro-1-(R)-cyclopropylamine (6.46 g, 26.1 mmol), triethylamine (4.95 ml, 35.6 mmol) was added dropwise gradually thereto while stirring at −15° C. After completion of dripping, the reaction solution was stirred at room temperature for 18 hours. After adding water (150 ml) to the reaction solution, extraction with ethyl acetate (150 ml×2) was performed. The organic layers were combined and washed with saturated saline solution (150 ml) and then dried over anhydrous sodium sulfate. After filtering, the filtrate was concentrated under a reduced pressure, and a brown oily substance was thereby obtained. After dissolving this substance in dimethylformamide (35 ml), potassium carbonate (6.55 g, 47.4 mmol) was added thereto and then stirred at room temperature for 21 hour. Then while cooling with ice and stirring, 2 mol/l hydrochloric acid (50 ml) was added gradually thereto and then stirred at room temperature for 6 hours. The precipitated crystals were filtered out and then washed with excess water, a small amount of cold ethanol and excess diethyl ether. The crude crystals obtained were then purified by recrystallization in ethyl acetate and then dried under a reduced pressure. 5.92 g (84%) of the title compound was thereby obtained.

$^1$H-NMR (400 MHz, CHCl$_3$) δ: 1.41-1.43 (3H, m), 1.69-1.76 (2H, m), 3.39 (1H, brs), 4.37-4.43 (2H, m), 5.09 (1H, dm, J=62.46 Hz), 7.16-7.22 (1H, m), 7.41-7.44 (1H, m), 8.49-8.57 (2H, m).

Melting point: 227 to 230° C.

Reference Example 12

7-fluoro-1-[2-(S)-fluoro-1-(R)-cyclopropyl]-1,4-dihydro-4-oxoquinoline-3-carboxylic acid A mixture of ethyl 7-fluoro-1-[2-(S)-fluoro-1-(R)-cyclopropyl]-1,4-dihydro-4-oxoquinoline-3-carboxylate (4.08 g, 13.9 mmol), acetic acid (9 ml) and concentrated hydrochloric acid (9 ml) was heated under reflux for 21 hour. After cooling the reaction solution with ice, ice water (50 ml) was poured into the reaction solution, the precipitated crystals were filtered out, and after washing with excess water, a small amount of cold ethanol and excess diethyl ether, the crystals were dried under a reduced pressure at 80° C. for 16 hours. 3.51 g (95%) of the title compound was thereby obtained in the form of a white powder.

$^1$H-NMR (400 MHz, CDCl$_3$) δ: 1.78-1.84 (2H, m), 3.52-3.53 (1H, m), 5.13 (1H, dm, J=64.59 Hz), 7.31-7.36 (1H, m), 7.59 (1H, d, J=9.26 Hz), 8.54-8.53 (1H, m), 14.55 (1H, s).

Melting point: 302 to 305° C. Specific rotation: $[\alpha]_D^{24.3}$=+0.38° (c 0.560, 0.1 mol/l NaOH)

Example 5

7-[3-(R)-(1-aminocyclopropyl)pyrrolidin-1-yl]-1-[2-(S)-fluoro-1-(R)-cyclopropyl]-1,4-dihydro-4-oxoquinoline-3-carboxylic acid After adding 3-(R)-[1-[N-(tert-butoxycarbonyl)amino]cyclopropyl]pyrrolidine (203 mg, 817 μmol) and triethylamine (0.5 ml) to dried dimethyl sulfoxide (1 ml), 7-fluoro-1-[2-(S)-fluoro-1-(R)-cyclopropyl]-1,4-dihydro-4-oxoquinoline-3-carboxylic acid (197 mg, 743 μmol) was added thereto and the mixture was heated reflux for 15 hours under a nitrogen atmosphere. After letting the reaction solution cool, water (30 ml) was added to the reaction solution while cooling with ice, and the precipitated crystals were filtered out and washed well with water. After adding concentrated hydrochloric acid (5 ml) to the obtained crystals while cooling with ice, stirring at the same temperature was performed for 30 minutes. 1 mol/l hydrochloric acid (10 ml) was then added to the reaction solution, and after washing the yellow acidic aqueous solution with chloroform (50 ml×2), the pH was adjusted to 12.0 with an aqueous sodium hydroxide solution. After adjusting the pH of the basic aqueous solution to 7.4 with 1 mol/l hydrochloric acid, extractions into chloroform (100 ml×3) and a 95:5 mixture of chloroform:methanol (100 ml×2) were performed. The organic layers were then combined, and after drying the organic layer over anhydrous sodium sulfate, the solvent was evapolated under a reduced pressure. The residue obtained was purified by recrystallization in ethanol and then dried under a reduced pressure. 203 mg (74%) of the title compound was thereby obtained in the form of yellow crystals.

$^1$H-NMR (400 MHz, 0.1 mol/l NaOD) δ: 0.50-0.54 (4H, m), 1.63-1.68 (3H, m), 2.00-2.12 (2H, m), 2.94-2.97 (1H, m), 3.16-3.36 (4H, m), 5.16 (1H, dm, J=62.40 Hz), 6.43 (1H, s), 6.67 (1H, d, J=9.02 Hz), 7.97 (1H, d, J=9.02 Hz), 8.32 (1H, s). IR (KBr, disk) v: 3087, 3008, 2951, 2858, 1699, 1681, 1520, 1471, 1458, 1396, 1363, 1371, 1250 cm$^{-1}$.

Melting point: 251 to 253° C. Specific rotation: $[\alpha]_D^{24.3}$=+41.90° (c 0.160, 1 mol/l NaOH) Elemental analysis: As $C_{20}H_{22}FN_3O_3$; Calcd.: C, 64.68%; H, 5.97%; N, 11.31%. Found: C, 64.69%; H, 5.96%; N, 11.25%.

Reference Example 13

7-bromo-1-cyclopropyl-8-difluoromethoxy-1,4-dihydro-4-oxoquinoline-3-carboxylic acid $BF_2$ chelate

While heating and stirring a mixed solution of ethyl 7-bromo-1-cyclopropyl-8-difluoromethoxy-1,4-dihydro-4-oxoquinoline-3-carboxylate (2.01 g, 5.00 mmol), acetic acid (5 ml) and acetic anhydride (5 ml) in an oil bath of 110° C., a boron trifluoride—tetrahydrofuran complex (0.83 ml, 7.50 mmol) was added dropwise over a period of 5 minutes. After stirring the reaction solution at the same temperature for 1.5 hours, excess diethyl ether was added while cooling with ice, and the precipitated solids were filtered out (and washed with diethyl ether). After drying under a reduced pressure at room temperature, 2.06 g (98%) of the title compound was obtained as a pale gray powder.

$^1$H-NMR (400 MHz, $d_6$-DMSO) δ: 1.15-1.30 (4H, m), 4.43 (1H, m), 7.20 (1H, t, J=71.9 Hz), 8.25 (1H, d, J=8.8 Hz), 8.38 (1H, d, J=8.8 Hz), 9.36 (1H, s).

Example 6

7-[3-(R)-(1-aminocyclopropyl)pyrrolidin-1-yl]-1-cyclopropyl-8-difluoromethoxy-1,4-dihydro-4-oxoquinoline-3-carboxylic acid

After adding 3-(R)-[1-(tert-butoxycarbonylamino)cyclopropyl]pyrrolidine (338 mg, 1.50 mmol) and triethylamine (209 μl, 1.50 mmol) to dried dimethyl sulfoxide (2 ml), 7-bromo-1-cyclopropyl-8-difluoromethoxy-1,4-dihydro-4-oxoquinoline-3-carboxylic acid $BF_2$ chelate (422 mg, 1.00 mmol) was added thereto and stirred at room temperature for 39 hours under a nitrogen atmosphere. After concentrating the reaction solution under a reduced pressure, ethanol (20 ml), triethylamine (4 ml) and water (4 ml) were added to the concentrate and heated under reflux for 3 hours. After concentrating the reaction solution under a reduced pressure, the residue was dissolved in chloroform (100 ml), and after washing the organic layer in a 10% aqueous citric acid solution (50 ml), the organic layer was dried over anhydrous sodium sulfate. After filtering, the filtrate was concentrated under a reduced pressure, and after adding dropwise concentrated hydrochloric acid (5 mL) to the residue while cooling with ice, it was stirred at room temperature for 30 minutes. 3 mol/l Hydrochloric acid (30 ml) was then added to the reaction solution, and after washing the yellow acidic aqueous solution with chloroform (50 ml×2), the pH was adjusted to 11.0 with an aqueous sodium hydroxide solution. After adjusting the pH of the basic aqueous solution to 7.4 with 1 mol/l hydrochloric acid, extraction with chloroform (50 ml×2) was performed. After drying over anhydrous sodium sulfate, the solvent was evaporated under a reduced pressure. The residue thus obtained was purified by recrystallization in a mixed solvent of ethanol/diethyl ether and then dried under a reduced pressure. 31 mg (8%) of the title compound was thereby obtained in the form of a yellow powder.

$^1$H-NMR (400 MHz, 0.1 mol/l NaOD) δ: 0.57 (4H, brs), 0.81 (1H, m), 1.03 (1H, m), 1.11 (1H, m), 1.25 (1H, m), 1.78 (1H, m), 2.05 (1H, m), 2.22 (1H, m), 3.35-3.60 (4H, m), 4.08 (1H, m), 6.45 (1H, dd, J=76.3, 73.8 Hz), 7.07 (1H, d, J=9.3 Hz), 8.00 (1H, d, J=9.3 Hz), 8.46 (1H, s).

Melting point: 206 to 207.5° C. Specific rotation: $[α]_D^{24.5}$=−67.70° (c 0.295, 0.1 mol/l NaOH) Elemental analysis: As $C_{21}H_{23}F_2N_3O_4 \cdot 0.25CH_3CH_2OH$; Calcd.: C, 59.92%; H, 5.73%; N, 9.75%. Found: C, 59.85%; H, 5.62%; N, 9.68%.

Reference Example 14

Ethyl 6-amino-7-fluoro-1-[2-(S)-fluoro-1-(R)-cyclopropyl]-1,4-dihydro-8-methyl-5-nitro-4-oxoquinoline-3-carboxylate

Ethyl 6,7-difluoro-1-[2-(S)-fluoro-1-(R)-cyclopropyl]-1,4-dihydro-8-methyl-5-nitro-4-oxoquinoline-3-carboxylate (10.04 g, 27.12 mmol) was dissolved in dimethylformamide (150 ml), and 28% ammonia water (32.1 ml) was added dropwise thereto while stirring and cooling with ice. While sealing the reaction solution in a sealed tube, it was stirred at room temperature for 4 hours. The reaction solution was then dissolved in methanol (200 ml) and concentrated under a reduced pressure. The residue obtained was purified by recrystallization from a mixed solvent of 2-propanol/chloroform/28% ammonia water, and after drying under a reduced pressure, 7.07 g (71%) of the title compound was obtained as a yellow powder.

$^1$H-NMR (400 MHz, $CDCl_3$) δ: 1.35-1.44 (5H, m), 2.67 (3H, d, J=3.41 Hz), 3.81-3.87 (1H, m), 4.33-4.41 (3H, m), 4.75-4.78 (0.5H, m), 4.90-4.94 (0.5H, m), 8.47 (1H, d, J=3.41 Hz). Elemental analysis: As $C_{16}H_{15}F_2N_3O_5$; Calcd.: C, 52.32%; H, 4.12%; N, 11.44%. Found: C, 52.62%; H, 4.16%; N, 11.12%.

Reference Example 15

Ethyl 7-fluoro-1-[2-(S)-fluoro-1-(R)-cyclopropyl]-1,4-dihydro-8-methyl-5-nitro-4-oxoquinoline-3-carboxylate

Isoamyl nitrite (2.56 ml, 19.1 mmol) was added to dimethylformamide (40 ml), and while stirring at 65° C., a solution, wherein ethyl 6-amino-7-fluoro-1-[2-(S)-fluoro-1-(R)-cyclopropyl]-1,4-dihydro-8-methyl-5-nitro-4-oxoquinoline-3-carboxylate (5.00 g, 13.6 mmol) was dissolved in dimethylformamide (60 ml), was added dropwise over a period of 3 hours. After completion of dripping, the reaction solution was stirred at 65° C. for 4 hours, allowed to cool, and then poured into water (500 ml). After extraction with chloroform (200 ml×3), the organic layers combined were washed with 1 mol/l hydrochloric acid (200 ml) and saturated saline solution (100 ml×2) in that order, and then dried over anhydrous sodium sulfate. After filtering, the filtrate was concentrated under a reduced pressure, and the residue obtained was applied to a silica gel chromatography to obtain 2.91 g (61%) of the title compound in the form of a white powder from a chloroform:methanol=30:1 eluate.

$^1$H-NMR (400 MHz, $CDCl_3$) δ: 1.37 (3H, t, J=7.08 Hz), 1.40-1.67 (2H, m), 2.70 (3H, d, J=2.93 Hz), 3.89-3.93 (1H, m), 4.34-4.40 (2H, m), 4.79-4.83 (0.5H, m), 4.95-4.98 (0.5H, m), 8.55 (1H, d, J=2.93 Hz).

Reference Example 16

Ethyl 5-amino-7-fluoro-1-[2-(S)-fluoro-1-(R)-cyclopropyl]-1,4-dihydro-8-methyl-4-oxoquinoline-3-carboxylate

Ethyl 7-fluoro-1-[2-(S)-fluoro-1-(R)-cyclopropyl]-1,4-dihydro-8-methyl-5-nitro-4-oxoquinoline-3-carboxylate (2.50 g, 7.10 mmol) was dissolved in acetonitrile (20 ml), and after adding a 5% palladium carbon catalyst (water content: 50%, 1.0 g) thereto, it was stirred at room temperature for 20 hours under a hydrogen atmosphere at atmospheric pressure. After removing the catalyst by filtering (methanol washing), the filtrate was concentrated under a reduced pressure, and the residue obtained was dissolved in ethyl acetate (10 ml) and heated under reflux for 30 minutes. n-hexane (10 ml) was then added, and after performing heated refluxing for 30 minutes, there action solution was allowed to stand under room temperature. The precipitated crystals were then filtered out, washed with a 1:1 mixed solution of n-hexane:ethyl acetate and dried under a reduced pressure at 60° C. for 16 hours. 869 mg (38%) of the title compound was thereby obtained as a yellow powder.

$^1$H-NMR (400 MHz, CDCl$_3$) δ: 1.23-1.36 (1H, m), 1.38 (3H, t, J=7.08 Hz), 1.43-1.56 (1H, m), 2.39 (3H, d, J=2.20 Hz), 3.70-3.77 (1H, m), 4.37 (2H, q, J=7.08 Hz), 4.71-4.75 (0.5H, m), 4.87-4.90 (0.5H, m), 6.20 (1H, d, J=11.96 Hz), 8.37 (1H, d, J=3.42 Hz).

Reference Example 17

5-amino-7-fluoro-1-[2-(S)-fluoro-1-(R)-cyclopropyl]-1,4-dihydro-8-methyl-4-oxoquinoline-3-carboxylic acid Ethyl 5-amino-7-fluoro-1-[2-(S)-fluoro-1-(R)-cyclopropyl]-1,4-dihydro-8-methyl-4-oxoquinoline-3-carboxylate (735 mg, 2.28 mmol) was dissolved in a 1:1 mixed solution (8 ml) of acetic acid:water, and after adding concentrated sulfuric acid (90 µl) thereto, it was stirred for 4 hours in an oil bath of 120° C. After cooling the reaction solution with ice, water (20 ml) was poured therein, and the mixed reaction solution was stirred at room temperature for 2 hours. The precipitated crystals were filtered out, washed with excess water, a small amount of cold ethanol and excess diethyl ether in that order, and then dried under a reduced pressure at 80° C. for 17 hours. 552 mg (82%) of the title compound was thereby obtained in the form of yellow crystals.

$^1$H-NMR (400 MHz, DMSO-d$_6$) δ: 1.23-1.38 (1H, m), 1.56-1.66 (1H, m), 2.39 (3H, d, J=2.20 Hz), 4.14-4.22 (1H, m), 4.96-5.00 (0.5H, m), 5.12-5.16 (0.5H, m), 6.50 (1H, d, J=12.70 Hz), 8.60 (1H, d, J=3.17 Hz). Specific rotation: $[α]_D^{24.3}$=−111.00° (c 0.510, 0.1 mol/l NaOH)

Example 7

5-amino-7-[3-(R)-(1-aminocyclopropyl)pyrrolidin-1-yl]-1-[2-(S)-fluoro-1-(R)-cyclopropyl]-1,4-dihydro-8-methyl-4-oxoquinoline-3-carboxylic acid After adding 3-(R)-[1-[N-(tert-butoxycarbonyl)amino]cyclopropyl]pyrrolidine (643 mg, 2.55 mmol) and triethylamine (0.5 ml) to dried dimethyl sulfoxide (1 ml, 5-amino-7-fluoro-1-[2-(S)-fluoro-1-(R)-cyclopropyl]-1,4-dihydro-8-methyl-4-oxoquinoline-3-carboxylic acid (250 mg, 850 µmol) was added thereto and stirred at 70° C. for 37 hours while sealing under a nitrogen atmosphere. After letting the reaction solution cool, the reaction solution was concentrated under a reduced pressure, the residue obtained was dissolved in ethyl acetate (100 ml), and washed with a 10% aqueous citric acid solution (50 ml) and saturated saline solution (30 ml). The organic layer was then dried over anhydrous sodium sulfate, and after filtering, the filtrate was concentrated under a reduced pressure. The residue obtained was then applied to a short silica gel chromatography and crude crystals were obtained from a chloroform:methanol=30:1 eluate. After adding dropwise concentrated hydrochloric acid (5 ml) to the crude crystals while cooling with ice, it was stirred at the same temperature for 30 minutes. 1 mol/l Hydrochloric acid (10 ml) was then added to the reaction solution, and after washing the yellow acidic aqueous solution with chloroform (50 ml×2), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. The organic layers were then combined and dried over anhydrous sodium sulfate, and then the solvent was evapolated under a reduced pressure. The residue thus obtained was purified by recrystallization from ethanol and then dried under a reduced pressure. 32 mg (9%) of the title compound was thereby obtained in the form of yellow crystals.

$^1$H-NMR (400 MHz, 0.1 mol/l NaOD) δ: 0.54-0.57 (1H, m), 0.60-0.67 (1H, m), 1.23-1.55 (3H, m), 1.74-1.85 (1H, m), 1.97-2.17 (2H, m), 2.33 (3H, s), 3.18-3.27 (2H, m), 3.43-3.47 (1H, m), 3.54-3.63 (1H, m), 3.71-3.78 (1H, m), 4.77-4.79 (0.5H, m), 4.93-4.96 (0.5H, m), 6.00 (1H, s), 8.56 (1H, d, J=3.66 Hz). IR (KBr, disk) ν: 3402, 3344, 3276, 3097, 2918, 2864, 1724, 1616, 1548, 1506, 1477, 1441, 1408 cm$^{-1}$.

Melting point: 240 to 242° C. (decomposed) Specific rotation: $[α]_D^{23.5}$=−225.91° (c 0.525, 0.1 mol/l NaOH) Elemental analysis: As C$_{21}$H$_{25}$FN$_4$O$_3$; Calcd.: C, 62.99%; H, 6.29%; N, 13.99%. Found: C, 62.86%; H, 6.38%; N, 13.76%.

Reference Example 18

Ethyl 6-amino-7-fluoro-1-[2-(S)-fluoro-1-(R)-cyclopropyl]-1,4-dihydro-8-methoxy-5-nitro-4-oxoquinoline-3-carboxylate Ethyl 6,7-difluoro-1-[2-(S)-fluoro-1-(R)-cyclopropyl]-1,4-dihydro-8-methoxy-5-nitro-4-oxoquinoline-3-carboxylate (13.96 g, 36.14 mmol) was dissolved in dimethyl formamide (180 ml), and 28% ammonia water (60 ml) was added dropwise in while stirring and cooling with ice. After stirring the reaction solution at room temperature for 64 hours, water (100 ml) was added to the reaction solution and then concentrated under a reduced pressure. The water-containing residue obtained was then subjected to extraction with ethyl acetate (100 ml×3), and the organic layers were then combined, washed with water (150 ml×3) and saturated saline solution (200 ml) in that order, and then dried over anhydrous sodium sulfate. After filtering, the filtrate was concentrated under a reduced pressure, the residue obtained was applied to a silica gel chromatography, and 8.92 g (64%) of the title compound was obtained in the form of a pale red, oily substance from a chloroform:methanol=30:1 eluate.

$^1$H-NMR (400 MHz, CDCl$_3$) δ: 1.37 (3H, t, J=7.0 Hz), 1.49 (1H, ddd, J=9.5, 6.0, 3.5 Hz), 1.53-1.58 (1H, m), 3.68 (1H, dt, J=8.5, 5.5 Hz), 4.11 (3H, d, J=2.5 Hz), 4.36 (2H, dq, J=7.0, 1.5 Hz), 4.51 (2H, br), 4.83 (1H, ddt, J=63.3, 5.5, 3.5 Hz), 8.47 (1H, s). IR (KBr, disk) ν: 3379, 1724, 1608, 1525, 1471, 1323, 1259, 1063 cm$^{-1}$. HRMS (FAB): As C$_{16}$H$_{16}$F$_2$N$_3$O$_6$ (M$^+$+1); Calcd.: 384.1007. Found: 384.0974.

Reference Example 19

Ethyl 7-fluoro-1-[2-(S)-fluoro-1-(R)-cyclopropyl]-1,4-dihydro-8-methoxy-5-nitro-4-oxoquinoline-3-carboxylate Isoamyl nitrite (3.81 g, 32.5 mmol) was added to dimethylformamide (60 ml), and while stirring at 70° C., a solution, wherein ethyl 6-amino-7-fluoro-1-[2-(S)-fluoro-1-(R)-cyclopropyl]-1,4-dihydro-8-methoxy-5-nitro-4-oxoquinoline-3-carboxylate (8.90 g, 23.2 mmol) was dissolved in dimethylformamide (120 ml), was added dropwise thereto over a period of 3 hours. After completion of dripping, the reaction solution was stirred at 70° C. for 1 hour, allowed to cool, and then poured into water (500 ml). After extraction with ethyl acetate (300 ml×3), the organic layers combined were washed with 1 mol/l hydrochloric acid (300 ml) and saturated saline solution (200 ml×2) in that order, and then dried over anhydrous sodium sulfate. After filtering, the filtrate was concentrated under a reduced pressure, and the crude crystals obtained were recrystallized in ethanol and then dried under a reduced pressure. 3.81 g (45%) of the title compound was thereby obtained in the form of yellow crystals.

$^1$H-NMR (400 MHz, CDCl$_3$) δ: 1.37 (3H, t, J=7.0 Hz), 1.55 (1H, ddd, J=9.5, 6.0, 3.5 Hz), 1.59-1.69 (1H, m) 3.93 (1H, dt, J=8.5, 5.5 Hz), 4.11 (3H, t, J=2.5 Hz), 4.37 (2H, dq, J=7.0, 1.5 Hz), 4.86 (1H, dddd, J=63.0, 6.0, 5.5, 3.5 Hz), 7.20 (1H, d, J=10.0 Hz), 8.55 (1H, d, J=1.5 Hz). IR (KBr, disk) ν: 3062, 1722, 1639, 1602, 1544, 1425, 1328, 1259, 1057 cm$^{-1}$.

Melting point: 167 to 170° C. (decomposed) Elemental analysis: As C$_{16}$H$_{14}$F$_2$N$_2$O$_6$; Calcd.: C, 52.18%; H, 3.89%; N, 7.61%. Found: C, 51.97%; H, 3.78%; N, 7.56%.

Reference Example 20

Ethyl 5-amino-7-fluoro-1-[2-(S)-fluoro-1-(R)-cyclopropyl]-1,4-dihydro-8-methoxy-4-oxoquinoline-3-carboxylate Ethyl 7-fluoro-1-[2-(S)-fluoro-1-(R)-cyclopropyl]-1,4-dihydro-8-methoxy-5-nitro-4-oxoquinoline-3-carboxylate (3.71 g, 10.1 mmol) was dissolved in acetonitrile (50 ml), and after adding a 5% palladium carbon catalyst (water content: 50%, 1.5 g) thereto, it was stirred at room temperature for 20 hours under a hydrogen atmosphere at atmospheric pressure. After removing the catalyst by filtering (methanol washing), the filtrate was concentrated under a reduced pressure, the residue obtained was applied to a silica gel chromatography, and 2.68 g (79%) of the title compound was obtained as a yellow amorphous substance from a chloroform:methanol=30:1 eluate.

$^1$H-NMR (400 MHz, CDCl$_3$) δ: 1.38 (3H, t, J=7.0 Hz), 1.43-1.57 (2H, m), 3.75-3.82 (4H, m), 4.37 (2H, q, J=7.0 Hz), 4.81 (1H, ddt, J=62.5, 6.5, 3.5 Hz), 6.24 (1H, d, J=13.0 Hz), 8.37 (1H, d, J=2.0 Hz). HRMS (FAB): As C$_{16}$H$_{17}$F$_2$N$_2$O$_4$ (M$^+$+1); Calcd.: 339.1156. Found: 339.1150.

Reference Example 21

5-amino-7-fluoro-1-[2-(S)-fluoro-1-(R)-cyclopropyl]-1,4-dihydro-8-methoxy-4-oxoquinoline-3-carboxylic acid A mixture of ethyl 5-amino-7-fluoro-1-[2-(S)-fluoro-1-(R)-cyclopropyl]-1,4-dihydro-8-methoxy-4-oxoquinoline-3-carboxylate (2.68 g, 7.92 mmol), acetic acid (20 ml) and concentrated hydrochloric acid (20 ml) was heated under reflux for 3 hours. After cooling the reaction solution with ice, water (200 ml) was poured therein and the precipitated crystals were filtered out. After washing with excess water, a small amount of cold ethanol and excess diethyl ether in that order, the crude crystals obtained were purified by recrystallization in a mixed solvent of chloroform/methanol and then dried under a reduced pressure. 1.26 g (51%) of the title compound was thereby obtained in the form of yellow crystals.

$^1$H-NMR (400 MHz, DMSO-d$_6$) δ: 1.54-1.64 (2H, m), 3.76 (3H, s), 4.02-4.07 (1H, m), 4.89-5.10 (1H, m), 6.59 (1H, d, J=14.0 Hz), 7.73 (2H, br), 8.57 (1H, d, J=1.5 Hz). IR (KBr, disk) ν: 3432, 3328, 1699, 1576, 1518, 1281, 1236 cm$^{-1}$.

Melting point: 291 to 298° C. (decomposed) Specific rotation: [α]$_D^{25.0}$=+40.01° (c 0.305, 0.1 mol/l NaOH) Elemental analysis: As C$_{14}$H$_{12}$F$_2$N$_2$O$_4$; Calcd.: C, 54.20%; H, 3.90%; N, 9.03%. Found: C, 54.10%; H, 3.86%; N, 9.02%.

Example 8

5-amino-7-[3-(R)-(1-aminocyclopropyl)pyrrolidin-1-yl]-1-[2-(S)-fluoro-1-(R)-cyclopropyl]-1,4-dihydro-8-methoxy-4-oxoquinoline-3-carboxylic acid After adding 3-(R)-[1-[N-(tert-butoxycarbonyl)amino]cyclopropyl]pyrrolidine (788 mg, 3.48 mmol) and triethylamine (2 ml) to dried dimethyl sulfoxide (1 ml, 5-amino-7-fluoro-1-[2-(S)-fluoro-1-(R)-cyclopropyl]-1,4-dihydro-8-methoxy-4-oxoquinoline-3-carboxylic acid (621 mg, 2.00 mol) was added thereto and stirred at 90° C. for 168 hours while sealing in a sealed tube under a nitrogen atmosphere. After letting the reaction solution cool and then concentrating the reaction solution under a reduced pressure, the residue obtained was dissolved in chloroform (200 ml) and washed with a 10% aqueous citric acid solution (100 ml). The organic layer was then dried over anhydrous sodium sulfate, and after filtering, the filtrate was concentrated under a reduced pressure. After adding dropwise concentrated hydrochloric acid (10 ml) to the obtained residue while cooling with ice, it was stirred at the same temperature for 30 minutes. 1 mol/l Hydrochloric acid (20 ml) was then added to the reaction solution, and after washing the yellow acidic aqueous solution with chloroform (50 ml×3), the pH was adjusted to 12.0 with an aqueous sodium hydroxide solution. After adjusting the pH of the basic aqueous solution to 7.8 with 1 mol/l hydrochloric acid, extraction with chloroform (100 ml×3) was performed. The organic layers were then combined and dried over anhydrous sodium sulfate, and then the solvent was evaporated under a reduced pressure. The residue thus obtained was purified by recrystallization from a mixed solvent of ethanol and diethyl ether, and then dried under a reduced pressure. 74 mg (9%) of the title compound was thereby obtained in the form of yellow crystals.

$^1$H-NMR (400 MHz, 0.1 mol/l NaOD) δ: 0.48-0.53 (4H, m), 1.09-1.21 (1H, m), 1.32-1.43 (1H, m), 1.64-1.75 (1H, m), 1.93-2.01 (1H, m), 2.10-2.23 (1H, m), 3.21-3.23 (1H, m), 3.21-2.27 (1H, m), 3.36-3.43 (6H, m), 3.79-3.84 (1H, m), 4.85-4.84 (1H, m), 4.85-5.04 (1H, m), 6.06 (1H, s), 8.01 (1H, d, J=3.5 Hz). IR (KBr, disk) ν: 3454, 3410, 1716, 1617, 1577, 1548, 1511, 1232, 1016 cm$^{-1}$.

Melting point: 172 to 178° C. (decomposed) Elemental analysis: As C$_{21}$H$_{25}$FN$_4$O$_4$.0.75H$_2$O; Calcd.: C, 58.66%; H, 6.21%; N, 13.03%. Found: C, 58.58%; H, 6.02%; N, 12.76%.

Reference Example 22

Ethyl 3-dimethylamino-2-(2,3,4-trifluorobenzoyl)acrylate

A mixed solution of 2,3,4-trifluorobenzoic acid (10.3 g, 58.5 mmol), thionyl chloride (6.4 ml, 87.8 mmol) and a catalytic amount of dimethylformamide was heated under reflux for 30 minutes. After letting the reaction solution cool, the reaction solution was concentrated under a reduced pressure, toluene (30 ml) was added to the residue, and concentration under a reduced pressure was performed again. The residue obtained was then dissolved in tetrahydrofuran (20 ml), and the resulting solution was added to a tetrahydrofuran (40 ml) solution of ethyl β-dimethylaminoacrylate (9.20 g, 64.3 mmol) and triethylamine (10.2 ml, 73.1 mmol) while stirring and cooling with ice. The reaction mixture was then stirred at room temperature for 1.5 hours and then heated under reflux for 16.5 hours. After letting the reaction solution cool, the precipitated solids were removed by filtration and the filtrate was concentrated under a reduced pressure. The residue was then applied to a silica gel chromatography, and 15.1 g (86%) of the title compound was obtained from an n-hexane:ethyl acetate=3:1 eluate.

$^1$H-NMR (400 MHz, CDCl$_3$) δ: 1.00 (3H, t, J=7.1 Hz), 2.88 (3H, brs), 3.33 (3H, brs), 4.01 (2H, q, J=7.1 Hz), 6.95-7.01 (1H, m), 7.34 (1H, brs), 7.80 (1H, s).

Reference Example 23

Ethyl 10-fluoro-2,3-dihydro-3-(S)-methyl-7-oxo-7H-pyrido[1,2,3-de][1,4]benzoxazine-6-carboxylate Ethyl 3-dimethylamino-2-(2,3,4-trifluorobenzoyl)acrylate (15.0 g, 49.8 mmol) was dissolved in ethanol (30 ml), and to this solution, an ethanol (10 ml) solution of (S)-2-amino-1-propanol (4.50 g, 59.8 mmol) was added dropwise while stirring and cooling with ice. After completion of dripping, the reaction solution was stirred for 1 hour at room temperature and then concentrated under a reduced pressure. The residue obtained was dissolved in dimethyl sulfoxide (50 ml), and after adding spray-dried calcium fluoride (16 g) thereto, it was stirred at 120° C. for 26 hours. After letting the reaction suspension cool, the reaction suspension was concentrated under a reduced pressure, chloroform (200 ml) and water (200 ml) were added to the residue, and after performing a separation operation, the water layer was extracted using chloroform (200 ml). The combined organic layers were then washed with saturated saline solution (100 ml) and then dried over anhydrous sodium sulfate. After filtering, the filtrate was concentrated under a reduced pressure, the residue obtained was applied to a silica gel chromatography, and 5.60 g (39%) of the title compound was obtained as a white powder from a chloroform:methanol=50:1 eluate.

$^1$H-NMR (400 MHz, CDCl$_3$) δ: 1.41 (3H, t, J=7.1 Hz), 1.61 (3H, d, J=7.1 Hz), 4.33-4.44 (5H, m), 7.18 (1H, t, J=10.0 Hz), 8.06 (1H, dd, J=10.0, 5.4 Hz), 8.39 (1H, s).

Reference Example 24

10-fluoro-2,3-dihydro-3-(S)-methyl-7-oxo-7H-pyrido[1,2,3-de][1,4]benzoxazine-6-carboxylic acid A mixture of ethyl 10-fluoro-2,3-dihydro-3-(S)-methyl-7-oxo-7H-pyrido[1,2,3-de][1,4]benzoxazine-6-carboxylate (5.60 g, 19.2 mmol), acetic acid (25 ml) and concentrated hydrochloric acid (25 ml) was heated under reflux for 4 hours. After cooling the reaction solution with ice, water (100 ml) was added thereto, and the precipitated crystals were filtered out and then washed with excess water, a small amount of cold ethanol and excess diethyl ether in that order. The crude crystals obtained were then suspended in ethanol (40 ml) and stirred under room temperature. The crystals were filtered out, washed with ethanol, and then dried under a reduced pressure at 80° C. for 17 hours. 4.10 g (81%) of the title compound was thereby obtained in the form of a white powder.

$^1$H-NMR (400 MHz, DMSO-d$_6$) δ: 1.47 (3H, d, J=6.8 Hz), 4.44 (1H, d, J=9.6 Hz), 4.62 (1H, d, J=9.6 Hz), 4.99 (1H, q-like, J=6.8 Hz), 7.59 (1H, t, J=9.1 Hz), 7.95 (1H, dd, J=9.1, 5.4 Hz, 9.07 (1H, s). Elemental analysis: As C$_{13}$H$_{10}$FNO$_4$; Calcd.: C, 59.32%; H, 3.83%; N, 7.22%. Found: C, 59.60%; H, 3.95%; N, 6.99%.

Example 9

10-[3-(R)-(1-aminocyclopropyl)pyrrolidin-1-yl]-2,3-dihydro-3-(S)-methyl-7-oxo-7H-pyrido[1,2,3-de][1,4]benzoxazine-6-carboxylic acid After adding 3-(R)-[1-(tert-butoxycarbonylamino)cyclopropyl]pyrrolidine (252 mg, 1.12 mmol) and triethylamine (0.50 ml) to dried dimethyl sulfoxide (3 ml), 10-fluoro-2,3-dihydro-3-(S)-methyl-7-oxo-7H-pyrido[1,2,3-de][1,4]benzoxazine-6-carboxylic acid (244 mg, 928 μmol) was added thereto and stirred while heating in an oil bath of 100° C. for 18 hours under a nitrogen atmosphere. After concentrating the reaction solution under a reduce pressure, the residue was dissolved in chloroform (100 ml). After washing the organic layer with a 10% aqueous citric acid solution (50 ml) and saturated saline solution (50 ml), the organic layer was dried over anhydrous sodium sulfate. After filtering, the filtrate was concentrated under a reduced pressure, and after adding dropwise concentrated hydrochloric acid (6 ml) to the residue while cooling with ice, it was stirred at room temperature for 30 minutes. After adding 4 ml of water to the reaction solution and washing this acidic aqueous solution with chloroform (10 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evaporated under a reduced pressure. The residue thus obtained was purified by recrystallization from ethanol and then dried under a reduced pressure. 125 mg (36.5%) of the title compound was thereby obtained in the form of yellow crystals.

$^1$H-NMR (400 MHz, 0.1 mol/l NaOD) δ: 0.57 (4H, s), 1.54 (3H, d, J=6.80 Hz), 1.66-1.78 (1H, m), 2.01-2.11 (1H, m), 2.19-2.30 (1H, m), 3.38-3.60 (4H, m), 4.25 (1H, d, J=11.0 Hz), 4.47 (1H, d, J=11.0 Hz), 4.55-4.63 (1H, m), 7.11 (1H, d, J=9.03 Hz), 7.81 (1H, d, J=9.03 Hz), 8.32 (1H, s). IR (KBr, disk) ν: 1634, 1529, 1446, 1429, 1363, 1269, 1227, 798 cm$^{-1}$.

Melting point: 249 to 252° C. (decomposed) Elemental analysis: As C$_{20}$H$_{23}$N$_3$O$_4$.HCl0.5H$_2$O; Calcd.: C, 57.90%; H, 6.07%; N, 10.13%. Found: C, 57.65%; H, 5.87%; N, 9.97%.

Example 10

1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinoline-3-carboxylic acid After adding 3-(R)-[1-[N-(tert-butoxycarbonyl)-N-(methyl)amino]cyclopropyl]pyrrolidine (118 mg, 436 mmol) and triethylamine (0.50 ml) to dried dimethyl sulfoxide (1 ml), 7-fluoro-1-[2-(S)-fluoro-1-(R)-cyclopropyl]-8-methyl-1,4-dihydro-4-oxoquinoline-3-carboxylic acid (122 mg, 436 μmol) was added thereto and heated under reflux in an oil bath of 100° C. for 18 hours under a nitrogen atmosphere. After concentrating the reaction solution under a reduced pressure, the residue was dissolved in chloroform (100 ml). After washing the organic layer with a 10% aqueous citric acid solution (100 ml), the organic layer was dried over anhydrous sodium sulfate. After filtering, the filtrate was concentrated under a reduced pressure, and after adding dropwise concentrated hydrochloric acid (2 ml) to the residue while cooling with ice, it was stirred at room temperature for 30 minutes. After adding 1 mol/l hydrochloric acid (2 ml) to the reaction solution and washing the yellow acidic aqueous solution with chloroform (50 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evapolated under a reduced pressure. The residue thus obtained was then purified by a preparative chromatography (developed into the lower layer of a 7:3:1 mixture of chloroform:methanol:water), purified further by recrystallization from ethanol, and then dried under a reduced pressure. 72.8 mg (42%) of the title compound was thereby obtained in the form of yellow crystals.

$^1$H-NMR (400 MHz, 0.1 mol/l NaOD) δ: 0.59-0.64 (4H, m), 1.21-1.27 (1H, m), 1.50-1.64 (2H, m), 1.99-2.01 (1H, m), 2.34 (3H, s), 2.42 (3H, s), 2.87-2.89 (1H, m), 3.27-3.29 (3H, m), 3.63-3.65 (1H, m), 4.06-4.07 (1H, m), 5.05 (1H, dm, J=63.72 Hz), 7.09 (1H, m), 8.00 (1H, s), 8.44 (1H, s). IR (KBr, disk) ν: 3348, 3086, 2939, 2844, 2789, 1711, 1614, 1518, 1435, 1354, 1315, 1257, 1221 cm$^{-1}$.

Melting point: 223 to 224° C. Specific rotation: $[\alpha]_D^{24.7}$=−119.66° (c 0.295, 0.1 mol/l NaOH) Elemental analysis: As $C_{22}H_{26}FN_3O_3$; Calcd.: C, 66.15%; H, 6.56%; N, 10.52%. Found: C, 65.92%; H, 6.52%; N, 10.40%.

Example 11

1-[2-(S)-fluoro-1-(R)-cyclopropyl]-8-methoxy-7-[3-(R)-[1-(methylamino)cyclopropyl]pyrrolidin-1-yl]-1,4-dihydro-4-oxoquinoline-3-carboxylic acid After adding 3-(R)-[1-[N-(tert-butoxycarbonyl)-N-(methyl)amino]cyclopropyl]pyrrolidine (102 mg, 379 μmol) and triethylamine (0.50 ml) to dried dimethyl sulfoxide (1 ml), 7-fluoro-1-[2-(S)-fluoro-1-(R)-cyclopropyl]-1,4-dihydro-8-methoxy-4-oxoquinoline-3-carboxylic acid (112 mg, 379 μmol) was added thereto and stirred while heating in an oil bath of 100° C. for 15 hours under a nitrogen atmosphere. After concentrating the reaction solution under a reduced pressure, the residue was dissolved in chloroform (100 ml). After washing the organic layer with a 10% aqueous citric acid solution (100 ml), the organic layer was dried over anhydrous sodium sulfate. After filtering, the filtrate was concentrated under a reduced pressure, and after adding dropwise concentrated hydrochloric acid (2 ml) to the residue while cooling with ice, it was stirred at room temperature for 30 minutes. After adding 1 mol/l hydrochloric acid (2 ml) to the reaction solution and washing the yellow acidic aqueous solution with chloroform (50 ml×4), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evapolated under a reduced pressure. The residue thus obtained was then purified by a preparative chromatography (developed into the lower layer of a 7:3:1 mixture of chloroform:methanol:water), purified further by recrystallization from ethanol, and then dried under a reduced pressure. 78.3 mg (50%) of the title compound was thereby obtained in the form of yellow crystals.

$^1$H-NMR (400 MHz, 0.1 mol/l NaOD) δ: 0.57-0.61 (4H, m), 1.33-1.40 (1H, m), 1.56-1.58 (2H, m), 1.99-2.01 (1H, m), 2.34 (3H, s), 2.87-2.89 (1H, m), 3.15-3.17 (1H, m), 3.52-3.54 (3H, m), 3.53 (3H, s), 4.00-4.02 (1H, m), 5.02 (1H, dm, J=64.45 Hz), 7.03 (1H, s), 7.92 (1H, d, J=7.03 Hz), 8.39 (1H, s). IR (KBr, disk) ν: 3352, 3095, 3051, 2939, 2837, 2787, 1716, 1699, 1616, 1520, 1439, 1358, 1319, 1259, 1221 cm$^{-1}$.

Melting point: 213 to 215° C. Specific rotation: $[\alpha]_D^{24.7}$=−38.46° (c 0.195, 0.1 mol/l NaOH) Elemental analysis: As $C_{22}H_{26}FN_3O_4$; Calcd.: C, 63.60%; H, 6.31%; N, 10.11%. Found: C, 63.36%; H, 6.31%; N, 9.97%.

Example 12

5-amino-1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinoline-3-carboxylic acid After adding 3-(R)-[1-[N-(tert-butoxycarbonyl)-N-(methyl)amino]cyclopropyl]pyrrolidine (690 mg, 2.25 mmol) and triethylamine (0.50 ml) to dried dimethyl sulfoxide (4 ml), 5-amino-7-fluoro-1-[2-(S)-fluoro-1-(R)-cyclopropyl]-8-methyl-1,4-dihydro-4-oxoquinoline-3-carboxylic acid (250 mg, 850 μmol) was added thereto and heated under reflux in an oil bath of 70° C. for 24 hours under a nitrogen atmosphere. After concentrating the reaction solution under a reduced pressure, the residue was dissolved in chloroform (100 ml). After washing the organic layer with a 10% aqueous citric acid solution (100 ml) and saturated saline solution (100 ml), the organic layer was dried over anhydrous sodium sulfate. After filtering, the filtrate was concentrated under a reduced pressure, and after adding dropwise concentrated hydrochloric acid (5 ml) to the residue while cooling with ice, it was stirred at room temperature for 30 minutes. After adding 1 mol/l hydrochloric acid (2 ml) to the reaction solution and washing the yellow acidic aqueous solution with chloroform (50 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evapolated under a reduced pressure. The residue thus obtained was then purified by preparative chromatography (developed into the lower layer of a 7:3:1 mixture of chloroform:methanol:water), purified further by recrystallization from ethanol, and then dried under a reduced pressure. 70.0 mg (20%) of the title compound was thereby obtained in the form of yellow crystals.

$^1$H-NMR (400 MHz, 0.1 mol/l NaOD) δ: 0.56-0.64 (4H, m), 1.21-1.61 (3H, m), 1.92-1.96 (1H, m), 2.22 (3H, s), 2.45 (3H, s), 2.68-2.73 (1H, m), 3.19-3.31 (3H, m), 3.59-3.66 (1H, m), 3.72-3.77 (1H, m), 4.76-4.78 (0.5H, m), 4.98-5.01 (0.5H, m), 5.97 (1H, s), 8.55 (1H, d, J=3.66 Hz). IR (KBr, disk) ν: 3440, 3329, 3082, 3005, 2964, 2937, 2877, 1716, 1620, 1549, 1506, 1437, 1404 cm$^{-1}$.

Melting point: 129 to 131° C. Specific rotation: $[\alpha]_D^{22.6}$=−291.90° (c 0.285, 0.1 mol/l NaOH) Elemental analysis: As $C_{21}H_{25}FN_4O_3 \cdot 0.25H_2O$; Calcd.: C, 63.07%; H, 6.62%; N, 13.37%. Found: C, 62.89%; H, 6.42%; N, 13.27%.

Example 13

2,3-dihydro-3-(S)-methyl-10-[3-(R)-[1-(methylamino)cyclopropyl]pyrrolidin-1-yl]-7-oxo-7H-pyrido[1,2,3-de][1,4]benzoxazine-6-carboxylic acid After adding 3-(R)-[1-[N-(tert-butoxycarbonyl)-N-(methyl)amino]cyclopropyl]pyrrolidine (125 mg, 521 μmol) and triethylamine (0.50 ml) to dried dimethyl sulfoxide (1 ml), 10-fluoro-2,3-dihydro-3-(S)-methyl-7-oxo-7H-pyrido[1,2, 3-de][1,4]benzoxazine-6-carboxylic acid (132 mg, 500 μmol) was added thereto and stirred while heating in an oil bath of 100° C. for 20 hours under a nitrogen atmosphere. After concentrating the reaction solution under a reduced pressure, the residue was dissolved in chloroform (100 ml). After washing the organic layer with a 10% aqueous citric acid solution (50 ml) and saturated saline solution (50 ml), the organic layer was dried over anhydrous sodium sulfate. After filtering, the filtrate was concentrated under a reduced pressure, and after adding concentrated hydrochloric acid (3 ml) to the residue while cooling with ice, it was stirred at room temperature for 30 minutes. After adding water (3 ml) to the reaction solution and washing the yellow acidic aqueous solution with chloroform (50 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evaporated under a reduced pressure. The residue thus obtained was then purified by recrystallization from ethanol-ammonia water and then dried under a reduced pressure. 135 mg (70%) of the title compound was thereby obtained in the form of yellow crystals.

$^1$H-NMR (400 MHz, 0.1 mol/l NaOD) δ: 0.56-0.60 (4H, m), 1.45-1.50 (1H, m), 1.52 (3H, d, J=6.59 Hz), 1.99-2.01 (1H, m), 2.32 (3H, s), 2.86-2.88 (1H, m), 3.21-3.55 (4H, m), 4.22, 4.45 (each 1H, ABq, J=11.36 Hz), 4.57-4.59 (1H, m), 7.04-7.08 (1H, m), 7.80 (1H, d, J=9.03 Hz), 8.32 (1H, s).

Melting point: 227 to 229° C. Specific rotation: $[\alpha]_D^{24.7}$=−131.00° (c 0.200, 0.1 mol/l NaOH) Elemental analysis: As $C_{21}H_{25}N_3O_4$; Calcd.: C, 65.78%; H, 6.57%; N, 10.96%. Found: C, 65.49%; H, 6.55%; N, 10.82%.

Example 14

7-[3-(R)-[1-(ethylamino)cyclopropyl]pyrrolidin-1-yl]-1-[2-(S)-fluoro-1-(R)-cyclopropyl]-8-methyl-1,4-dihydro-4-oxoquinoline-3-carboxylic acid After adding 3-(R)-[1-[N-(tert-butoxycarbonyl)-N-(ethyl) amino]cyclopropyl]pyrrolidine (2.16 g, 8.40 mmol) and triethylamine (4 ml) to dried dimethyl sulfoxide (10 ml), 7-fluoro-1-[2-(S)-fluoro-1-(R)-cyclopropyl]-8-methyl-1,4-dihydro-4-oxoquinoline-3-carboxylic acid (1.95 g, 7.00 mmol) was added thereto and heated under reflux in an oil bath of 100° C. for 51 hour under a nitrogen atmosphere. After concentrating the reaction solution under a reduced pressure, the residue was dissolved in chloroform (150 ml). After washing the organic layer with a 10% aqueous citric acid solution (100 ml) and saturated saline solution (100 ml), the organic layer was dried over anhydrous sodium sulfate. After filtering, the filtrate was concentrated under a reduced pressure, and after adding dropwise concentrated hydrochloric acid (10 ml) to the residue while cooling with ice, it was stirred at room temperature for 30 minutes. After adding 1 mol/l hydrochloric acid (20 ml) to the reaction solution and washing the yellow acidic aqueous solution with chloroform (100 ml×5), the pH was adjusted to 12.0 with an aqueous sodium hydroxide solution. After adjusting the pH of the basic aqueous solution to 7.4 with 1 mol/l hydrochloric acid, extraction with chloroform (150 ml×4) was performed. After drying over anhydrous sodium sulfate, the solvent was evaporated under a reduced pressure. The residue thus obtained was purified by recrystallization from ethanol and then dried under a reduced pressure. 1.61 g (55%) of the title compound was thereby obtained in the form of yellow crystals.

$^1$H-NMR (400 MHz, 0.1 mol/l NaOD) δ: 0.57-0.63 (4H, m), 1.04 (3H, t, J=6.95 Hz), 1.19-1.25 (1H, m), 1.47-1.64 (2H, m), 1.97-1.98 (1H, m), 2.40 (3H, s), 2.70-2.73 (2H, m), 2.86-2.87 (1H, m), 3.26-3.28 (3H, m), 3.61-3.63 (1H, m), 4.02-4.05 (1H, m), 5.03 (1H, dm, J=64.11 Hz), 7.07 (1H, d, J=9.26 Hz), 7.98 (1H, d, J=9.26 Hz), 8.43 (1H, d, J=3.41 Hz). IR (KBr, disk) ν: 3294, 2964, 2848, 1699, 1612, 1508, 1473, 1431, 1396, 1389, 1350, 1308, 1261 cm$^{-1}$.

Melting point: 191 to 194° C. Specific rotation: $[\alpha]_D^{24.3}$=−236.55° (c 0.145, 0.1 mol/l NaOH) Elemental analysis: As $C_{23}H_{28}FN_3O_3$; Calcd.: C, 66.81%; H, 6.83%; N, 10.16%. Found: C, 66.52%; H, 6.86%; N, 10.03%.

Example 15

1-(cyclopropyl)-8-methyl-7-[3-(R)-[1-(methylamino) cyclopropyl]pyrrolidin-1-yl]-1,4-dihydro-4-oxo-quinoline-3-carboxylic acid After adding 3-(R)-[1-[N-(tert-butoxycarbonyl)-N-(methyl)amino]cyclopropyl]pyrrolidine (880 mg, 3.25 mmol) and triethylamine (1.0 ml) to dried dimethyl sulfoxide (5 ml), 1-cyclopropyl-7-fluoro-8-methyl-1,4-dihydro-4-oxoquinoline-3-carboxylic acid (425 mg, 1.63 mmol) was added thereto and heated under reflux in an oil bath of 70° C. for 38 hours under a nitrogen atmosphere. After concentrating the reaction solution under a reduced pressure, the residue was dissolved in ethyl acetate (200 ml). After washing the organic layer with a 10% aqueous citric acid solution (100 ml), the organic layer was dried over anhydrous sodium sulfate. After filtering, the filtrate was concentrated under a reduced pressure, and after adding dropwise concentrated hydrochloric acid (6 ml) to the residue while cooling with ice, it was stirred at room temperature for 30 minutes. After adding 1 mol/l hydrochloric acid (12 ml) to the reaction solution and washing the yellow acidic aqueous solution with chloroform (50 ml×3), the pH was adjusted to 12.0 with an aqueous sodium hydroxide solution. After adjusting the pH of the basic aqueous solution to 7.4 with 1 mol/l hydrochloric acid, extraction with chloroform (100 ml×3) was performed. After drying over anhydrous sodium sulfate, the solvent was evaporated under a reduced pressure. The residue thus obtained was then purified by recrystallization from a mixed solvent of methanol/2-propanol, and then dried under a reduced pressure. 331 mg (53%) of the title compound was thereby obtained in the form of yellow crystals.

$^1$H-NMR (400 MHz, CDCl$_3$) δ: 0.57-0.65 (1H, m), 0.87-0.92 (1H, m), 0.97-1.04 (1H, m), 1.11-1.18 (1H, m), 1.28-1.34 (1H, m), 1.64-1.71 (1H, m), 1.99-2.021H, m), 2.45 (3H, s), 2.50 (3H, s), 2.71-2.76 (1H, m), 3.32-3.36 (3H, m), 3.64-3.70 (1H, m), 4.01-4.05 (1H, m), 6.99 (1H, d, J=9.06 Hz), 8.131H, d, J=9.06 Hz), 8.85 (1H, s).

Melting point: 190 to 192° C. Elemental analysis: As $C_{22}H_{27}N_3O_3$; Calcd.: C, 69.27%; H, 7.13%; N, 11.02%. Found: C, 69.00%; H, 7.16%; N, 10.96%.

Reference Example 25

Ethyl 1-(2-bromoacetyl)cyclopropanecarboxylate

Ethyl 1-acetylcyclopropanecarboxylate (200 g, 1.28 mol) was dissolved in ethanol (1000 ml), and bromine (72.7 ml, 1.41 mol) was added dropwise while stirring and cooling with ice. After completion of dripping, the temperature of the reaction solution was raised to 30° C. and stirring was performed for 2 hours. After adding water (1000 ml) to the reaction solution while cooling with ice, it was concentrated under a reduced pressure was performed. After extracting the concentrate into ethyl acetate (750 ml×2), it was washed with a 10% aqueous sodium thiosulfate solution (500 ml×2) and saturated sodium bicarbonate water (500 ml×2) in that order and then dried over anhydrous sodium sulfate. After filtering and concentrating the filtrate under a reduced pressure, 291 g (97%) of the title compound was obtained as a yellow, oily substance.

$^1$H-NMR (400 MHz, CDCl$_3$) δ: 1.30 (3H, t, J=7.1 Hz), 1.60-1.63 (4H, m), 4.22 (2H, q, J=7.1 Hz), 4.49 (2H, s). TLC: Rf=0.7 (n-hexane:ethyl acetate=3:1)

Reference Example 26

Diethylphosphonoacetic acid

Ethyl diethylphosphonoacetate (100 g, 446 mmol) was dissolved in ethanol (275 ml), and after adding dropwise a 2 mol/l aqueous sodium hydroxide solution (275 ml, 550 mmol) while stirring and cooling with ice, it was stirred at room temperature for 1 hour. The reaction solution was then concentrated under a reduced pressure, and the concentrate was made acidic by concentrated hydrochloric acid while cooling with ice. Extractions into ethyl acetate (200 ml×4), chloroform (100 ml×2) and 5% methanol/chloroform (250 ml×2) were then performed. The combined organic layers were then dried over anhydrous sodium sulfate, and after filtering, the filtrate was concentrated under a reduced pressure. 89 g (quantitative) of the title compound was thereby obtained as a colorless, oily substance.

$^1$H-NMR (400 MHz, CDCl$_3$) δ: 1.35 (6H, t, J=6.8 Hz), 2.98 (2H, d, J=21.7 Hz), 4.19 (4H, q, J=6.8 Hz). TLC: Rf=0.1 (chloroform:methanol=9:1)

Reference Example 27

Ethyl 1-[2-[N-[1-(S)-phenylethyl]amino]acetyl]cyclopropanecarboxylate 1-(S)-phenylethylamine (12.1 g, 100 mmol) was dissolved in acetonitrile (120 ml), and an acetonitrile (50 ml) solution of triethylamine (15.3 ml, 110 mmol) and ethyl 1-(2-bromoacetyl) cyclopropanecarboxylate (23.5 g, 100 mmol) was added dropwise in while stirring and cooling with ice. After completion of dripping, the reaction solution was stirred while cooling with ice for 1.5 hours. The reaction solution was then poured into water (75 ml) and concentrated under a reduced pressure. The concentrate was subjected to extraction with diisopropyl ether (75 ml×2) and then washed with water (75 ml). After extracting the organic layer into 1 mol/l hydrochloric acid (100 ml×2), the acidic aqueous solution was washed with ethyl acetate (100 ml). After adding a 1 mol/l aqueous sodium hydroxide solution (100 ml) to this acidic aqueous solution and then further adding saturated sodium bicarbonate water (100 ml), extraction with ethyl acetate (100 ml) was performed. The organic layer was then washed with water (100 ml) and saturated saline solution (100 ml) in that order, and then dried over anhydrous sodium sulfate. After filtering and then concentrating the filtrate under a reduced pressure, 18.6 g (68%) of the title compound was obtained as a pale-yellow, oily substance.

$^1$H-NMR (400 MHz, CDCl$_3$) δ: 1.17 (3H, t, J=7.1 Hz), 1.38 (3H, d, J=6.6 Hz), 1.48 (4H, s), 3.71 (1H, q, J=6.6 Hz), 3.86 (2H, d, J=2.0 Hz), 4.10 (2H, q, J=7.1 Hz). TLC: Rf=0.6 (n-hexane:ethyl acetate=1:1)

Reference Example 28

Ethyl 1-[2-[N-(diethylphosphonoacetyl)-N-[1-(S)-phenylethyl]amino]acetyl]cyclopropanecarboxylate Method A:

Diethylphosphonoacetic acid (15.1 g, 76.8 mmol) was dissolved in anhydrous tetrahydrofuran (120 ml), and after adding 1,1'-carbonyldiimidazole (13.7 g, 84.5 mmol) while cooling with ice, it was stirred at room temperature for 1 hour. After adding an anhydrous tetrahydrofuran (30 ml) solution of ethyl 1-[2-[N-[1-(S)-phenylethyl]amino]acetyl]cyclopropanecarboxylate (17.6 g, 64.0 mmol) to the reaction solution while cooling with ice, it was stirred at room temperature for 1 hour. After adding 1 mol/l hydrochloric acid (100 ml) and ethyl acetate (100 ml) to the reaction solution and performing an extraction operation, the organic layer was separated. The aqueous layer was then subjected to extraction with ethyl acetate (100 ml) and the combined organic layer was washed with saturated sodium bicarbonate water (100 ml) and saturated saline solution (100 ml) in that order, and then dried over anhydrous sodium sulfate. After filtering and then concentrating the filtrate under a reduced pressure, 28.7 g (99%) of the title compound was obtained as a yellow syrup.

Method B

Diethylphosphonoacetic acid (32.8 g, 166 mmol) was dissolved in anhydrous benzene (700 ml), and after adding N,N'-dimethylformamide (1 ml, thionyl chloride (18.2 ml, 250 mmol) was added thereto and heated under reflux for 1.5 hours. After letting the reaction solution cool, it was concentrated under a reduced pressure, and after adding dried toluene (100 ml) thereto, its concentration under a reduced pressure was performed again. After repeating this operation 3 times, the concentrate was dissolved in anhydrous tetrahydrofuran (300 ml) and after adding dropwise an anhydrous tetrahydrofuran (300 ml) solution of ethyl 1-[2-[N-[1-(S)-phenylethyl]amino]acetyl]cyclopropanecarboxylate (45.7 g, 166 mmol) and triethylamine (25.1 ml, 183 mmol) while stirring and cooling with ice, it was stirred while cooling with ice for 1.5 hours and then stirred at room temperature for 2 hours. After adding 1 mol/l hydrochloric acid (300 ml) and ethyl acetate (300 ml) to the reaction solution and performing an extraction operation, the organic layer was separated. The aqueous layer was then subjected to extraction with ethyl acetate (300 ml) and the combined organic layer was washed with saturated sodium bicarbonate water (300 ml) and saturated saline solution (300 ml) in that order, and then dried over anhydrous sodium sulfate. After filtering and then concentrating the filtrate under a reduced pressure, 43.6 g (70%) of the title compound was obtained as a yellow syrup.

$^1$H-NMR (400 MHz, CDCl$_3$) δ: 1.14, 1.20 (3H, t, J=7.1 Hz), 1.29-1.68 (13H, m), 2.85, 4.69 (2H, dd, J=9.5, 20.7 Hz), 3.18, 4.55 (2H, d, J=22.2 Hz), 4.06-4.22 (6H, m), 5.42, 6.05 (1H, q, J=7.1 Hz), 7.26-7.37 (5H, m). MS (m/z): 454 ([M+H])$^+$ TLC: Rf=0.1 (n-hexane:ethyl acetate=1:1)

Reference Example 29

4-(1-ethoxycarbonylcyclopropyl)-1-[1-(S)-phenylethyl]-3-pyrrolin-2-one

After dissolving ethyl 1-[2-[N-(diethylphosphonoacetyl)-N-[1-(S)-phenylethyl]amino]acetyl]cyclopropanecarboxylate (25.0 g, 55.2 mmol) in toluene (250 ml), tert-butoxypotassium (7.40 g, 66.2 mmol) was added gradually while stirring and cooling with ice. After stirring the reaction solution for 15 minutes at room temperature, a 10% aqueous citric acid solution (250 ml) and ethyl acetate (250 ml) were added thereto, and after performing an extraction operation, the organic layer was separated. The aqueous layer was then subject to extraction with ethyl acetate (250 ml), and after washing the combined organic layer with saturated sodium bicarbonate water (250 ml) and saturated saline solution (250 ml) in that order, the organic layer was dried over anhydrous sodium sulfate. After filtering, the filtrate was concentrated under a reduced pressure, the concentrate was applied to a silica gel chromatography, and 12.1 g (73%) of the title compound was obtained as a orange syrup from an n-hexane:ethyl acetate=2:1 to 1:2 eluate. The instrumental analysis data for this resulting compound agreed with the data indicated in PCT/JP96/00208.

$^1$H-NMR (400 MHz, CDCl$_3$) δ: 1.18, (3H, t, J=7.2 Hz), 1.60-1.63 (7H, m), 3.80 (1H, dd, J=1.5, 9.0 Hz), 4.07-4.11 (2H, m), 4.13 (1H, d, J=9.0 Hz), 5.55 (1H, q, J=7.1 Hz), 5.84 (1H, t, J=1.5 Hz), 7.24-7.36 (5H, m). MS (m/z): 300 ([M+H])$^+$TLC: Rf=0.5 (n-hexane:ethyl acetate=1:1)

Reference Example 30

4-(S)-(1-ethoxycarbonylcyclopropyl)-1-[1-(S)-phenylethyl]pyrrolidin-2-one 4-(1-ethoxycarbonylcyclopropyl)-1-[1-(S)-phenylethyl]-3-pyrrolin-2-one (12.1 g, 40.5 mmol) was dissolved in ethyl acetate (120 ml), a 5% platinum carbon catalyst (water content: 50%, 2.4 g) was added thereto, and it was stirred at room temperature for 17 hours under a hydrogen atmosphere at atmospheric pressure. The reaction solution was then filtered through celite (washed with ethyl acetate) and the filtrate was then concentrated under a reduced pressure. The concentrate was applied to a silica gel chromatography, and 9.00 g (74%) of the compound of the title were obtained as a pale-yellow syrup from an n-hexane:ethyl acetate=3:2 eluate. Further, 2.60 g (21%) of the diastereomer (4-(R)-isomer) of the title compound was obtained as a pale-yellow syrup. The instrumental analysis data for this resulting compound agreed with the data indicated in PCT/JP96/00208.

4-(S)-isomer:
$^1$H-NMR (4000 MHz, CDCl$_3$) δ: 0.63-0.65 (2H, m), 1.13 (3H, t, J=7.1 Hz), 1.12-1.19 (2H, m), 1.52 (3H, d, J=7.3 Hz), 2.17 (1H, dd, J=9.0, 16.8 Hz), 2.46 (1H, dd, J=9.3, 16.3 Hz), 2.67-2.76 (2H, m), 3.47 (1H, t, J=8.3 Hz), 3.96-4.11 (2H, m), 5.51 (1H, q, J=7.3 Hz), 7.26-7.35 (5H, m). TLC: Rf=0.45 (n-hexane:ethyl acetate=1:1)

4-(R)-isomer:
$^1$H-NMR (400 MHz, CDCl$_3$) δ: 0.72-0.76 (2H, m), 1.18-1.24 (2H, m), 1.21 (3H, t, J=7.1 Hz), 1.52 (3H, d, J=7.1 Hz), 2.27-2.32 (1H, m), 2.44-2.52 (2H, m), 3.14 (2H, d, J=8.0 Hz), 4.10 (2H, q, J=7.1 Hz), 5.50 (1H, q, J=7.1 Hz), 7.26-7.35 (5H, m). TLC: Rf=0.5 (n-hexane:ethyl acetate=1:1)

Reference Example 31

1-[1-[1-(S)-phenylethyl]-2-one-4-(S)-pyrrolidin-4-yl]-1-cyclopropanecarboxylic acid 4-(S)-(1-ethoxycarbonylcyclopropyl)-1-[1-(S)-phenylethyl]pyrrolidin-2-one (10.5 g, 34.9 mmol) was dissolved in 70 ml of ethanol, and after adding a 1 mol/l aqueous sodium hydroxide solution (70 ml) while cooling with ice, the reaction solution was stirred at room temperature for 15.5 hours and then at 40° C. for 3 hours. After concentrating the reaction solution under a reduced pressure, the remaining aqueous layer was washed with ethyl acetate (70 ml). The aqueous layer was then made acidic by concentrated hydrochloric acid while cooling with ice and then subjected to extraction with chloroform (70 ml×3). The organic layer was then dried over anhydrous sodium sulfate, and after filtering, the filtrate was concentrated under a reduced pressure. 9.40 g (99%) of the title compound was thereby obtained as white solids.

$^1$H-NMR (400 MHz, CDCl$_3$) δ: 0.72-0.74 (2H, m), 1.21-1.23 (2H, m), 1.52 (3H, d, J=7.3 Hz), 2.17 (1H, dd, J=8.8, 16.8 Hz), 2.48 (1H, dd, J=9.5, 16.8 Hz), 2.66-2.78 (2H, m), 3.50 (1H, t, J=9.3 Hz), 5.51 (1H, q, J=7.3 Hz), 7.25-7.34 (5H, m).

Reference Example 32

4-(R)-[1-(tert-butoxycarbonylamino)cyclopropyl]-1-[1-(S)-phenylethyl]pyrrolidin-2-one A toluene (15 ml) solution of triethylamine (9.6 ml, 69 mmol) and diphenylphosphoric acid azide (DPPA; 10.4 g, 37.9 mmol) was added to a toluene (80 ml) suspension of 1-[1-[1-(S)-phenylethyl]-2-one-4-(S)-pyrrolidin-4-yl]-1-cyclopropanecarboxylic acid (9.4 g, 34.4 mmol), and after stirring at room temperature for 1 hour under a nitrogen atmosphere, it was heated under reflux for 1.5 hours. After cooling the reaction solution to room temperature, tert-butyl alcohol (95 ml) was added thereto and heated under reflux for 15 hours. After letting the reaction solution cool, the reaction solution was concentrated under a reduced pressure and ethyl acetate (95 ml) and water (95 ml) were added to the concentrate. After performing an extraction operation, the organic layer was separated and the aqueous layer was subjected to extraction with ethylacetate (95 ml). The combined organic layer was then washed with saturated saline solution (95 ml) and then dried over anhydrous sodium sulfate. After filtering and concentrating the filtrate under a reduced pressure, the concentrate was applied to a silica gel chromatography and 10.7 g (90%) of the title compound was obtained as a colorless, amorphous substance from a chlorine:methanol=50:1 eluate.

$^1$H-NMR (400 MHz, CDCl$_3$) δ: 0.56-0.85 (4H, m), 1.37 (9H, s), 1.51 (3H, d, J=7.3 Hz), 2.32-2.44 (3H, m), 2.79 (1H, dd, J=7.3, 10.0 Hz), 3.36 (1H, m), 4.66 (1H, brs), 5.50 (1H, q, J=7.3 Hz), 7.26-7.34 (5H, m). TLC: Rf=0.15 (n-hexane:ethyl acetate=1:1)

Reference Example 33

3-(R)-[1-(tert-butoxycarbonylamino)cyclopropyl]-1-[1-(S)-phenylethyl]pyrrolidine 4-(R)-[1-(tert-butoxycarbonylamino)cyclopropyl]-1-[1-(S)-phenylethyl]pyrrolidin-2-one (10.4 g, 30.2 mmol) was dissolved in anhydrous tetrahydrofuran (100 ml) and a 1.0M borane-tetrahydrofuran complex/tetrahydrofuran solution (90.7 ml, 90.7 mmol) was added dropwise gradually thereto under a nitrogen atmosphere while cooling with ice. After completion of dripping, it was stirred for 16 hours under the condition of from ice-cooling to room temperature. After slowly adding an aqueous solution (100 ml) of potassium carbonate (25.0 g, 181 mmol) to the reaction solution while cooling with ice, it was heated under reflux was for 1.5 hours. After letting the reaction solution cool, it was extracted with ethyl acetate (10 ml×2) and then washed with saturated saline solution (100 ml) The organic layer was then dried over anhydrous sodium sulfate, and after filtering, the filtrate was concentrated under a reduced pressure. The concentrate was applied to a silica gel chromatography and 8.20 g (82%) of the title compound was obtained in the form of colorless crystals from a chloroform:methanol=100:1 to 30:1 eluate.

$^1$H-NMR (400 MHz, CDCl$_3$) δ: 0.62 (2H, brs), 0.75-0.88 (2H, m), 1.35 (3H, d, J=6.6 Hz), 1.41 (9H, s), 1.63 (2H, m), 1.88-1.92 (1H, m), 2.14-2.17 (1H, m), 2.27-2.34 (2H, m), 2.63 (1H, brs), 3.15 (1H, t-like, J=6.6 Hz), 5.10 (1H, brs), 7.23-7.33 (5H, m). MS (m/z): 331 ([M+H])$^+$TLC: Rf=0.4 (chloroform:methanol=9:1)

Reference Example 34

3-(R)-[1-(tert-butoxycarbonylamino)cyclopropyl]pyrrolidine 3-(R)-[1-(tert-butoxycarbonylamino)cyclopropyl]-1-[1-(S)-phenylethyl]pyrrolidine (270 mg, 0.817 mmol) was dissolved in ethanol (15 ml), and after adding a 10% palladium carbon catalyst (water content: 52.0%; 270 mg), it was stirred at 40° C. for 3 hours under a hydrogen atmosphere at atmospheric pressure. After removing the catalyst by filtering (ethanol washing), the filtrate was concentrated under a reduced pressure, and as a result, 185 mg (quantitative) of the title compound was obtained in the form of a colorless syrup.

$^1$H-NMR (400 MHz, CDCl$_3$) δ: 0.69 (2H, brs), 0.79 (2H, brs), 1.42 (9H, s), 1.43-1.50 (1H, m), 1.86-1.88 (1H, m), 2.15-2.19 (1H, m), 2.68-2.72 (1H, m), 2.90-3.07 (3H, m), 4.92 (1H, brs).

Reference Example 35

1-benzyloxycarbonyl-3-(R)-[1-(tert-butoxycarbonylamino)cyclopropyl]pyrrolidine 3-(R)-[1-(tert-butoxycarbonylamino)cyclopropyl]-1-[1-(S)-phenylethyl]pyrrolidine (1.70 g, 5.15 mmol) was dissolved in dichloromethane (34 ml), and benzylchloroformate (1.10 ml, 7.73 mmol) was added dropwise while stirring and cooling with ice. The reaction solution was then stirred at room temperature for 2.5 hours and then stirred at 40° C. for 1.5 hours. After letting the reaction solution cool, the reaction solution was concentrated under a reduced pressure, the concentrate was applied to a silica gel chromatography, and 1.40 g (75%) of the title compound was obtained in the form of a colorless syrup from an n-hexane:ethyl acetate=2:1 eluate. The instrumental analysis data for this resulting compound agreed with the data indicated in PCT/JP96/00208.

$^1$H-NMR (400 MHz, CDCl$_3$) δ: 0.70 (2H, brs), 0.80 (2H, brs), 1.41 (9H, s), 1.63 (1H, m), 1.92 (1H, m), 2.25 (1H, m), 3.07-3.12 (1H, m), 3.29-3.31 (1H, m), 3.56 (2H, m), 4.85 (1H, brs), 5.12 (2H, s), 7.33-7.36 (5H, m). TLC: Rf=0.4 (n-hexane:ethyl acetate=1:1)

Reference Example 36

1-benzyloxycarbonyl-3-(R)-[1-[N-(tert-butoxycarbonyl)-N-(methyl)amino]cyclopropyl]pyrrolidine 1-benzyloxycarbonyl-3-(R)-[1-(tert-butoxycarbonylamino)cyclopropyl]pyrrolidine (1.40 g, 3.89 mmol), N,N'-dimethylformamide (7 ml), silver oxide (9.0 g, 39 mmol) and methyl iodide (24 ml, 389 mmol) were placed in a shaded and sealed tube, and this mixture was stirred for 13 hours in an oil bath of 80° C. The reaction solution was then filtered through cellite (ethyl acetate washing) and the filtrate was then diluted with ethyl acetate (100 ml). The organic layer was then washed with water (50 ml×3) and saturated saline solution (50 ml) in that order, and dried over anhydrous sodium sulfate. After filtering, the filtrate was concentrated under a reduced pressure, the concentrate was applied to a silica gel chromatography, and 1.31 g (89%) of the title compound was obtained in the form of a pale-yellow syrup an n-hexane:ethyl acetate=2:1 eluate. The instrumental analysis data for this resulting compound agreed with the data indicated in PCT/JP96/00208.

$^1$H-NMR (400 MHz, CDCl$_3$) δ: 0.83 (4H, brs), 1.42 (9H, s), 1.55 (1H, m), 1.88 (1H, m), 2.28-2.43 (1H, m), 2.83 (3H, s), 3.02-3.04 (1H, m), 3.25-3.33 (1H, m), 3.55 (2H, m), 5.12 (2H, s), 7.32-7.35 (5H, m). MS (m/Z): 374 ([M+H])$^+$TLC: Rf=0.4 (n-hexane:ethyl acetate=1:1)

Reference Example 37

3-(R)-[1-[N-(tert-butoxycarbonyl)-N-(methyl)amino]cyclopropyl]pyrrolidine 1-benzyloxycarbonyl-3-(R)-[1-[N-(tert-butoxycarbonyl)-N-(methyl)amino]cyclopropyl]pyrrolidine (1.31 g, 3.48 mmol) was dissolved in ethanol (13 ml), and after adding a 10% palladium carbon catalyst (water content: 50%; 0.65 g) thereto, it was stirred at room temperature for 5 hours under a hydrogen atmosphere at atmospheric pressure. After performing filtration through cellite (ethanol washing), the filtrate was concentrated under a reduced pressure. As a result, 0.92 g (quantitative) of the title compound was obtained in the form of a colorless syrup.

$^1$H-NMR (400 MHz, CDCl$_3$) δ: 0.80 (4H, brs), 1.46 (9H, s), 1.81 (1H, m), 2.04 (1H, brs), 2.28-2.42 (1H, m), 2.54 (1H, brs), 2.84 (3H, s), 2.88-2.96 (3H, m). TLC: Rf=0.1 (chloroform:methanol=9:1)

Reference Example 38

3-(R)-[1-[N-(tert-butoxycarbonyl)-N-(methyl)amino]cyclopropyl]-1-[1-(S)-phenylethyl]pyrrolidin-2-one 4-(R)-[1-(tert-butoxycarbonylamino)cyclopropyl]-1-[1-(S)-phenylethyl]pyrrolidin-2-one (7.87 g, 22.8 mmol) was dissolved in dimethylformamide (100 ml), and while cooling with ice, 60% oily sodium hydride (1.10 g, 27.4 mmol) was added and stirred for 5 minutes. Then, methyl iodide (7.11 ml, 114 mmol) was added dropwise thereto while stirring at room temperature. After completion of dripping, the reaction suspension was stirred at room temperature for 14 hours. After adding 60% oily sodium hydride (296 mg, 7.40 mmol) and methyl iodide (1.00 ml, 16.1 mmol), it was stirred at 40° C. for 24 hours. After adding a saturated aqueous ammonium chloride solution (100 ml) and water (150 ml) to the reaction suspension while stirring and cooling with ice, extraction with ethyl acetate (300 ml×2) was performed. The combined organic layer was then washed with water (100 ml×2) and saturated saline solution (100 ml×2) in that order, and then dried over anhydrous sodium sulfate. After filtering, the filtrate was concentrated under a reduced pressure, the residue obtained was applied to a silica gel chromatography, and 7.53 g (92%) of the title compound was obtained in the form of a colorless oily substance from a chloroform:methanol=50 to 30:1 eluate.

$^1$H-NMR (400 MHz, CDCl$_3$) δ: 0.83 (4H, m), 1.32 (6H, s), 1.38 (3H, s), 1.51 (3H, d, J=7.1 Hz), 1.61 (3H, d, J=16.6 Hz), 2.43 (1H, m), 2.68-2.81 (3H, m), 3.21 (1H, m), 5.48-5.50 (1H, m), 7.26-7.36 (5H, m).

Reference Example 39

3-(R)-[1-[N-(tert-butoxycarbonyl)-N-(methyl)amino]
cyclopropyl]-1-[1-(S)-phenylethyl]pyrrolidine 3-(R)-[1-[N-(tert-butoxycarbonyl)-N-(methyl)amino]cyclopropyl]-1-[1-(S)-phenylethyl]pyrrolidin-2-one (7.53 g, 21.0 mmol) was dissolved in anhydrous tetrahydrofuran (70 ml) and a 1.0M borane-tetrahydrofuran complex/tetrahydrofuran solution (63.0 ml, 63.0 mmol) was added dropwise gradually thereto while stirring and cooling with ice. After completion of dripping, it was stirred at room temperature for 20 hours. After slowly adding an aqueous solution (72 ml) of potassium carbonate (7.22 g) while cooling with ice, it was heated under reflux for 1.5 hours. After letting the reaction solution cool to room temperature, water (150 ml) was added, extraction with ethyl acetate (200 ml×2) was performed, and then the combined organic layer was washed with saturated saline solution (200 ml) and then dried over anhydrous sodium sulfate. After filtering, the filtrate was concentrated under a reduced pressure, the concentrate was applied to a silica gel chromatography, and 7.19 g (99%) of the title compound was obtained in the form of a colorless syrup from a chloroform:methanol=50:1 eluate.

$^1$H-NMR (400 MHz, CDCl$_3$) δ: 0.73 (4H, m), 1.35 (9H, s), 1.36 (3H, s), 1.61 (1H, m), 1.85 (1H, m), 1.97 (1H, m), 2.27 (1H, m), 2.50-2.58 (2H, m), 2.79 (3H, s), 2.99 (1H, m), 3.14-3.19 (1H, m), 7.27-7.30 (5H, m).

Reference Example 40

3-(R)-[1-[N-(tert-butoxycarbonyl)-N-(methyl)amino]
cyclopropyl]pyrrolidine 3-(R)-[1-[N-(tert-butoxycarbonyl)-N-(methyl)amino]cyclopropyl]-1-[1-(S)-phenylethyl]pyrrolidine (7.19 g, 20.9 mmol) was dissolved in ethanol (78 ml), and after adding a 10% palladium carbon catalyst (water content: 50%; 3.9 g), it was stirred at 40° C. for 4 hours under a hydrogen atmosphere at atmospheric pressure. After performing filtration through cellite (ethanol washing), the filtrate was concentrated under a reduced pressure. As a result, 4.38 g (quantitative) of the title compound was obtained in the form of a colorless syrup. The $^1$H-NMR data and the TLC Rf value of this resulting compound agreed with the data indicated previously.

$^1$H-NMR (400 MHz, CDCl$_3$) δ: 0.80 (4H, brs), 1.46 (9H, s), 1.81 (1H, m), 2.04 (1H, brs), 2.28-2.42 (1H, m), 2.54 (1H, brs), 2.84 (3H, s), 2.88-2.96 (3H, m). TLC: Rf=0.1 (chloroform:methanol=9:1)

Reference Example 41

4-(R)-[1-[N-(tert-butoxycarbonyl)-N-(ethyl)amino]
cyclopropyl]-1-[1-(S)-phenylethyl]pyrrolidin-2-one 4-(R)-[1-(tert-butoxycarbonylamino)cyclopropyl]-1-[1-(S)-phenylethyl]pyrrolidin-2-one (4.16 g, 12.1 mmol) was dissolved in dimethylformamide (50 ml). Under a nitrogen atmosphere and at room temperature, 60% oily sodium hydride (580 mg, 14.5 mmol) was added thereto and stirred for 10 minutes, and then ethyl iodide (4.87 ml, 60.5 mmol) was added dropwise. After completion of dripping, the reaction suspension was stirred at room temperature for 15 hours. After adding a saturated aqueous ammonium chloride solution (150 ml) to the reaction suspension while stirring and cooling with ice, extraction with ethyl acetate (150 ml×2) was performed. The combined organic layer was then washed with water (150 ml×2) and saturated saline solution (150 ml) in that order, and then dried over anhydrous sodium sulfate. After filtering, the filtrate was concentrated under a reduced pressure, the residue obtained was applied to a silica gel chromatography, and 4.56 g (quantitative) of the title compound was obtained in the form of a colorless oily substance from an n-hexane:ethyl acetate=1:2 eluate.

$^1$H-NMR (400 MHz, CDCl$_3$) δ: 0.49-0.80 (4H, m), 1.02-1.04 (3H, m), 1.37 (9H, s), 1.49-1.51 (3H, m), 1.92-1.94 (1H, m), 2.04-2.06 (1H, m), 2.36-2.38 (1H, m), 2.67-2.70 (2H, m), 3.20-4.23 (2H, m), 5.48-5.50 (1H, m), 7.26-7.52 (5H, m).

Reference Example 42

3-(R)-[1-[N-(tert-butoxycarbonyl)-N-(ethyl)amino]
cyclopropyl]-1-[1-(S)-phenylethyl]pyrrolidine 4-(R)-[1-[N-(tert-butoxycarbonyl)-N-(ethyl)amino]cyclopropyl]-1-[1-(S)-phenylethyl]pyrrolidin-2-one (4.56 g, 12.1 mmol) was dissolved in anhydrous tetrahydrofuran (80 ml), and a 1.0M borane-tetrahydrofuran complex/tetrahydrofuran solution (48.0 ml, 48.0 mmol) was added dropwise in while stirring and cooling with ice. After completion of dripping, the reaction solution was stirred for 16 hours under the condition of from ice cooling to room temperature. After concentrating the reaction solution under a reduced pressure, a 9:1 mixed solution (100 ml) of ethanol and water was added thereto, and after adding triethylamine (5 ml), it was heated under reflux for 4 hours. After cooling the reaction solution to room temperature, concentration was performed under a reduced pressure, saturated sodium bicarbonate water (100 ml) was added to the residue, extraction with chloroform (100 ml×2) was performed, and then the combined organic layer was washed with saturated saline solution (100 ml) and then dried over anhydrous sodium sulfate. After filtering, the filtrate was concentrated under a reduced pressure, the concentrate was applied to a silica gel chromatography, and 4.26 g (99%) of the title compound was obtained in the form of a colorless syrup from a chloroform:methanol=100:1 to 95:5 eluate.

$^1$H-NMR (400 MHz, CDCl$_3$) δ: 0.54-0.78 (4H, m), 1.09-1.11 (3H, m), 1.33-1.43 (13H, m), 1.84-1.97 (2H, m), 2.26-2.28 (2H, m), 2.56-2.57 (2H, m), 2.86-2.96 (1H, m), 3.13-3.18 (2H, m), 7.21-7.30 (5H, m).

Reference Example 43

3-(R)-[1-[N-(tert-butoxycarbonyl)-N-(ethyl)amino]
cyclopropyl]pyrrolidine 3-(R)-[1-[N-(tert-butoxycarbonyl)-N-(ethyl)amino]cyclopropyl]-1-[1-(S)-phenylethyl]pyrrolidine (3.01 g, 8.40 mmol) was dissolved in ethanol (120 ml), and after adding a 10% palladium carbon catalyst (water content: 50%; 3.0 g), it was stirred at 40° C. for 5 hours under a hydrogen atmosphere at atmospheric pressure. After performing filtration through cellite (ethanol washing), the filtrate was concentrated under a reduced pressure. As a result, 2.16 g (quantitative) of the title compound was obtained in the form of a colorless syrup.

$^1$H-NMR (400 MHz, CDCl$_3$) δ: 0.83-0.85 (4H, m), 1.46 (9H, s), 1.74-1.82 (1H, m), 2.16-2.18 (2H, m), 2.43-2.52 (2H, m), 2.90-2.99 (2H, m), 3.21-3.24 (2H, m).

Reference Example 44

2,3,4-trichlorobenzoic acid

Sodium hydroxide (45.42 g, 1.090 mol) was dissolved in water (220 ml), and while cooling with ice, bromine (16.85 ml, 0.327 mol) was dripped therein over a period of 5 minutes. After stirring the reaction solution at 0° C. for 15 minutes, a dioxane (220 ml) solution of 2',3',4'-trichloroacetophenone (24.40 g, 0.109 mol) was dripped therein at 0° C. over a period of 30 minutes. After stirring at room temperature for 14 hours, water (350 ml) was added and then washed with dichloromethane (350 ml). The aqueous layer obtained was gradually made acidic with concentrated hydrochloric acid while cooling with ice and the resulting crystals were filtered out. After washing the filtered-out crystals with water, the water was removed by azeotropic distillation with toluene. 22.33 g (91%) of the title compound was thereby obtained as a pale yellow powder.

$^1$H-NMR (400 MHz, CDCl$_3$) δ: 7.58 (1H, d, J=8.3 Hz), 7.70 (1H, d, J=8.6 Hz)

Reference Example 45

Ethyl (2,3,4-trichlorobenzoyl)acetate 2,3,4-trichlorobenzoic acid (4.51 g, 20.0 mmol) was dissolved in tetrahydrofuran (80 ml), carbonyldiimidazole (3.89 g, 24.0 mmol) was added thereto while cooling with ice, and then stirred at room temperature for 3 hours (solution A). Meanwhile, malonic acid monoethyl ester monopotassium salt (6.81 g, 40.0 mmol) was suspended in ethyl acetate, and while cooling with ice, triethylamine (13.9 ml, 100.0 mmol) and magnesium chloride (5.71 g, 60.0 mmol) were added thereto. After stirring at room temperature for 3 hours, the reaction solution was cooled with ice and the above-described solution A was dripped into this reaction solution over a period of 10 minutes. After then washing solution A into the reaction solution using tetrahydrofuran (10 ml), it was stirred at room temperature for 14 hours, and then the reaction solution was poured into a 10% aqueous citric acid solution (200 ml). This was then extracted with ethyl acetate (200 ml), washed with saturated saline solution (200 ml), and then dried over anhydrous sodium sulfate. After then removing the drying agent by filtration, the solvent was evaporated under a reduced pressure, and the crude product obtained was subject to silica gel chromatography, thereby obtaining 2.681 g (45%) of the title compound as a pale-red oil from an n-hexane:ethyl acetate=5:1 eluate.

$^1$H-NMR (400 MHz, CDCl$_3$) δ: 1.25 (1.5H, t, J=7.2 Hz), 1.34 (1.5H, t, J=7.0 Hz), 3.99 (1H, s), 4.19 (1H, q, J=7.2 Hz), 4.28 (1H, q, J=7.0 Hz), 5.47 (0.5H, s), 7.37-7.49 (2H, m), 12.45 (0.5H, m)

Reference Example 46

Ethyl 7,8-dichloro-1-[2-(S)-fluoro-1-(R)-cyclopropyl]-1,4-dihydro-4-oxoquinoline-3-carboxylate A mixture of ethyl (2,3,4-trichlobenzoyl)acetate (2.681 g, 9.07 mmol), acetic anhydride (10 ml) and triethyl orthoformate (20 ml) was heated under reflux for 2.5 hours in an oil bath at 140° C. After evaporating the solvent under a reduced pressure, azeotropic distillation was carried out using toluene (3 times) to obtain 3.272 g of a crude ethyl 3-ethoxy-2-(2,3,4-trichlorobenzoyl)acrylate as a pale-red oil.

The above-obtained crude ethyl 3-ethoxy-2-(2,3,4-trichlorobenzoyl)acrylate product (3.272 g) was dissolved in dichloromethane (50 ml), 2-(S)-fluoro-1-(R)-cyclopropylamine tosylate (2.467 g, 9.98 mmol) and triethylamine (1.64 ml, 11.79 mmol) were added thereto in that order while cooling with salted ice, and stirred at room temperature for 19.5 hours. Ethyl acetate (200 ml) was added to the reaction solution, and after washing with 10% aqueous citric acid solution (80 ml×2), saturated aqueous sodium bicarbonate solution (80 ml) and saturated saline solution (80 ml), it was dried over anhydrous sodium sulfate. After then removing the drying agent by filtration, the solvent was evaporated under a reduced pressure to obtain a crude ethyl 3-[2-(S)-fluoro-1-(R)-cyclopropyl]amino-2-(2,3,4-trichlorobenzoyl)acrylate (3.59 g) as a pale-orange, gum-like substance.

The above-obtained crude ethyl 3-[2-(S)-fluoro-1-(R)-cyclopropyl]amino-2-(2,3,4-trichlorobenzoyl)acrylate (3.57 g) was dissolved in dried dioxane (45 ml), and after adding sodium hydride (60% content, 433 mg, 10.82 mmol) while cooling with ice, it was stirred for 14 hours while heating in an oil bath at 50° C. After evaporating the solvent under a reduced pressure, the residue was dissolved in chloroform (150 ml), and after washing with 10% aqueous citric acid solution (50 ml) and saturated saline solution (50 ml), it was dried over anhydrous sodium sulfate. After then removing the drying agent by filtration, the solvent was evaporated under a reduced pressued pressure, and the crude product obtained was subject to silica gel chromatography, thereby obtaining 1.475 g (48%) of the title compound as a pale-yellow powder from a chloroform:ethyl acetate=1:2 eluate.

$^1$H-NMR (400 MHz, CDCl$_3$) δ: 1.35-1.50 (1H, m), 1.41 (3H, t, J=7.1 Hz), 1.55-1.75 (1H, m), 4.08-4.13 (1H, m), 4.39 (2H, q, J=7.1 Hz), 4.80-4.98 (1H, m), 7.53 (1H, d, J=8.5 Hz), 8.34 (1H, d, J=6.8 Hz), 8.57 (1H, d, J=2.7 Hz). MS (m/z): 344 (M$^+$).

Reference Example 47

7,8-dichloro-1-[2-(S)-fluoro-1-(R)-cyclopropyl]-1,4-dihydro-4-oxoquinoline-3-carboxylic acid A mixture of ethyl 7,8-dichloro-1-[2-(S)-fluoro-1-(R)-cyclopropyl]-1,4-dihydro-4-oxoquinoline-3-carboxylate (1.114 g, 3.237 mmol), acetic acid (8 ml) and concentrated hydrochloric acid (4 ml) was heated under reflux for 2 hours in an oil bath at 130° C. After then adding water (40 ml) and cooling with ice, the crystals formed were filtered out and washed with water (5 ml×2), 5% aqueous ethanol solution (5 ml×2), and diethyl ether (5 ml×2), thereby obtaining 909 mg (89%) of the title compound as a pale-yellow powder.

$^1$H-NMR (400 MHz, CDCl$_3$) δ: 1.40-1.80 (2H, m), 4.23-4.28 (1H, m), 4.83-5.02 (1H, m), 7.67 (1H, d, J=8.8 Hz), 8.38 (1H, d, J=8.6 Hz), 8.86 (1H, d, J=2.7 Hz)

Melting point: 198 to 201° C. Specific rotation: $[\alpha]_D^{24.5}$=−24.0° Elemental analysis: As $C_{13}H_8Cl_2FNO_3$; Calcd.: C 49.39%; H 2.55%; N 4.43%. Found: C 49.14%; H 2.40%; N 4.33%. MS (m/z): 315 (M$^+$), 354[(M+K)$^+$]

Example 16

7-[3-(R)-(1-aminocyclopropyl)pyrrolidin-1-yl]-8-chloro-1-[2-(S)-fluoro-1-(R)-cyclopropyl]-1,4-dihydro-4-oxoquinoline-3-carboxylic acid A mixture of 7,8-dichloro-1-[2-(S)-fluoro-1-(R)-140° C. cyclopropyl]-1,4-dihydro-4-oxoquinoline-3-carboxylic acid (253 mg, 0.80 mmol), 3-(R)-[1-(tert-butoxycarbonylamino)cyclopropyl]pyrrolidine (272 mg, 1.20 mmol), N-methyl piperidine (0.195 ml, 1.60 mmol) and dimethyl sulfoxide (3 ml) was stirred for 55 hours while heating in an oil bath at 80° C. and under a nitrogen-replaced atmosphere. After evaporating the solvent, the residue was partitioned in ethyl acetate (50 ml) and 10% aqueous citric acid solution (30 ml), and after separating the organic layer, the organic layer was washed with saturated saline solution (30 ml). The organic layer thus obtained was dried over anhydrous sodium sulfate, and after removing the drying agent by filtration, the solvent was evaporated under a reduced pressure. The residue was subject to silica gel chromatography and a crude 7-{3-(R)-[1-(tert-butoxycarbonylamino)cyclopropyl]pyrrolidin-1-yl}-8-chloro-1-[2-(S)-fluoro-1-(R)-cyclopropyl]-1,4-dihydro-4-oxoquinoline-3-carboxylic acid was obtained from a chloroform:methanol=10:1 eluate.

The above-obtained crude 7-{3-(R)-[1-(tert-butoxycarbonylamino)cyclopropyl]pyrrolidin-1-yl}-8-chloro-1-[2-(S)-fluoro-1-(R)-cyclopropyl]-1,4-dihydro-4-oxoquinoline-3-carboxylic acid was dissolved in concentrated hydrochloric acid (5 ml) while cooling with ice, and after stirring at room temperature for 20 minutes, the solution was transferred into a separation funnel and washed with chloroform (10 ml×10 times or more). Saturated aqueous sodium hydroxide solution was then added while cooling with ice to the aqueous layer after washing, thereby adjusting the pH to >11, and thereafter, the pH was adjusted to 7.7 by adding concentrated hydrochloric acid and 1 mol/l hydrochloric acid. The aqueous layer obtained was then subject to extraction into chloroform (100 ml) and chloroform:methanol=9:1 (100 ml×2), and the combined organic layer was dried over anhydrous sodium sulfate. After removing the drying agent by filtration, the solvent was evaporated under a reduced pressure. The residue was then purified by a preparative chromatography (developed into the lower layer of a 7:3:1 mixture of chloroform:methanol:water), slurry-purified using ethanol-diethyl ether, and then dried under a reduced pressure to obtain 96 mg (30%) of the title compound as a pale-yellow powder.

$^1$H-NMR (400 MHz, 0.1 mol/l NaOD/D$_2$O) δ: 0.45-0.65 (4H, m), 1.15-1.30 (1H, m), 1.50-1.75 (2H, m), 2.00-2.10 (1H, m), 2.10-2.25 (1H, m), 3.25-3.40 (2H, m), 3.55-3.75 (2H, m), 4.10-4.15 (1H, m), 4.90-5.15 (1H, m), 7.05 (1H, d, J=9.0 Hz), 7.99 (1H, d, J=9.3 Hz), 8.39 (1H, d, J=3.7 Hz).

Melting point: 128 to 130° C. Specific rotation: $[\alpha]_D^{24.5}$=−193.0° Elemental analysis: As C$_{20}$H$_{21}$ClFN$_3$O$_3$.1.5H$_2$O: Calcd.: C, 55.49%; H, 5.59%; N, 9.71%. Found: C, 55.74%; H, 5.45%; N, 9.57%. MS (m/z): 406 [(M+H)$^+$]

Reference Example 48

Ethyl 7-fluoro-1-[2-(S)-fluoro-1-(R)-cyclopropyl]-5-hydroxy-8-methyl-1,4-dihydro-4-oxoquinoline-3-carboxylate Ethyl 5-amino-7-fluoro-1-[2-(S)-fluoro-1-(R)-cyclopropyl]-8-methyl-1,4-dihydro-4-oxoquinoline-3-carboxylate (1.414 g, 4.39 mmol) was suspended in 35% aqueous sulfuric acid solution (15 ml), and while cooling with ice, an aqueous sodium nitrite solution (394 mg, 5.70 mmol/4.5 ml) was dripped therein over a period of 5 minutes. After then stirring at 0° C. for 30 minutes, a small amount of urea was added, and at the same temperature, an aqueous copper (II) nitrate trihydrate solution (17.00, 70.2 mmol/155 ml) was dripped therein over a period of 10 minutes. After stirring at 0° C. for 5 minutes, copper (I) oxide (565 mg, 3.95 mmol) was added while stirring the reaction solution violently. After then stirring at room temperature for 20 minutes, extraction into chloroform (200 ml×2) was performed, and after making the aqueous layer slightly basic with sodium bicarbonate, the aqueous layer was extracted with chloroform (150 ml×3). The combined organic layer was then dried over anhydrous sodium sulfate, and after removing the drying agent bt the filtration, the solvent was evaporated under a reduced pressure. The crude product obtained was then subject to a silica gel chromatography, thereby obtaining 297 mg (21%) of the title compound as a yellow powder from a chloroform:methanol=10:1 eluate.

$^1$H-NMR (400 MHz, CDCl$_3$) δ: 1.36-1.47 (1H, m), 1.40 (3H, t, J=7.1 Hz), 1.53-1.63 (1H, m), 2.51 (3H, t, J=2.4 Hz), 3.85-3.90 (1H, m), 4.39 (2H, q, J=7.2 Hz), 4.77-4.96 (1H, m), 6.58 (1H, d, J=11.5 Hz), 8.52 (1H, d, J=3.2 Hz). MS (m/z): 324 [(M+H)$^+$]

Reference Example 49

7-fluoro-1-[2-(S)-fluoro-1-(R)-cyclopropyl]-5-hydroxy-8-methyl-1,4-dihydro-4-oxoquinoline-3-carboxylic acid A mixture of ethyl 7-fluoro-1-[2-(S)-fluoro-1-(R)-cyclopropyl]-5-hydroxy-8-methyl-1,4-dihydro-4-oxoquinoline-3-carboxylate (325 mg, 1.005 mmol), acetic acid (3 ml) and concentrated hydrochloric acid (1.5 ml) was heated under reflux for 2 hours in an oil bath at 120° C. After then adding water (30 ml) and cooling with ice, the crystals formed were filtered out and then washed with water, 5% aqueous ethanol solution, and diethyl ether to obtain 267 mg (90%) of the title compound as a pale-yellow powder.

$^1$H-NMR (400 MHz, CDCl$_3$) δ: 1.40-1.75 (2H, m), 2.58 (3H, t, J=2.5 Hz), 3.99-4.04 (1H, m), 4.80-5.05 (1H, m), 6.70 (1H, d, J=11.3 Hz), 8.76 (1H, d, J=3.2 Hz), 13.17 (0.7H, d, J=1.0 Hz), 13.34 (0.7H, brs).

Melting point: 209 to 213° C. Specific rotation: $[\alpha]_D^{24.7}$=−111.6° Elemental analysis: As C$_{14}$H$_{11}$F$_2$NO$_4$: Calcd.: C, 56.95%; H, 3.76%; N, 4.74%. Found: C, 56.90%; H, 3.74%; N, 4.68%. MS (m/z): 296 [(M+H)$^+$]

Example 17

7-[3-(R)-(1-aminocyclopropyl)pyrrolidin-1-yl]-1-[2-(S)-fluoro-1-(R)-cyclopropyl]-5-hydroxy-8-methyl-1,4-dihydro-4-oxoquinoline-3-carboxylic acid A mixture of 7-fluoro-1-[2-(S)-fluoro-1-(R)-cyclopropyl]-5-hydroxy-8-methyl-1,4-dihydro-4-oxoquinoline-3-carboxylic acid (205 mg, 0.694 mmol), 3-(R)-[1-(tert-butoxycarbonylamino)cyclopropyl]pyrrolidine (314 mg, 1.388 mmol), N-methyl piperidine (0.243 ml, 1.388 mmol), and dimethyl sulfoxide (1.5 ml) was stirred for 66 hours while heating in an oil bath at 80° C. under a nitrogen-replaced atmosphere. After evaporating the solvent, the residue was partitioned in chloroform (50 ml) and 10% aqueous citric acid solution (30 ml), and after separating the organic layer, the aqueous layer was further subject to extraction into chloroform (30 ml). The combined organic layer was then dried over anhydrous sodium sulfate, and after removing the drying agent by filtration, the solvent was evaporated under a reduced pressure to thereby obtain a crude 7-{3-(R)-[1-(tert-butoxycarbonylamino)cyclopropyl]pyrrolidin-1-yl}-1-[2-(S)-fluoro-1-(R)-cyclopropyl]-5-hydroxy-8-methyl-1,4-dihydro-4-oxoquinoline-3-carboxylic acid.

The above obtained crude 7-{3-(R)-[1-(tert-butoxycarbonylamino)cyclopropyl]pyrrolidin-1-yl}-1-[2-(S)-fluoro-1-(R)-cyclopropyl]-5-hydroxy-8-methyl-1,4-dihydro-4-oxoquinoline-3-carboxylic acid was dissolved in concentrated hydrochloric acid (20 ml) while cooling with ice, and after stirring at room temperature for 20 minutes, the solution was transferred into a separation funnel and washed with chloroform (20 ml×5 times). Saturated aqueous sodium hydroxide solution was then added while cooling with ice to the aqueous layer after washing, thereby adjusting the pH to >11, and thereafter, the pH was adjusted to 7.5 to 7.8 by adding concentrated hydrochloric acid and 1 mol/l hydrochloric acid. The aqueous layer obtained was then subject to extraction into chloroform (100 ml), chloroform:methanol=9:1 (100 ml×2), and the lower layer of chloroform:methanol:water=7:3:1 (100 ml), and the combined organic layer was dried over anhydrous sodium sulfate. After removing the drying agent by filtration, the solvent was evaporated under a reduced pressure. The residue was then purified by a preparative chromatography (developed into the lower layer of a 7:3:1 mixture of chloroform:methanol:water), slurry-purified using diethyl ether, and then dried under a reduced pressure to obtain 119 mg (43%) of the title compound as a yellow powder.

$^1$H-NMR (400 MHz, 0.1 mol/l NaOD/D$_2$O) δ: 0.45-0.55 (4H, m), 1.05-1.20 (1H, m), 1.45-1.70 (2H, m), 1.90-2.00 (1H, m), 2.05-2.20 (1H, m), 2.16 (3H, s), 3.05-3.20 (2H, m), 3.25-3.35 (1H, m), 3.40-3.50 (1H, m), 3.90-3.95 (1H, m), 4.90-5.10 (1H, m), 6.16 (1H, s), 8.33 (1H, d, J=3.4 Hz).

Melting point: 203-206° C. Specific rotation: $[\alpha]_D^{25.1}$=−274.4° Elemental analysis: As C$_{21}$H$_{24}$FN$_3$O$_4$.1.5H$_2$O: Calcd: C, 58.87%; H, 6.35%; N, 9.81%. Found: C, 59.23%; H, 6.20%; N, 9.48%. MS (m/z): 402 [(M+H)$^+$]

Example 18

7-[3-(R)-(1-aminocyclopropyl)pyrrolidin-1-yl]-8-cyano-1-[2-(S)-fluoro-1-(R)-cyclopropyl]-1,4-dihydro-4-oxoquinoline-3-carboxylic acid A mixture of ethyl 8-cyano-7-fluoro-1-[2-(S)-fluoro-1-(R)-cyclopropyl]-1,4-dihydro-4-oxoquinoline-3-carboxylate (250 mg, 0.785 mmol), 3-(R)-[1-(tert-butoxycarbonylamino)cyclopropyl]pyrrolidine (267 mg, 1.18 mmol), 1,4-diazabicyclo[2.2.2]octane (132 mg, 1.18 mmol), and dimethyl sulfoxide (13 ml) was stirred for 2 hours at room temperature under a nitrogen-replaced atmosphere. After evaporating the solvent, the residue was partitioned in chloroform (30 ml) and 10% aqueous citric acid solution (30 ml), and the organic layer was separated. The organic layer obtained was dried over anhydrous sodium sulfate, and after removing the drying agent by filtration, the solvent was evaporated under a reduced pressure. The residue was dissolved in concentrated hydrochloric acid (4 ml) and glacial acetic acid (4 ml) at room temperature and then stirred for 12 hours while heating in an oil bath at 110° C. After evaporating the solvent, concentrated hydrochloric acid (2 ml) and water (20 ml) were added, and the solution was transferred into a separation funnel and then washed with chloroform (50 ml). 10 mol/l Aqueous sodium hydroxide solution was then added to the aqueous layer after washing, thereby adjusting the pH to >12. Then after washing with chloroform (50 ml), the pH was adjusted to 8.3 by adding concentrated hydrochloric acid and 1 mol/l hydrochloric acid. The aqueous layer obtained was then concentrated to 5 ml under a reduced pressure, subject to extraction into chloroform:methanol=10:1 (50 ml×3), and the combined organic layer was dried over anhydrous sodium sulfate. After removing the drying agent by filtration, the solvent was evaporated under a reduced pressure. The yellow solids thus obtained were recrystallized in ethanol and then dried under a reduced pressure to obtain 124 mg (40%) of the title compound as a yellow powder.

$^1$H-NMR (400 MHz, DMSO-d6) δ: 0.48-0.51 (4H, m), 1.66-1.90 (3H, m), 1.99-2.03 (1H, m), 2.03-2.09 (1H, m), 3.57-3.70 (3H, m), 3.79-3.83 (1H, m), 4.03-4.08 (1H, m), 5.18-5.35 (1H, m), 7.14 (1H, d, J=9.3 Hz), 8.16 (1H, d, J=9.3 Hz), 8.61 (1H, d, J=3.9 Hz).

Melting point: 138 to 140° C. Specific rotation: $[\alpha]_D^{24.5}$=+19.16° Elemental analysis: As C$_{21}$H$_{21}$FN$_4$O$_3$.1.25H$_2$O: Calcd: C, 60.21%; H, 5.65%; N, 13.07%. Found: C, 60.42%; H, 5.62%; N, 12.72%. MS (m/z): 397[(M+H)$^+$]

Example 19

7-[3-(R)-(1-aminocyclobutyl)pyrrolidin-1-yl]-1-[2-(S)-fluoro-1-(R)-cyclopropyl]-8-methoxy-1,4-dihydro-4-oxoquinoline-3-carboxylic acid A mixture of 7-fluoro-1-[2-(S)-fluoro-1-(R)-cyclopropyl]-8-methoxy-1,4-dihydro-4-oxoquinoline-3-carboxylic acid (290 mg, 0.98 mmol), 3-(R)-[1-(tert-butoxycarbonylamino)cyclobutyl]pyrrolidine (283 mg, 1.18 mmol), triethylamine (0.409 ml, 2.94 mmol), and dimethyl sulfoxide (5 ml) was stirred for 112 hours while heating in an oil bath at 80° C. under an argon-replaced atmosphere. After evaporating the solvent, the residue was partitioned in chloroform (50 ml) and 10% aqueous citric acid solution (30 ml), and after separating the organic layer, the organic layer was washed with saturated saline solution (30 ml). The organic layer obtained was then dried over anhydrous sodium sulfate, and after removing the drying agent by filtration, the solvent was evaporated under a reduced pressure. The residue was subject to a silica gel chromatography and a crude 7-{3-(R)-[1-(tert-butoxycarbonylamino)cyclobutyl]pyrrolidin-1-yl}-1-[2-(S)-fluoro-1-(R)-cyclopropyl]-8-methoxy-1,4-dihydro-4-oxoquinoline-3-carboxylic acid was thereby obtained from a chloroform:methanol=20:1 eluate.

The above obtained crude 7-{3-(R)-[1-(tert-butoxycarbonylamino)cyclobutyl]pyrrolidin -1-yl}-1-[2-(S)-fluoro-1-(R)-cyclopropyl]-8-methoxy-1,4-dihydro-4-oxoquinoline-3-carboxylic acid was dissolved in concentrated hydrochloric acid (5 ml) while cooling with ice, and after stirring for 5 minutes in an ice-water bath, the solution was transferred into a separation funnel and washed with chloroform (10 ml×3 times). 10 mol/l Aqueous sodium hydroxide solution was then added while cooling with ice to the aqueous layer after washing, thereby adjusting the pH to >12, and thereafter, the pH was adjusted to 7.4 by adding concentrated hydrochloric acid and 1 mol/l hydrochloric acid. The aqueous layer obtained was then subject to extraction into chloroform (100 ml×3) and the combined organic layer was dried over anhydrous sodium sulfate. After removing the drying agent by filtration, the solvent was evaporated under a reduced pressure. The residue was then recrystallized in ethyl acetate-hexane and dried under a reduced pressure 99 mg (24%) of the title compound as a yellow powder.

$^1$H-NMR (400 MHz, d$_6$-DMSO) δ: 1.30-1.45 (1H, m), 1.45-1.60 (1H, m), 1.60-1.70 (1H, m), 1.70-2.50 (8H, m), 3.30-3.40 (1H, m), 3.40-3.50 (1H, m), 3.50 (3H, s), 3.56-3.60 (2H, m), 4.03-4.09 (1H, m), 5.00-5.22 (1H, m), 7.09 (1H, d, J=9.1 Hz), 7.92 (1H, d, J=9.1 Hz), 8.57 (1H, d, J=3.4 Hz).

Melting point: 174° C. Elemental analysis: As C$_{22}$H$_{26}$FN$_3$O$_4$.0.25H$_2$O: Calcd: C, 62.92%; H, 6.36%; N, 10.01%. Found: C, 63.20%; H, 6.22%; N, 10.10%. MS (m/z): 416[(M+H)$^+$]

Reference Example 50

3-cyano-2,4-difluorobenzoic acid

After dissolving diisopropylamine (56.0 ml, 395 mmol) in anhydrous tetrahydrofuran (400 ml), the solution was stirred at −15° C. under a nitrogen atmosphere. After dripping therein a hexane solution of n-butyllithium (1.52M, 260 ml, 395 mmol), the solution was stirred while cooling with ice for 1 hour. After cooling this solution to −78° C., a solution, in which 2,6-difluorobenzonitrile (25.0 g, 180 mmol) was dissolved in anhydrous tetrahydrofuran (100 ml), was dripped therein over a period of 1 hour. After completion of dripping, the reaction solution was stirred at −78° C. for 1 hour and then dried carbon dioxide was bubbled into this reaction solution for 30 minutes. Thereafter, the reaction solution was stirred at −78° C. for 1 hour, then raised gradually in temperature, and then stirred at room temperature for 12 hours. 100 ml of 1 mol/l Hydrochloric acid was then added to the reaction solution while cooling with ice and extraction into diethyl ether (500 ml×2) was performed. The combined organic layer was washed with saturated saline solution (500 ml) and then dried over anhydrous sodium sulfate. After filtration, the filtrate was concentrated under a reduced pressure, thereby obtaining 29.7 g (90%) of the yellow, amorphous compound of the title. This product was used in the subsequent reaction without further purification.

$^1$H-NMR (400 MHz, CDCl$_3$) δ: 7.10 (1H, m), 8.32 (1H, m)

Reference Example 51

Ethyl 8-cyano-7-fluoro-1-[2-(S)-fluoro-1-(R)-cyclopropyl]-1,4-dihydro-4-oxoquinoline 3-carboxylate 3-cyano-2,4-difluorobenzoic acid (29.6 g, 162 mmol) was dissolved in dried toluene (250 ml), and after adding a catalytic amount of N,N-dimethylformamide, thionyl chloride (17.7 ml, 243 mmol) was dripped in while stirring at room temperature. Upon completion of dripping, the reaction solution was stirred for 1 hour in an oil bath at 80° C. Then after letting the reaction solution cool, the reaction solution was concentrated under a reduced pressure, toluene (100 ml) was added to the residue, and vacuum concentration was performed again. This operation was repeated 3 times. The concentrate thus obtained was dissolved in anhydrous tetrahydrofuran (200 ml), and this solution was dripped, while stirring and cooling with ice, into a solution, in which triethylamine (30 ml) and ethyl 3-dimethylaminoacrylate (24.3 g, 170 mmol) were dissolved in anhydrous tetrahydrofuran (100 ml). After completion of dripping, the reaction solution was heated under reflux for 12 hours. After then filtering the reaction solution through cellite (washing with diethyl ether), the filtrate was concentrated under reduced pressure and the residue obtained was subject to a short silica gel chromatography. A brown, oily substance was then obtained by vacuum concentration of a chloroform:methanol=100:1 to 100:3 eluate.

This substance was then dissolved in anhydrous tetrahydrofuran (300 ml), 2-(S)-fluoro-1-(R)-cyclopropylamine paratoluenesulfonate (28.2 g, 114 mmol) was added thereto, and while stirring at −15° C., a solution, in which triethylamine (23 ml, 165 mmol) was dissolved in anhydrous tetrahydrofuran (50 ml), was dripped therein gradually. After completion of dripping, the reaction solution was stirred while cooling with ice for 2 hours and then stirred at room temperature for 12 hours. Water (300 ml) was then added to the reaction solution, and vacuum concentration was performed to evaporate the tetrahydrofuran. Water (300 ml) was further added, and then extraction into ethyl acetate (400 ml×3) was performed. After washing the combined organic layer with saturated saline solution (500 ml), it was dried over anhydrous sodium sulfate. After filtration, the filtrate was concentrated under reduced pressure. A yellowish-brown, oily substance was thus obtained.

This substance was dissolved in a dried 1,4-dioxane (400 ml), and while stirring and cooling with ice, 60% oily sodium hydride (4.35 g) was added gradually. This reaction suspension was then stirred at room temperature for 1 hour. After then concentrating the reaction solution to approximately ⅓rd the original volume under a reduced pressure, 0.5 mol/l hydrochloric acid (50 ml) was poured in gradually while cooling with ice. The precipitated solids were filtered out, washed with water, and then washed with small amounts of cold ethanol and diethyl ether, in that order. The crude crystals obtained were purified by recrystallization in isopropanol, and dried under a reduced pressure to obtain 10.6 g (49%) of the title compound as yellowish-white crystals.

Melting point: 172 to 177° C. (decomposed)
$^1$H-NMR (400 MHz, CDCl$_3$) δ: 1.23-1.30 (1H, m), 1.41 (3H, t, J=7.1 Hz), 1.61-1.99 (1H, m), 4.00 (1H, m), 4.40 (2H, q, J=7.1 Hz), 5.10 (1H, dm, J=63.5 Hz), 7.31 (1H, m), 8.52 (1H, d, J=2.6 Hz), 8.77 (1H, m)

Text Example 1

Antibacterial activities of the compounds of this invention were measured in accordance to the standard method designated by the Japan Society of Chemotherapy, with the results shown as MIC values (microgram/ml) units in the following table. For comparison with the MIC values of the compounds of this invention, MIC values of levofloxacin (LVFX), ciprofloxacin (CPFX) and 7-[3-(R)-(1-aminocyclopropyl)pyrrolidin-1-yl]-6-fluoro-1-[2-(S)-fluoro-1-(R)-cyclopropyl]-8-methyl-1,4-dihydro-4-oxoquinoline-3-carboxylic acid (Reference drug 1), which is described in PCT/JP96/00208, are also shown in the table.

TABLE 1

|  | Example 1 | Example 2 | Example 3 | Example 10 | Example 11 | Example 14 | Example 15 | Reference drug 1 | LVFX | CPFX |
|---|---|---|---|---|---|---|---|---|---|---|
| E. coli, NIHJ | ≦0.003 | ≦0.003 | ≦0.003 | ≦0.003 | 0.006 | ≦0.003 | ≦0.003 | ≦0.003 | 0.012 | ≦0.003 |
| S. flexneri, 2A 5503 | 0.006 | 0.012 | ≦0.003 | 0.006 | 0.012 | 0.006 | 0.006 | ≦0.003 | 0.025 | 0.006 |
| Pr. vulgalis, 08601 | ≦0.003 | 0.012 | ≦0.003 | 0.006 | 0.012 | 0.012 | 0.012 | ≦0.003 | 0.012 | ≦0.003 |
| K. pneumoniae, Type 1 | 0.025 | 0.05 | 0.012 | 0.025 | 0.1 | 0.05 | 0.025 | 0.006 | 0.1 | 0.025 |
| Ser. marcescens, 10100 | 0.025 | 0.1 | 0.025 | 0.05 | 0.2 | 0.1 | 0.1 | 0.012 | 0.1 | 0.025 |
| Ps. aeruginosa, 32104 | 0.05 | 0.2 | 0.05 | 0.1 | 0.2 | 0.1 | 0.1 | 0.025 | 0.2 | 0.005 |
| Ps. aeruginosa, 32121 | 0.025 | 0.05 | 0.025 | 0.025 | 0.1 | 0.05 | 0.05 | 0.012 | 0.1 | 0.025 |

TABLE 1-continued

|  | Example 1 | Example 2 | Example 3 | Example 10 | Example 11 | Example 14 | Example 15 | Reference drug 1 | LVFX | CPFX |
|---|---|---|---|---|---|---|---|---|---|---|
| Ps. maltophilia, IID-1275 | 0.2 | 0.2 | 0.05 | 0.1 | 0.2 | 0.2 | 0.2 | ≦0.003 | 0.39 | 0.78 |
| S. aureus, 209P | ≦0.003 | ≦0.003 | ≦0.003 | ≦0.003 | ≦0.003 | ≦0.003 | ≦0.003 | ≦0.003 | 0.2 | 0.1 |
| S. epidermidis, 56500 | ≦0.003 | 0.012 | 0.003 | 0.006 | 0.012 | 0.006 | 0.006 | ≦0.003 | 0.39 | 0.2 |
| Str. pyogenes, G-36 | ≦0.003 | 0.006 | 0.003 | ≦0.003 | 0.012 | ≦0.003 | ≦0.003 | ≦0.003 | 0.2 | 1.56 |
| Str. faecalis, ATCC 19433 | 0.012 | 0.025 | 0.012 | 0.012 | 0.05 | 0.025 | 0.025 | 0.006 | 0.78 | 0.78 |
| S. aureus, 870307 | 0.05 | 0.05 | 0.025 | 0.025 | 0.05 | 0.012 | 0.025 | 0.012 | >6.25 | 3.13 |
| Str. pneumoniae J24 | ≦0.003 | 0.006 | ≦0.003 | ≦0.003 | 0.006 | ≦0.003 | ≦0.003 | ≦0.003 | 0.78 | 0.1 |

Text Example 2

For the compound described as Example 1 of this invention, the micronucleus test in bone marrow of mice was performed by the following method.

Mice groups, each consisting of five, six-week-old, Slc: ddY male mice, were used. The compound of this invention described as Example 1 and 7-[3-(R)-(1-aminocyclopropyl) pyrrolidin-1-yl]-6-fluoro-1-[2-(S)-fluoro-1-(R)-cyclopropyl]-8-methyl-1,4-dihydro-4-oxoquinoline-3-carboxylic acid (Reference drug 1) described in PCT/JP96/00208 were dissolved in and diluted with 0.1 mol/l NaOH/saline solution. The 0.1 mol/l NaOH/saline solvent was used as a control, and as a positive Reference drug, a drug solution, prepared by dissolving and diluting cyclophosphamide (CP) in saline solution, was used. All drug solutions were disinfected by filtration through Mylex GS 0.22 μm filters. With each drug solution, a single intravenous dose of 10 ml/kg was administered at an administration rate of 0.2 ml/min. 24 hours after administration, myeloma cells were collected from the femur bone, the smear preparations were prepared, and these were dyed with acrylic orange. Using a fluorescence microscope, 1000 polychromatic erythrocytes were observed for each individual mouse, and the frequency of occurrence of micronucleated polychromatic erythrocytes and the ratio of orthochromatic erythrocytes and polychromatic erythrocytes among 1000 erythrocytes were calculated.

As a result, a significant difference in the micronucleus induction rate was not seen between the control and any of the 25, 50, and 100 mg/kg administration groups for the compound described as Example 1 and the judgment result was thus negative. That is, the compound described as Example 1 was found to be extremely weak in micronucleus induction and high in safety.

In contrast, with the comparison compound, 7-[3-(R)-(1-aminocyclopropyl)pyrrolidin-1-yl]-6-fluoro-1-[2-(S)-fluoro-1-(R)-cyclopropyl]-8-methyl-1,4-dihydro-4-oxo-quinoline-3-carboxylic acid (Reference drug 1) described in PCT/JP96/00208, micronucleus induction in comparison to the control was clearly seen with the 50 and 100 mg/kg administration groups.

These results show that the compound described as Example 1 of this invention, wherein a fluorine atom of the 6-position of the comparison compound, 7-[3-(R)-(1-aminocyclopropyl)pyrrolidin-1-yl]-6-fluoro-1-[2-(S)-fluoro-1-(R)-cyclopropyl]-8-methyl-1,4-dihydro-4-oxoquinoline-3-carboxylic acid described in PCT/JP96/00208 is replaced by a hydrogen atom, exhibits a potent antibacterial action upon a broad range of both gram-negative bacteria and gram-positive bacteria, including resistant bacteria, and yet is high in safety.

Text Example 3

For the compound of this invention described as Example 1, the blood concentration and organ concentration after oral administration were determined by the following methods. Measurements were also made by the same methods for Reference drug 1.

Method 1: Animal Tests

An administration solution was prepared by dissolving a tested compound to a concentration of 2 mg/ml (as free compound) in distilled water, and using a 2.5 ml disposable syringe or a metal oral probe, the solution was orally administered at a dose of 20 mg/kg to fasting rats (Crj: CD IGS; male; 7-week-old; Charles River Japan, Inc.).

The absorption test groups (4 rats per group; total of 6 groups) were killed by exsanguination while under ether anesthetization 0.25, 0.5, 1, 2, 4, or 6 hours after drug administration, and the blood, liver, kidneys, and lungs were sampled. With the blood, serum was sampled by centrifugation (3000 rpm×15 minutes, 4° C.) after coagulation. Tissues were homogenized after adding 3 to 5 ml of 0.1M phosphate buffer solution (pH 7.0) and the centrifugation supernatants (3000 rmpm×15 minutes, 4° C.) were collected.

The excretion test groups (4 rats per group) were put in a metabolic cage after drug administration, and collected urine samples for 0 to 4 hours and 4 to 24 hours were sampled while cooling with ice, and at the time of sampling, the interior of the cage was washed with approximately 15 ml of 0.1 mol/l phosphate buffer solution (pH 7.0) to recover the urine attached to the interior of the cage. Also in order to examine glucuronide and other conjugated compounds, a part of the sample was separated, hydrolyzed with an equivalent amount of 1 mol/l aqueous sodium hydroxide solution, and thereafter neutralized with 0.5 mol/l hydrochloric acid, and concentration measurements were made on samples prepared in this manner.

Method 2: Drug Concentration Measurements

Determination of drug concentrations in liquid samples were quantified by an agar well method bioassay using the *B. subtilis* ATCC6051 strain as the test organism. A test medium was prepared by inoculating a suspension containing $5 \times 10^7$ CFU/ml of spores of the test bacteria at a proportion of 1% into an nutrient agar (Eiken Kagaku) that was sterilized at 121° C. for 15 minutes and then cooled to approximately 50° C. After placing 10 ml each of this medium in a sterilized Petri dish and solidifying horizontally, four holes of 8 mm diameter were made to prepare a test plate medium. The Bioassay System TDA-1 (Dainippon Seiki) was used for preparation of the test plate media. For the measurements, the test samples (diluted with serum or phosphate buffer solution as necessary), serial dilutions of the drug solutions for calibration (two-fold serial dilutions prepared so that the inhibition ring diameter will be approximately 10 to 30 mm), and a reference drug solution (a drug solution of given concentration for correction of the error among plates; normally, a concentration of forming an inhibition ring of approximately 20 nm is used) were prepared, and 50 µL of the test sample (or the drug solution for calibration) were placed in each of two of the four holes of each plate and 50 µL of the reference solution was placed in each of the other two holes. After addition of the sample, the plate medium was set still for 1 hour at 4° C. to perform preliminary dispersion and then culturing at 37° C. was performed for approximately 18 hours, and the inhibition ring diameters were measured using CA-400 (Dainippon Seiki). The concentrations of the test samples were measured using a calibration curve determined by second-order regression from the logarithmic values of the drug concentration of the calibration curve serial dilutions and the inhibition ring diameters.

For the tissue concentration (µg/ml), the concentration (µg/ml) in the homogenate supernatant was determined from the tissue weight (g) and the added phosphate buffer amount (ml) and using the following equation:

[Tissue concentration]=[Homogenate concentration]×
([Tissue weight]+[Buffer solution amount])/[Tissue weight]

The urinary excretion rate (%) was determined from the amount (µg) of drug administered, amount (ml) of urine (or washing solution), and concentration (µ/ml) in urine (or washing solution):

[(Urinary excretion rate]=100×([Amount of urine]×
[Concentration in urine])/[Amount of drug administered]

Method 3: Calculation of Pharmacokinetic Parameters

For each drug, the pharmacokinetic parameters in rats were calculated based on mean concentration, by non-compartmental analysis, and using the pharmacodynamics analysis software, PSAG-CP (Asmedica).

The serum concentration and the organ concentration for liver, kidneys, and lungs of the compound of Example 1 and Reference drug 1, determined by the above methods, are shown in Table 2.

lent in oral absorption. It is also apparent that the compound of this invention is excellent in tissue penetration.

The structures of the compounds that were compared in activities are as follows.

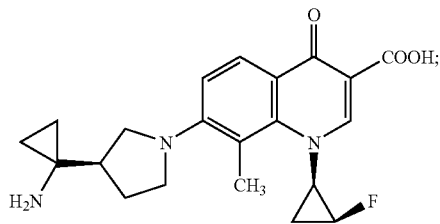

Compound described as Example 1

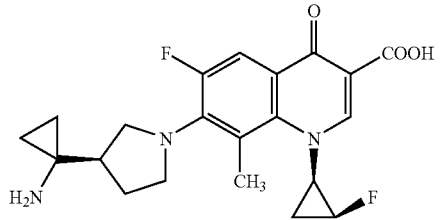

Compound described in PCT/JP96/00208
Reference drug 1

INDUSTRIAL APPLICABILITY

Compounds of this invention exhibit excellent antibacterial action upon a broad range of both gram-negative and gram-positive bacteria and, in particular, exhibit potent antibacterial activity even against resistant gram-positive bacteria, such as methicillin-resistant *Staphylococcus aureus* (MRSA), penicillin-resistant *Streptococcus pneumoniae* (PRSP), vancomycin-resistant *Enterococcus* (VRE), etc., and

TABLE 2

| Compound (addition product) | | | Compound of Example 1 (1 HCl, 0.25 IPA, 0.25 H$_2$O) | Reference Drug (1 MsOH, 1 H$_2$O) |
|---|---|---|---|---|
| Serum | C$_{max}$(µg/ml) | | 1.7 | 1.6 |
| | t$_{1/2}$(h) | | 1.2 | 1.0 |
| | AUC$_{0-4h}$(µg · h/ml) | | 3.1 | 2.3 |
| Tissue | C$_{max}$(µg/g) | Liver | 27.4 | 11.6 |
| | | Kidney | 14.2 | 5.0 |
| | | Lung | 3.8 | 3.0 |
| | AUC$_{0-4h}$ | Liver | 34.5(11.0) | 10.4(4.6) |
| | (tissue/serum | Kidney | 29.0(9.2) | 7.1(3.1) |
| | ratio) | Lung | 10.0(3.2) | 5.3(2.3) |
| Urinary recovery ratio (per dose) | 0-24 h | | 8.1 | 1.8 |
| | after addition of conjugated compounds | | 8.7 | 2.3 |

As is apparent from Table 2, the compound of this invention was found to be distributed at higher concentrations, for both serum and tissue, in comparison to Reference drug 1. It is thus apparent that the compound of this invention is excelquinolone-resistant bacteria, and yet are excellent in safety characteristics, such as being negative in micronucleus tests, and excellent in pharmacokinetics, such as being improved in urinary recovery rates and being excellent in oral absorption and tissue penetration, etc. The compounds of this invention are thus useful as antibacterial compounds to be used in chemotherapy against microbial infections.

The invention claimed is:

1. A compound represented by the following general formula (I), or a salt thereof:

$$\text{I}$$

wherein $R^1$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms, which may have a substituent, an aryl group, which may have a substituent, a heteroaryl group, which may have a substituent, an alkoxy group having 1 to 6 carbon atoms, or an alkylamino group having 1 to 6 carbon atoms;

$R^2$ represents an alkylthio group having 1 to 6 carbon atoms or a hydrogen atom, wherein $R^2$ and the abovementioned $R^1$ may be integrated to form a ring structure by incorporating a part of the mother skeleton, the thus formed ring may contain a sulfur atom as a ring-constituent atom, and the ring may be substituted by an alkyl group having 1 to 6 carbon atoms, which may have a substituent;

$R^3$ represents a phenylalkyl group composed of an alkylene group having 1 to 6 carbon atoms and a phenyl group, an alkyl group having 1 to 6 carbon atoms, an alkoxymethyl group having 2 to 7 carbon atoms, a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxole-4-ylmethyl group, or a 3-acetoxy-2-oxobutyl group;

$R^4$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a hydroxyl group, a thiol group, or a halogenomethyl group, and among the above, the amino group may have one or more substituents selected from among the group consisting of an alkyl group having 1 to 6 carbon atoms, an acyl group having 2 to 5 carbon atoms, and a formyl group;

A represents a nitrogen atom or a partial structure represented by formula (II):

$$\text{II}$$

wherein $X^1$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a halogen atom, a cyano group, a halogenomethyl group, or a halogenomethoxy group, among the above, the amino group may have one or more substituents selected from the group consisting of an alkyl group having 1 to 6 carbon atoms, an acyl group having 2 to 5 carbon atoms, and a formyl group, wherein $X^1$ and the aforementioned $R^1$ may be integrated to form a ring structure by incorporating a part of the mother skeleton, the thus formed ring may contain an oxygen atom, a nitrogen atom, or a sulfur atom as a ring constituent atom, and this ring may be substituted by an alkyl group having 1 to 6 carbon atoms, which may have a substituent;

each of $R^5$ and $R^6$ independently represents a hydrogen atom or a substituted carboxyl group derived from an amino acid, dipeptide, or tripeptide, wherein the alkyl group may have one or more substituents selected from the group consisting of an alkylthio group having 1 to 6 carbon atoms, an alkoxy group having 1 to 6 carbon atoms, a hydroxyl group, and a halogen atom; and n represents an integer 1 or 2.

2. The compound according to claim 1, or a salt thereof, wherein the compound of formula (I) is a stereochemically pure compound.

3. The compound according to claim 1 or 2, or a salt thereof, wherein n in the formula (I) is 1.

4. The compound according to claim 1 or 2, or a salt thereof, wherein $R^3$ in the formula (I) is a hydrogen atom.

5. The compound according to claim 1 or 2, a salt thereof, wherein $R^2$ in the formula (I) is a hydrogen atom.

6. The compound according to claim 1 or 2, or a salt thereof, wherein $R^4$ in the formula (I) is a hydrogen atom.

7. The compound according to claim 1 or 2, or a salt thereof, wherein A in the formula (I) is a partial structure represented by the formula (II).

8. The compound according to claim 7, or a salt thereof, wherein $X^1$ in the formula (II) is a methoxy group, a methyl group, a difluoromethoxy group, a fluorine atom, or a chlorine atom.

9. The compound according to claim 7, or a salt thereof, wherein $X^1$ in the formula (II) is a methoxy group or a methyl group.

10. The compound according to claim 1 or 2, or a salt thereof, wherein each of $R^5$ and $R^6$ in the formula (I) is a hydrogen atom.

11. The compound according to claim 1 or 2, or a salt thereof, wherein one of either $R^5$ or $R^6$ in formula (I) is a hydrogen atom and the other is a substituted carboxyl group derived from an amino acid, a dipeptide, or a tripeptide.

12. The compound according to claim 1 or 2, or a salt thereof, wherein the cyclic alkyl group having 3 to 6 carbon atoms, which may have a substituent, in $R^1$ is a halogenocyclopropyl group.

13. The compound according to claim 12, or a salt thereof, wherein the halogenocyclopropyl group is a 1,2-cis-2-halogenocyclopropyl group.

14. The compound according to claim 13, or a salt thereof, wherein the halogenocyclopropyl group is a stereochemically pure substituent.

15. The compound according to claim 14, or a salt thereof, wherein the halogenocyclopropyl group is a (1R,2S)-2-halogenocyclopropyl group.

16. The compound according to claim 12, or a salt thereof, wherein the halogen atom of the halogenocyclopropyl group is a fluorine atom.

17. 7-[3-(R)-(1-aminocyclopropyl)pyrrolidin-1-yl]-1-[2-(S)-fluoro-1-(R)-cyclopropyl]-1,4-dihydro-4-oxo-1,8-naphthyridine-3-carboxylic acid, or a salt thereof.

18. 7-[3-(R)-(1-aminocyclopropyl)pyrrolidin-1-yl]-1-[2-(S)-fluoro-1-(R)-cyclopropyl]-1,4-dihydro-4-oxoquinolone-3-carboxylic acid, or a salt thereof.

19. 7-[3-(R)-(1-aminocyclopropyl)pyrrolidin-1-yl]-1-[2-(S)-fluoro-1-(R)-cyclopropyl]-8-chloro-1,4-dihydro-4-oxoquinolone-3-carboxylic acid, or a salt thereof.

20. 7-[3-(R)-(1-aminocyclopropyl)pyrrolidin-1-yl]-1-[2-(S)-fluoro-1-(R)-cyclopropyl]-8-fluoro-1,4-dihydro-4-oxoquinolone-3-carboxylic acid, or a salt thereof.

21. 7-[3-(R)-(1-aminocyclopropyl)pyrrolidin-1-yl]-1-[2-(S)-fluoro-1-(R)-cyclopropyl]-8-difluoromethoxy-1,4-dihydro-4-oxoquinolone-3-carboxylic acid, or a salt thereof.

22. 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid, or a salt thereof.

23. 7-[3-(R)-[1-(methylamino)cyclopropyl]pyrrolidin-1-yl]-1-[2-(S)-fluoro-1-(R)-cyclopropyl]-1,4-dihydro-8-methoxy-4-oxoquinolone-3-carboxylic acid, or a salt thereof.

24. 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid, or a salt thereof.

25. 7-[3-(R)-[1-(methylamino)cyclopropyl]pyrrolidin-1-yl]-1-[2-(S)-fluoro-1-(R)-cyclopropyl]-1,4-dihydro-8-methyl-4-oxoquinolone-3-carboxylic acid, or a salt thereof.

26. 7-[3-(R)-[1-(ethylamino)cyclopropyl]pyrrolidin-1-yl]-1-[2-(S)-fluoro-1-(R)-cyclopropyl]-1,4-dihydro-8-methyl-4-oxoquinolone-3-carboxylic acid, or a salt thereof.

27. 5-amino-7-[3-(R)-(1-aminocyclopropyl)pyrrolidin-1-yl]-1-[2-(S)-fluoro-1-(R)-cyclopropyl]-1,4-dihydro-8-fluoro-4-oxoquinolone-3-carboxylic acid, or a salt thereof.

28. 5-amino-7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid, or a salt thereof.

29. 5-amino-7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid, or a salt thereof.

30. 5-amino-7-[3-(R)-[1-(methylamino)cyclopropyl]pyrrolidin-1-yl]-1-[2-(S)-fluoro-1-(R)-cyclopropyl]-1,4-dihydro-8-methoxy-4-oxoquinolone-3-carboxylic acid, or a salt thereof.

31. 10-[3-(R)-(1-aminocyclopropyl)pyrrolidin-1-yl]-2,3-dihydro-3-(S)-methyl-7-oxo-7H-pyrido[1,2,3-de][1,4]benzoxazine-6-carboxylic acid, or a salt thereof.

32. 1-(cyclopropyl)-8-methyl-7-[3-(R)-[1-(methylamino)cyclopropyl]pyrrolidin-1-yl]-1,4-dihydro-4-oxoquinolone-3-carboxylic acid, or a salt thereof.

33. A pharmaceutical composition, which comprises the compound described in any one of claims 1, 22, and 24, or a salt thereof, as an active ingredient.

34. An antibacterial composition, which comprises the compound described in any one of claims 1, 22, and 24, or a salt thereof, as an active ingredient.

35. A method for treating a bacterial infection, which comprises administrating the compound described in any one of claims 1, 22, and 24, or a salt thereof, as an active ingredient.

36. A method for producing a pharmaceutical composition, which comprises mixing the compound described in any one of claims 1, 22, and 24, or a salt thereof, with a pharmaceutical carrier.

37. A method for producing an antibacterial composition, which comprises mixing the compound described in any one of claims 1, 22, and 24, or a salt thereof, with a pharmaceutical carrier.

38. The method according to claim 35, wherein the bacterial infection is caused by a drug-resistant bacteria.

39. The method according to claim 38, wherein the drug-resistant bacteria is a quinolone-resistant bacteria.

40. The method according to claim 38, wherein the drug-resistant bacteria is a gram-positive bacteria.

41. The method according to claim 38, wherein the drug-resistant bacteria is methicillin-resistant *Staphylococcus aureus* (MRSA).

42. The method according to claim 38, wherein the drug-resistant bacteria is penicillin-resistant *Streptococcus pneumoniae* (PRSP).

43. The method according to claim 38, wherein the drug-resistant bacteria is vancomycin-resistant *Enterococcus* (VRE).

44. The method according to claim 38, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

45. The method according to claim 39, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

46. The method according to claim 40, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

47. The method according to claim 41, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

48. The method according to claim 42, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

49. The method according to claim 43, wherein the active ingredient is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

50. The method according to claim 38, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

51. The method according to claim 39, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

52. The method according to claim 40, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

53. The method according to claim 41, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

54. The method according to claim 42, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

55. The method according to claim 43, wherein the active ingredient is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

56. The compound according to claim 22, wherein the compound is 7-[3-(R)-(1-aminocyclopropyl)pyrrolidin-1-yl]-1-[2-(S)-fluoro-1-(R)-cyclopropyl]-1,4-dihydro-8-methoxy-4-oxoquinolone-3-carboxylic acid.

57. The compound according to claim 24, wherein the compound is 7-[3-(R)-(1-aminocyclopropyl)pyrrolidin-1-yl]-1-[2-(S)-fluoro-1-(R)-cyclopropyl]-1,4-dihydro-8-methyl-4-oxoquinolone-3-carboxylic acid.

58. 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid, or a salt thereof.

59. A pharmaceutical composition, which comprises the compound described in claim 58, or a salt thereof, as an active ingredient.

60. An antibacterial composition, which comprises the compound described in claim 58, its or a salt thereof, as an active ingredient.

61. A method for treating a bacterial infection, which comprises administrating the compound described in claim 58, or a salt thereof, as an active ingredient.

62. A method for producing a pharmaceutical composition, which comprises mixing the compound described in claim 58, or a salt thereof, with a pharmaceutical carrier.

63. A method for producing an antibacterial composition, which comprises mixing the compound described in claim 58, or a salt thereof, with a pharmaceutical carrier.

64. The method according to claim 61, wherein the bacterial infection is caused by a drug-resistant bacteria.

65. The method according to claim 64, wherein the drug-resistant bacteria is a quinolone-resistant bacteria.

66. The method according to claim 64, wherein the drug-resistant bacteria is a gram-positive bacteria.

67. The method according to claim 64, wherein the drug-resistant bacteria is methicillin-resistant *Staphylococcus aureus* (MRSA).

68. The method according to claim 64, wherein the drug-resistant bacteria is penicillin-resistant *Streptococcus pneumoniae* (PRSP).

69. The method according to claim 64, wherein the drug-resistant bacteria is vancomycin-resistant *Enterococcus* (VRE).

70. The method according to claim 64, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

71. The method according to claim 65, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

72. The method according to claim 66, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

73. The method according to claim 67, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

74. The method according to claim 68, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

75. The method according to claim 69, wherein the active ingredient is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

76. The compound according to claim 58, wherein the compound is 1-[2-(S)-fluoro-1-(R)-cyclopropyl]-8-methyl-7-[3-(R)-[1-(methylamino)cyclopropyl]pyrrolidin-1-yl]-1,4-dihydro-4-oxoquinolone-3-carboxylic acid.

77. A compound represented by the following general formula (I), or a salt thereof:

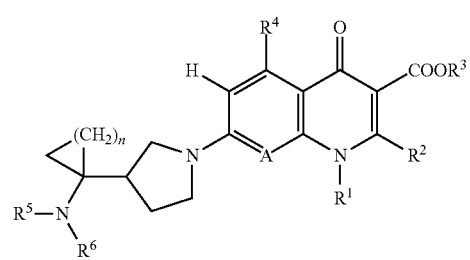

wherein $R^1$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms, which may have a substituent, an aryl group, which may have a substituent, a heteroaryl group, which may have a substituent, an alkoxy group having 1 to 6 carbon atoms, or an alkylamino group having 1 to 6 carbon atoms;

$R^2$ represents an alkylthio group having 1 to 6 carbon atoms or a hydrogen atom, wherein $R^2$ and the abovementioned $R^1$ may be integrated to form a ring structure by incorporating a part of the mother skeleton, the thus formed ring may contain a sulfur atom as a ring-constituent atom, and the ring may be substituted by an alkyl group having 1 to 6 carbon atoms, which may have a substituent;

$R^3$ represents a phenylalkyl group composed of an alkylene group having 1 to 6 carbon atoms and a phenyl group, an alkyl group having 1 to 6 carbon atoms, an alkoxymethyl group having 2 to 7 carbon atoms, a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxole-4-ylmethyl group, or a 3-acetoxy-2-oxobutyl group;

$R^4$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a hydroxyl group, a thiol group, or a halogenomethyl group, and among the above, the amino group may have one or more substituents selected from among the group consisting of an alkyl group having 1 to 6 carbon atoms, an acyl group having 2 to 5 carbon atoms, and a formyl group;

A represents a nitrogen atom or a partial structure represented by formula (II):

wherein $X^1$ represents an alkyl group having 1 to 6 carbon atoms, an alkenyl group having 2 to 6 carbon atoms, an alkynyl group having 2 to 6 carbon atoms, an alkoxy group having 1 to 6 carbon atoms, a hydrogen atom, an amino group, a halogen atom, a cyano group, a halogenomethyl group, or a halogenomethoxy group, among the above, the amino group may have one or more substituents selected from the group consisting of an alkyl group having 1 to 6 carbon atoms, an acyl group having 2 to 5 carbon atoms, and a formyl group, wherein $X^1$ and the aforementioned $R^1$ may be integrated to form a ring structure by incorporating a part of the mother skeleton, the thus formed ring may contain an oxygen atom, a nitrogen atom, or a sulfur atom as a ring constituent atom, and this ring may be substituted by an alkyl group having 1 to 6 carbon atoms, which may have a substituent;

each of $R^5$ and $R^6$ independently represents an alkyl group having 1 to 6 carbon atoms, a hydrogen atom, or a substituted carboxyl group derived from an amino acid, dipeptide, or tripeptide, wherein the alkyl group may have one or more substituents selected from the group consisting of an alkylthio group having 1 to 6 carbon atoms, an alkoxy group having 1 to 6 carbon atoms, a hydroxyl group, and a halogen atom; and n represents an integer 1 or 2.

* * * * *